US006656966B2

(12) United States Patent
Garvey et al.

(10) Patent No.: US 6,656,966 B2
(45) Date of Patent: Dec. 2, 2003

(54) NITROSATED AND NITROSYLATED TAXANES, COMPOSITIONS AND METHODS OF USE

(75) Inventors: David S. Garvey, Dover, MA (US); L. Gordon Letts, Dover, MA (US); Chia-En Lin, Burlington, MA (US); Stewart K. Richardson, Tolland, CT (US); Tiansheng Wang, Concord, MA (US)

(73) Assignee: NitroMed, Inc., Bedford, MA (US)

( * ) Notice: Subject to any disclaimer, the term of this patent is extended or adjusted under 35 U.S.C. 154(b) by 41 days.

(21) Appl. No.: 09/886,494

(22) Filed: Jun. 22, 2001

(65) Prior Publication Data

US 2002/0010146 A1 Jan. 24, 2002

Related U.S. Application Data

(60) Provisional application No. 60/213,294, filed on Jun. 22, 2000, and provisional application No. 60/226,090, filed on Aug. 18, 2000.

(51) Int. Cl.$^7$ .................. A61K 31/337; C07D 305/14
(52) U.S. Cl. .................. 514/449; 549/510; 549/511
(58) Field of Search .................. 549/510, 511; 514/449

(56) References Cited

U.S. PATENT DOCUMENTS

| | | | |
|---|---|---|---|
| 4,703,039 A | 10/1987 | Hawiger et al. | 514/21 |
| 4,885,173 A | 12/1989 | Stanley et al. | 424/440 |
| 4,900,719 A | 2/1990 | Means et al. | 514/18 |

(List continued on next page.)

FOREIGN PATENT DOCUMENTS

| | | |
|---|---|---|
| EP | 0 624 377 | 11/1994 |
| EP | 0 639 577 | 2/1995 |
| EP | 0 558 959 | 4/1997 |
| WO | WO 93/17121 | 9/1993 |
| WO | WO 94/15599 | 7/1994 |
| WO | WO 95/20582 | 8/1995 |
| WO | WO 96/00724 | 1/1996 |
| WO | WO 96/16645 | 6/1996 |
| WO | WO 96/40091 | 12/1996 |
| WO | WO 97/10234 | 3/1997 |
| WO | WO 97/19938 | 6/1997 |
| WO | WO 97/32578 | 9/1997 |
| WO | WO 97/33552 | 9/1997 |
| WO | WO 98/00419 | 1/1998 |
| WO | WO 98/21193 | 5/1998 |
| WO | WO 98/24427 | 6/1998 |
| WO | WO 98/28288 | 7/1998 |
| WO | WO 98/37765 | 9/1998 |
| WO | WO 98/38862 | 9/1998 |
| WO | WO 98/48852 | 11/1998 |
| WO | WO 99/02648 | 1/1999 |
| WO | WO 99/14209 | 3/1999 |
| WO | WO 99/18949 | 4/1999 |
| WO | WO 99/21908 | 5/1999 |
| WO | WO 99/31079 | 6/1999 |
| WO | WO 99/49901 | 10/1999 |
| WO | WO 99/55317 | 11/1999 |
| WO | WO 99/57105 | 11/1999 |
| WO | WO 99/62510 | 12/1999 |
| WO | WO 00/10988 | 3/2000 |
| WO | WO 00/61537 | 10/2000 |
| WO | WO 00/61541 | 10/2000 |
| WO | WO 01/10344 | 2/2001 |

OTHER PUBLICATIONS

Díaz, J. Fernando, et al., "Changes in Microtubule Protofilament Number Induced by Taxol Binding to an Easily Accessible Site," *The Journal of Biological Chemistry*, vol. 273, No. 50, pp. 33803–33810 (Dec. 1998).

Gelmon, Karen, The Taxoids: Paclitaxel and Docetaxel [Drug Profile], *The Lancet*, vol. 344 (8932), pp. 1267–1272 (Nov. 1994).

Ojima, Iwao, et al., "A Common Pharmacophore for Cytotoxic Natural Products that Stabilize Microtubules," *Proc. Natl. Acad. Sci. USA*, vol. 96, pp. 4256–4261 (Apr. 1999).

Rao, Koppaka V., et al., "Selective Nitration of Paclitaxel and Related Taxanes," *Tetrahedron Letters*, vol. 274, Issue 53, pp. 37990–37994 (Dec. 1999).

Takahashi, Takashi, et al., "Design and Synthesis of a Water-Soluble Taxol Analogue: Taxol-Sialyl Conjugate," *Bioorganic & Medicinal Chemistry Letters*, pp. 113–116 (1998).

White, James G., et al., "Influence of a Microtubule Stabilizing Agent on Platelet Structural Physiology," *American Journal Pathologists*, vol. 112, No. 2, pp. 207–217 (Aug. 1983).

*Primary Examiner*—Ba K. Trinh
(74) *Attorney, Agent, or Firm*—Hale and Dorr LLP

(57) ABSTRACT

The present invention describes novel nitrosated and/or nitrosylated taxanes, and novel compositions comprising at least one nitrosated and/or nitrosylated taxane, and, optionally, at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The present invention also provides novel compositions comprising at least one taxane and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The compounds and compositions of the present invention can also be bound to a matrix. The present invention also provides methods for treating or preventing cardiovascular diseases and disorders, autoimmune diseases, pathological conditions resulting from abnormal cell proliferation, polycystic kidney disease, inflammatory disease, preserving organs and/or tissues or to inhibit wound contraction, particularly the prophylactic and/or therapeutic treatment of restenosis, by administering nitrosated and/or nitrosylated taxane or parent taxanes in combination with nitric oxide donors that are capable of releasing nitric oxide or indirectly delivering or transferring nitric oxide to targeted sites under physiological conditions.

113 Claims, 3 Drawing Sheets

U.S. PATENT DOCUMENTS

| | | | |
|---|---|---|---|
| 4,960,790 A | 10/1990 | Stella et al. | 514/449 |
| 5,157,049 A | 10/1992 | Haugwitz et al. | 514/449 |
| 5,278,192 A | 1/1994 | Fung et al. | 514/645 |
| 5,282,785 A | 2/1994 | Shapland et al. | 604/21 |
| 5,284,864 A | 2/1994 | Holton et al. | 514/21 |
| 5,286,254 A | 2/1994 | Shapland et al. | 604/21 |
| 5,399,726 A | 3/1995 | Holton et al. | 549/510 |
| 5,428,070 A | 6/1995 | Cooke et al. | 514/557 |
| 5,482,925 A | 1/1996 | Hutsell | 514/11 |
| 5,550,261 A | 8/1996 | Bouchard et al. | 549/510 |
| 5,616,608 A | 4/1997 | Kinsella et al. | 514/449 |
| 5,629,433 A | 5/1997 | Zheng et al. | 549/510 |
| 5,646,176 A | 7/1997 | Golik et al. | 514/444 |
| 5,665,077 A | 9/1997 | Rosen et al. | 604/266 |
| 5,679,400 A | 10/1997 | Tuch | 427/2.14 |
| 5,688,977 A | 11/1997 | Sisti et al. | 549/510 |
| 5,703,117 A | 12/1997 | Mayhew et al. | 514/449 |
| 5,760,072 A | 6/1998 | de Bont et al. | 514/449 |
| 5,773,431 A | 6/1998 | Javitt | 514/177 |
| 5,780,653 A * | 7/1998 | Tao et al. | 549/510 |
| 5,797,887 A | 8/1998 | Rosen et al. | 604/265 |
| 5,800,385 A | 9/1998 | Demopulos et al. | 604/507 |
| 5,808,113 A | 9/1998 | Murray et al. | 549/510 |
| 5,811,447 A | 9/1998 | Kunz et al. | 514/411 |
| 5,824,049 A | 10/1998 | Ragheb et al. | 623/1.44 |
| 5,837,008 A | 11/1998 | Berg et al. | 128/898 |
| 5,852,058 A | 12/1998 | Cooke et al. | 514/564 |
| 5,861,168 A | 1/1999 | Cooke et al. | 424/424 |
| 5,886,026 A | 3/1999 | Hunter et al. | 514/449 |
| 5,912,263 A | 6/1999 | Menichincheri et al. | 514/449 |
| 5,916,913 A | 6/1999 | Joseph | 514/449 |
| 5,919,815 A | 7/1999 | Bradley et al. | 514/449 |
| 5,945,452 A | 8/1999 | Cooke et al. | 514/564 |
| 5,951,458 A | 9/1999 | Hastings et al. | 600/3 |
| 5,965,739 A | 10/1999 | Kelly et al. | 548/215 |
| 5,977,163 A | 11/1999 | Li et al. | 514/449 |
| 5,981,564 A | 11/1999 | Page et al. | 514/400 |
| 5,981,568 A | 11/1999 | Kunz et al. | 514/411 |
| 5,994,444 A | 11/1999 | Trescony et al. | 524/429 |
| 5,998,656 A | 12/1999 | Holton et al. | 560/160 |
| 6,017,935 A | 1/2000 | Mastalerz et al. | 514/337 |
| 6,017,948 A | 1/2000 | Rubinfeld et al. | 514/449 |
| 6,028,205 A | 2/2000 | Holton et al. | 549/510 |
| 6,063,407 A | 5/2000 | Zapol et al. | 424/718 |
| 6,071,952 A | 6/2000 | Owens et al. | 514/449 |
| 6,072,060 A | 6/2000 | Swindell et al. | 549/510 |
| 6,080,877 A | 6/2000 | Swindell et al. | 549/510 |
| 6,147,234 A | 11/2000 | Holton et al. | 549/510 |
| 6,177,456 B1 | 1/2001 | Yankov et al. | 514/449 |
| 6,231,600 B1 | 5/2001 | Zhong | 623/1.42 |
| 6,262,281 B1 | 7/2001 | Swindell et al. | 549/510 |

* cited by examiner

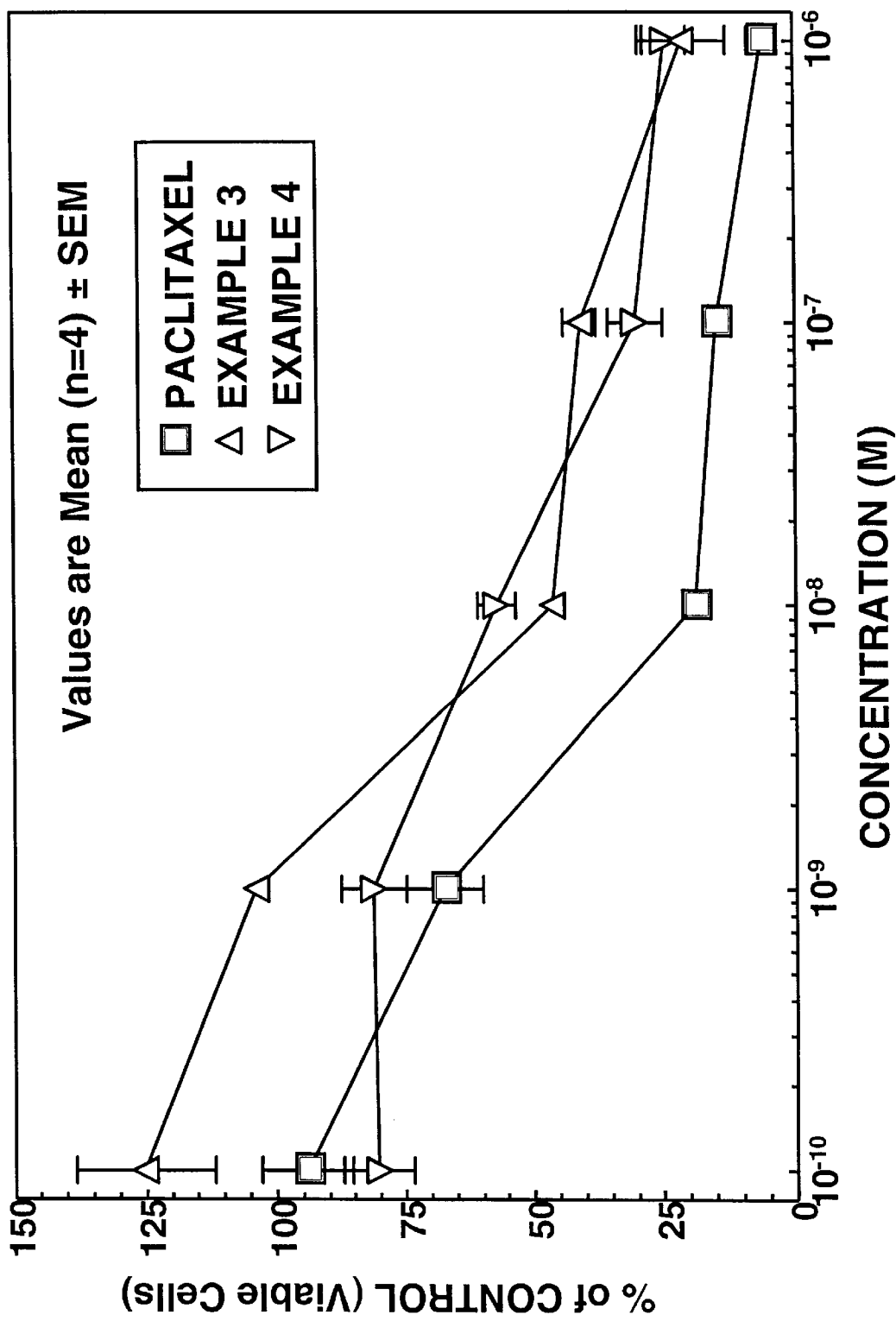

NITROSATED AND NITROSYLATED TAXANES, COMPOSITIONS AND METHODS OF USE

RELATED APPLICATIONS

This application claims priority to U.S. Provisional Application No. 60/213,294 filed Jun. 22, 2000 and U.S. Provisional Application No. 60/226,090 filed Aug. 18, 2000.

FIELD OF THE INVENTION

The present invention describes novel nitrosated and/or nitrosylated taxanes, and novel compositions comprising at least one nitrosated and/or nitrosylated taxane, and, optionally, at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The present invention also provides novel compositions comprising at least one taxane and at least one compound that donates, transfers or releases nitric oxide, elevates endogenous levels of endothelium-derived relaxing factor, stimulates endogenous synthesis of nitric oxide or is a substrate for nitric oxide synthase and/or at least one therapeutic agent. The compounds and compositions of the present invention can also be bound to a matrix. The present invention also provides methods for treating or preventing cardiovascular diseases and disorders, autoimmune diseases, pathological conditions resulting from abnormal cell proliferation, polycystic kidney disease, inflammatory diseases, preserving organs and/or tissues, or to inhibit wound contraction, particularly the prophylactic and/or therapeutic treatment of restenosis, by administering nitrosated and/or nitrosylated taxane or parent taxanes in combination with nitric oxide donors that are capable of releasing nitric oxide or indirectly delivering or transferring nitric oxide to targeted sites under physiological conditions.

BACKGROUND OF THE INVENTION

Endothelium-derived relaxing factor (EDRF) is a vascular relaxing factor secreted by the endothelium and is important in the control of vascular tone, blood pressure, inhibition of platelet aggregation, inhibition of platelet adhesion, inhibition of mitogenesis, inhibition of proliferation of cultured vascular smooth muscle, inhibition of leukocyte adherence and prevention of thrombosis. EDRF has been identified as nitric oxide (NO) or a closely related derivative thereof (Palmer et al, *Nature,* 327:524–526 (1987); Ignarro et al, Proc. Natl. Acad. Sci. USA, 84:9265–9269 (1987)).

Removal of the endothelium is a potent stimulus for neointimal proliferation, a common mechanism underlying the restenosis of atherosclerotic vessels after balloon angioplasty (Liu et al., *Circulation,* 79:1374–1387 (1989); Fems et al., *Science,* 253:1129–1132 (1991)). Balloon arterial injury results in endothelial denudation and subsequent regrowth of dysfunctional endothelium (Saville, *Analyst,* 83:670–672 (1958)) that may contribute to the local smooth muscle cell proliferation and extracellular matrix production that result in reocclusion of the arterial lumen. Nitric oxide dilates blood vessels (Vallance et al., *Lancet,* 2:997–1000 (1989)), inhibits platelet activation and adhesion (Radomski et al., *Br. J Pharmacol,* 92:181–187 (1987)), and nitric oxide limits the proliferation of vascular smooth muscle cells in vitro (Garg et al., *J. Clin. Invest.,* 83:1774–1777 (1986)). Similarly, in animal models, suppression of platelet-derived mitogens decreases intimal proliferation (Fems et al., *Science,* 253:1129–1132 (1991)). The potential importance of endothelium-derived nitric oxide in the control of arterial remodeling after injury is further supported by recent preliminary reports in humans suggesting that systemic NO donors reduce angiographic restenosis six months after balloon angioplasty (The ACCORD Study Investigators, *J. Am. Coil. Cardiol.* 23:59A. (Abstr.) (1994)).

Another aspect of restenosis may simply be mechanical, e.g., caused by the elastic rebound of the arterial wall and/or by dissections in the vessel wall caused by the angioplasty procedure. These mechanical problems have been successfully addressed by the use of stents to tack-up dissections and prevent elastic rebound of the vessel thereby reducing the level of reocclusion for many patients. The stent is typically inserted by catheter into a vascular lumen and expanded into contact with the diseased portion of the arterial wall, thereby providing internal support for the lumen. No material has, however, been developed that matches the blood-compatible surface of the endothelium. In fact, in the presence of blood and plasma proteins, artificial surfaces are an ideal setting for platelet deposition (Salzman et al, *Phil. Trans. R. Soc. Lond.,* B294:389–398 (1981)). Exposure of blood to an artificial surface initiates reactions that lead to clotting or platelet adhesion and aggregation. Within seconds of blood contact, the artificial surface becomes coated with a layer of plasma proteins which serves as a new surface to which platelets readily adhere, become activated, and greatly accelerate thrombus formation (Forbes et al, *Brit. Med. Bull.,* 34(2):201–207 (1978)).

Despite considerable efforts to develop nonthrombogenic materials, no synthetic material has been created that is free from this effect. In addition, the use of anticoagulant and platelet inhibition agents has been less than satisfactory in preventing adverse consequences resulting from the interaction between blood and artificial surfaces. Consequently, a significant need exists for the development of additional methods for preventing platelet deposition and thrombus formation on artificial surfaces.

There is a need in the art for effective methods of preventing and treating cardiovascular diseases and disorders, particularly, restenosis and atherosclerosis. The present invention is directed to these, as well as other, important ends.

SUMMARY OF THE INVENTION

The present invention describes novel nitrosated and/or nitrosylated taxanes and methods for preventing and/or treating cardiovascular diseases and disorders by administering one or more nitrosated and/or nitrosylated taxanes that are capable of releasing a therapeutically effective amount of nitric oxide to a targeted site effected by a cardiovascular disease or disorder. Preferably, the methods of the present invention are used for treating and/or preventing restenosis and atherosclerosis.

One embodiment of the present invention provides novel nitrosated and/or nitrosylated taxanes. The taxanes can be nitrosated and/or nitrosylated through one or more sites such as oxygen (hydroxyl condensation), sulfur (sulfhydryl condensation) and/or nitrogen. The present invention also provides compositions comprising a therapeutically effective amount of such compounds in a pharmaceutically acceptable carrier.

Another embodiment of the present invention provides compositions comprising a therapeutically effective amount of at least one taxane, that is optionally substituted with at least one NO and/or $NO_2$ group (i.e., nitrosylated and/or nitrosated), and at least one compound that donates, transfers or releases nitrogen monoxide as a charged species, i.e., nitrosonium (NO$^+$) or nitroxyl (NO−), or as the neutral species, nitric oxide (NO•), and/or stimulates endogenous production of nitric oxide or EDRF in vivo and/or is a substrate for nitric oxide synthase. The present invention also provides for such compositions in a pharmaceutically acceptable carrier.

Yet another embodiment of the present invention provides compositions comprising a therapeutically effective amount of at least one taxane, that is optionally substituted with at least one NO and/or NO$_2$ group (i.e., nitrosylated and/or nitrosated), at least one therapeutic agent, and, optionally, at least one compound that donates, transfers or releases nitrogen monoxide as a charged species, i.e., nitrosonium (NO$^+$) or nitroxyl (NO−), or as the neutral species, nitric oxide (NO•), and/or stimulates endogenous production of nitric oxide or EDRF in vivo and/or is a substrate for nitric oxide synthase. The invention also provides for such compositions in a pharmaceutically acceptable carrier.

Another embodiment of the present invention describes compositions and methods for making compositions comprising at least one taxane, that is optionally substituted with at least one NO and/or NO$_2$ group (i.e., nitrosylated and/or nitrosated), and, optionally, at least one compound that donates, transfers or releases nitric oxide and/or stimulates endogenous production of nitric oxide or EDRF in vivo and/or is a substrate for nitric oxide synthase and/or at least one therapeutic agent, that are bound to a natural or synthetic matrix, which can be applied with specificity to a biological site of interest. For example, the matrix containing the nitrosated and/or nitrosylated taxane can be used to coat the surface of a medical device or instrument that comes into contact with blood (including blood components, blood products and the like) or vascular tissue.

Yet another embodiment of the present invention provides methods for treating and/or preventing cardiovascular diseases and disorders, by administering to a patient in need thereof a therapeutically effective amount of at least one nitrosated and/or nitrosylated taxane and, optionally, at least one compound that donates, transfers or releases nitric oxide as a charged species, i.e., nitrosonium (NO$^+$) or nitroxyl (NO−), or as the neutral species, nitric oxide (NO•), and/or stimulates endogenous production of nitric oxide or EDRF in vivo and/or is a substrate for nitric oxide synthase. The methods can further comprise administering a therapeutically effective amount of at least one therapeutic agent. Alternatively, the methods for treating and/or preventing cardiovascular diseases and disorders, can comprise administering a therapeutically effective amount of at least one nitrosated and/or nitrosylated taxane, at least one therapeutic agent, and, optionally, at least one compound that donates, transfers or releases nitric oxide as a charged species, i.e., nitrosonium (NO$^+$) or nitroxyl (NO−), or as the neutral species, nitric oxide (NO•), and/or stimulates endogenous production of nitric oxide or EDRF in vivo and/or is a substrate for nitric oxide synthase. The nitrosated and/or nitrosylated taxanes, nitric oxide donors, and/or therapeutic agents can be administered separately or as components of the same composition in one or more pharmaceutically acceptable carriers.

The present invention also provides methods for treating and/or preventing cardiovascular diseases and disorders by administering to a patient in need thereof a therapeutically effective amount of at least one taxane and at least one compound that donates, transfers or releases nitric oxide as a charged species, i.e., nitrosonium (NO$^+$) or nitroxyl (NO−), or as the neutral species, nitric oxide (NO•), and/or stimulates endogenous production of nitric oxide or EDRF in vivo and/or is a substrate for nitric oxide synthase. The methods can further comprise administering a therapeutically effective amount of at least one therapeutic agent. Alternatively, the methods for treating and/or preventing cardiovascular diseases and disorders, can comprise administering a therapeutically effective amount of at least one taxane, at least one therapeutic agent, and, optionally, at least one compound that donates, transfers or releases nitric oxide as a charged species, i.e., nitrosonium (NO$^+$) or nitroxyl (NO−), or as the neutral species, nitric oxide (NO•), and/or stimulates endogenous production of nitric oxide or EDRF in vivo and/or is a substrate for nitric oxide synthase. The taxanes, the nitric oxide donors, and the therapeutic agents can be administered separately or as components of the same composition in one or more pharmaceutically acceptable carriers.

Yet another embodiment of the present invention describes methods for the prevention of platelet aggregation and platelet adhesion caused by the exposure of blood to a medical device or instrument by incorporating at least one nitrosated and/or nitrosylated taxane that is capable of releasing a therapeutically effective amount of nitric oxide into and/or on the portion(s) of the medical device that come into contact with blood (including blood components and blood products) or vascular tissue. The methods can further comprise incorporating at least one compound that donates, transfers or releases nitric oxide, and/or stimulates endogenous production of nitric oxide or EDRF in vivo and/or is a substrate for nitric oxide synthase, and, optionally, at least one therapeutic agent into and/or on the portion(s) of the medical device that come into contact with blood or vascular tissue. Alternatively the methods can comprise incorporating at least one taxane and at least one NO donor, and, optionally, at least one therapeutic agent.

Another embodiment of the invention relates to the local administration of at least one taxane, that is optionally substituted with at least one NO and/or NO$_2$ group, and, optionally, at least one therapeutic agent and/or at least one nitric oxide donor, to treat injured tissue, such as damaged blood vessels.

The present invention also provides methods using the compounds and compositions described herein to prevent or treat autoimmune diseases, pathological conditions resulting from abnormal cell proliferation, polycystic kidney disease, inflammatory diseases, to preserve organs and/or tissues, or to inhibit wound contraction, by administering to a patient in need thereof a therapeutically effective amount of at least one of the compounds and/or compositions described herein. In these methods, the taxanes that are optionally nitrosated and/or nitrosylated, nitric oxide donors and therapeutic agents can be administered separately or as components of the same composition in one or more pharmaceutically acceptable carriers.

These and other aspects of the present invention are described in detail herein.

BRIEF DESCRIPTION OF THE DRAWINGS

FIG. 3 is a dose response curve of human coronary artery smooth muscle cells for the compound of paclitaxel (open squares), Example 3 (open triangles, nitrosated paclitaxel derivative) and Example 4 (open inverted triangles, nitrosated paclitaxel derivative).

DETAILED DESCRIPTION OF THE INVENTION

Figure 1:
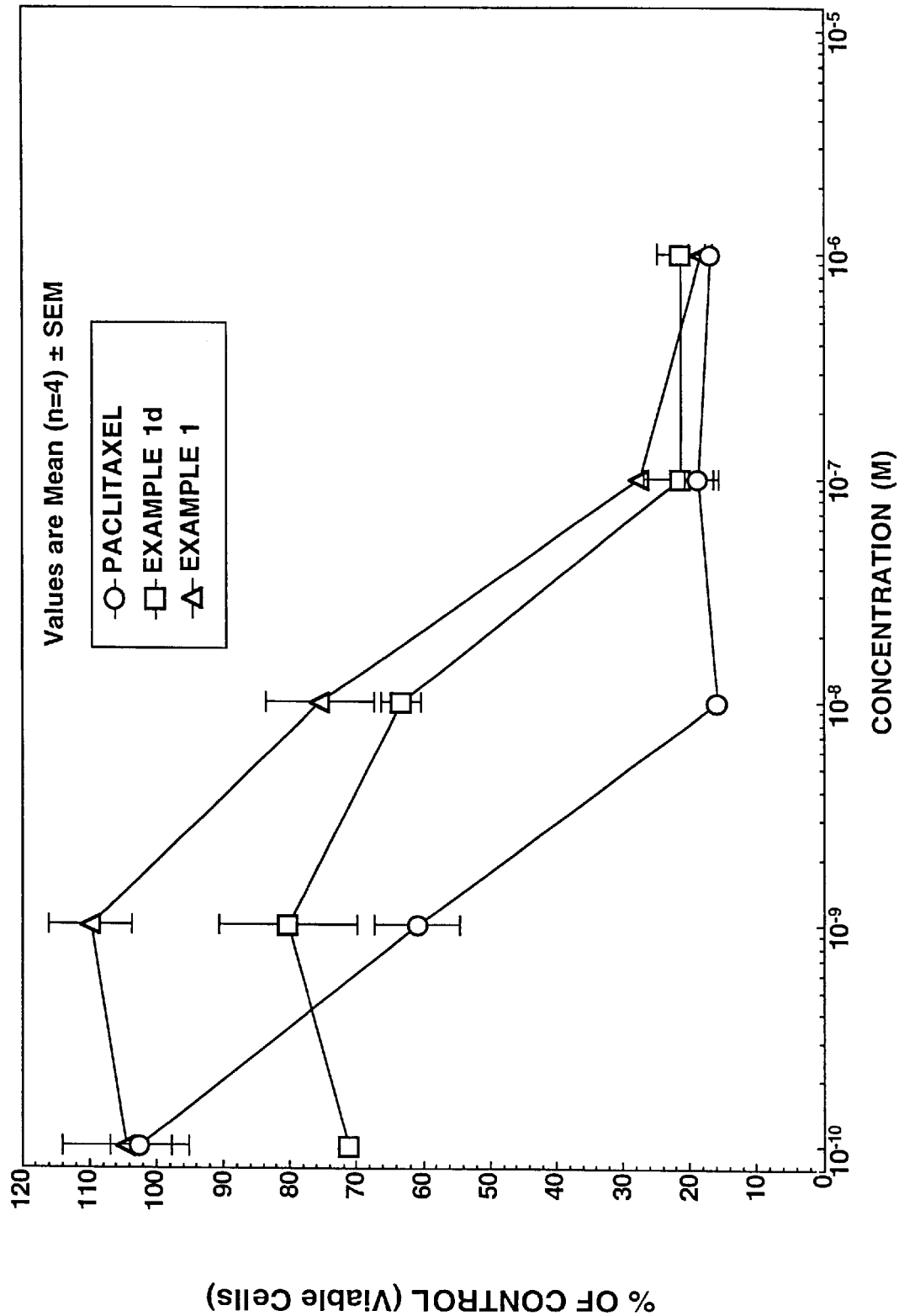
FIG. 1 is a dose response curve of human coronary artery smooth muscle cells for the compound of paclitaxel (open circles), Example 1 (open triangles, nitrosylated paclitaxel derivative) and Example 1d (open squares, sulfhydryl paclitaxel derivative).

As used throughout the disclosure, the following terms, unless otherwise indicated, shall be understood to have the following meanings.

"Taxane" refers to any compound that contains the carbon core framework represented by formula A:

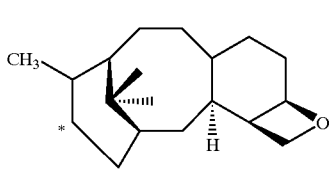

A

"Cardiovascular disease or disorder" refers to any cardiovascular disease or disorder known in the art, including, but not limited to, restenosis, atherosclerosis, atherogenesis, angina, (particularly chronic, stable angina pectoris), ischemic disease, congestive heart failure or pulmonary edema associated with acute myocardial infarction, thrombosis, controlling blood pressure in hypertension (especially hypertension associated with cardiovascular surgical procedures), platelet aggregation, platelet adhesion, smooth muscle cell proliferation, vascular complications associated with the use of medical devices, wounds associated with the use of medical devices, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, pulmonary thromboembolism, cerebral thromboembolism, thrombophlebitis, thrombocytopenia, bleeding disorders and/or any other complications which occur either directly or indirectly as a result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. For these angioplasty procedures, restenosis occurs at a rate of about 30–60% depending upon the vessel location, lesion length and a number of other variables. Restenosis can also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery.

"Inflammatory diseases" refers to any inflammatory disease or disorder known in the art whether of a chronic or acute nature, including, but not limited to, rheumatoid arthritis, inflammatory skin diseases, such as, psoriasis and eczema, restenosis, multiple sclerosis, surgical adhesion, tuberculosis, inflammatory lung diseases such as asthma, pneumoconiosis, chronic obstructive pulmonary disease, nasal polyps and pulmonary fibrosis, inflammatory bowel disease, such as, Crohn's disease and ulcerative colitis, graft rejections, inflammatory diseases that affect or cause obstruction of a body passageway, such as, vasculitis, Wegener's granulomatosis and Kawasaki disease, systemic lupus erthematosus, inflammation of the eye, nose or throat, such as, neovascular diseases of the eye including neovascular glaucoma, proliferative diabetic retinopathy, retrolental fibroblasia, mascular degeneration, reduction of intraocular pressure, corneal neovascularization, such as, corneal infections, immunological processes, such as, graft rejection and Steven-Johnson's syndrome, alkali burns, trauma and inflammation (of any cause). A description of inflammatory diseases can also be found in WO 98/24427, WO 99/62510 and U.S. Pat. No. 5,886,026, the disclosures of each of which are incorporated herein in their entirety.

"Pathological conditions resulting from abnormal cell proliferation" refers to any abnormal cellular proliferation of malignant or non-malignant cells in various tissues and/or organs, including but not limited to, muscle, bone, conjunctive tissues, skin, brain, lungs, sexual organs, lymphatic system, renal system, mammary cells, blood cells, liver, the digestive system, pancreas, thyroid, adrenal glands and the like. These pathological conditions can also include psoriasis; solid tumors; ovarian, breast, brain, prostate, colon, osesophageal, lung, stomach, kidney and/or testicular cancer; Karposi's sarcoma, cholangiocarcinoma; choriocarcinoma; neoblastoma; Wilm's tumor; Hodgkin's disease; melanomas; multiple myelomas; chronic lymphocytic leukemias, and acute or chronic granulocytic lymphomas.

"Artificial surface" refers to any synthetic material contained in a device or apparatus that is in contact with blood, vasculature or other tissues.

"Blood" includes blood products, blood components and the like.

"Platelet adhesion" refers to the contact of a platelet with a foreign surface, including any artificial surface, such as a medical device or instrument, as well as an injured vascular surfaces, such as collagen. Platelet adhesion does not require platelet activation. Unactivated, circulating platelets will adhere to injured vascular surfaces or artificial surfaces via binding interactions between circulating von Willdebrand factor and platelet surface glycoprotein Ib/IX.

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Passivation" refers to the coating of a surface which renders the surface non-reactive.

"Platelet activation" refers either to the change in conformation (shape) of a cell, expression of cell surface proteins (e.g., the IIb/IIa receptor complex, loss of GPIb surface protein), and secretion of platelet derived factors (e.g., serotonin, growth factors).

"Patient" refers to animals, preferably mammals, more preferably humans, and includes children and adults.

"Therapeutically effective amount" refers to the amount of the compound and/or composition that is effective to achieve its intended purpose.

"Medical device" refers to any intravascular or extravascular medical devices, medical instruments, foreign bodies and the like. Examples of intravascular medical devices and instruments include balloons or catheter tips adapted for insertion, prosthetic heart valves, sutures, synthetic vessel grafts, stents (e.g. Palmaz-Schatz stent, esophageal stent, colonic stent, vascular stent, urethral stent, and the like), drug pumps, arteriovenous shunts, artificial heart valves, artificial implants, foreign bodies introduced surgically into the blood vessels or at vascular sites, leads, pacemakers, implantable pulse generators, implantable cardiac defibrillators, cardioverter defibrillators, defibrillators, spinal stimulators, brain stimulators, sacral nerve stimulators, chemical sensors, and the like. Examples of extravascular medical devices and instruments include plastic tubing, dialysis bags or membranes whose surfaces come in contact with the blood stream of a patient.

"Prodrug" refers to a compound that is made more active in vivo.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO\bullet$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO–, $NO\bullet$), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethylbutyn-1yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0) octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated, unsaturated, cyclic or aromatic or polycyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. Exemplary heterocyclic groups include pyrrolyl, 3-pyrrolinyl-4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicyclo(3,3,0)octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, halo, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Alkylcycloalkyl" refers to a cycloalkyl radical, as defined herein, attached to an alkyl radical, as defined herein. Exemplary alkylcycloalkyl groups include cyclohexylmethyl, 2-cyclopentenylmethyl and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl and the like.

"Cycloalkenyl" refers to an unsaturated cyclic hydrocarbon having about 3 to about 10 carbon atoms (preferably about 3 to about 8 carbon atoms, more preferably about 3 to about 6 carbon atoms) comprising one or more carbon-carbon double bonds.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetrahydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Aryloxy" refers to $R_{55}O$—, wherein $R_{55}$ is an aryl group, as defined herein. Exemplary aryloxy groups include napthyloxy, quinolyloxy, isoquinolizinyloxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to —O⁻$R_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Amino" refers to —$NH_2$.

"Nitrate" refers to —O—$NO_2$.

"Nitrite" refers to —O—NO.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{50}R_{52}N$—, wherein $R_{50}$ and $R_{52}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino" refers to $R_{50}R_{55}N$—, wherein $R_{50}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to —$S(O)_2^-$.

"Sulfonic acid" refers to —$S(O)_2OR_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —S(O)$_2$OR$_{58}$, wherein R$_{58}$ is an alkyl group, an aryl group, an alkylaryl group or an aryl heterocyclic ring, as defined herein.

"Sulfonamido" refers to —S(O)$_2$—N(R$_{51}$)(R$_{57}$), wherein R$_{51}$ and R$_{57}$ are each independently a hydrogen atom, an alkyl group, an aryl group, an alkylaryl group, or an arylheterocyclic ring, as defined herein, or R$_{51}$ and R$_{57}$ taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to R$_{50}$S—, wherein R$_{50}$ is an alkyl group, as defined herein.

"Arylthio" refers to R$_{55}$S—, wherein R$_{55}$ is an aryl group, as defined herein.

"Cycloalkylthio" refers to R$_{54}$S—, wherein R$_{54}$ is a cycloalkyl group or a bridged cycloalkyl group, as defined herein. Exemplary cycloalkylthio groups include cyclopropylthio, cyclopentylthio, cyclohexylthio, and the like.

"Alkylsulfinyl" refers to R$_{50}$—S(O)—, wherein R$_{50}$ is an alkyl group, as defined herein.

"Alkylsulfonyl" refers to R$_{50}$—S(O)$_2$—, wherein R$_{50}$ is an alkyl group, as defined herein.

"Arylsulfinyl" refers to R$_{55}$—S(O)—, wherein R$_{55}$ is an aryl group, as defined herein.

"Arylsulfonyl" refers to R$_{55}$—S(O)$_2$—, wherein R$_{55}$ is an aryl group, as defined herein.

"Amidyl" refers to R$_{51}$C(O)N(R$_{57}$)— wherein R$_{51}$ and R$_{57}$ are each independently a hydrogen atom, an alkyl group, an aryl group, an alkylaryl group, or an arylheterocyclic ring, as defined herein.

"Ester" refers to R$_{51}$C(O)O— wherein R$_{51}$ is a hydrogen atom, an alkyl group, an aryl group, an alkylaryl group, or an arylheterocyclic ring, as defined herein.

"Carbamoyl" refers to —O—C(O)N(R$_{51}$)(R$_{57}$), wherein R$_{51}$ and R$_{57}$ are each independently a hydrogen atom, an alkyl group, an aryl group, an alkylaryl group or an arylheterocyclic ring, as defined herein, or R$_{51}$ and R$_{57}$ taken together are a heterocyclic ring, a cycloalkyl group or a bridged cycloalkyl group, as defined herein.

"Carbamate" refers to —R$_{51}$O—C(O)N(R$_{57}$), wherein R$_{51}$ and R$_{57}$ are each independently a hydrogen atom, an alkyl group, an aryl group, an alkylaryl group or an arylheterocyclic ring, as defined herein, or R$_{51}$ and R$_{57}$ taken together are a heterocyclic ring, a cycloalkyl group or a bridged cycloalkyl group, as defined herein.

"Carboxyl" refers to —C(O)OR$_{76}$, wherein R$_{76}$ is a hydrogen, an organic cation or an inorganic cation, as defined herein.

"Carbonyl" refers to —C(O)—.

"Alkylcarbonyl" or "alkanoyl" refers to R$_{50}$—C(O)—, wherein R$_{50}$ is an alkyl group, as defined herein.

"Arylcarbonyl" or "aroyl" refers to R$_{55}$—C(O)—, wherein R$_{55}$ is an aryl group, as defined herein.

"Carboxylic ester" refers to —C(O)OR$_{58}$, wherein R$_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N(R$_{51}$)(R$_{57}$), wherein R$_{51}$ and R$_{57}$ are each independently a hydrogen atom, an alkyl group, an aryl group, an alkylaryl group or an arylheterocyclic ring, as defined herein, or R$_{51}$ and R$_{57}$ taken together with the nitrogen to which they are attached form a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N(R$_{59}$)—C(O)N(R$_{51}$)(R$_{57}$) wherein R$_{51}$, R$_{57}$, and R$_{59}$ are each independently a hydrogen atom, an alkyl group, an aryl group, an alkylaryl group, or an arylheterocyclic ring, as defined herein, or R$_{51}$ and R$_{57}$ taken together with the nitrogen to which they are attached form a heterocyclic ring, as defined herein.

"Phosphoryl" refers to —P(R$_{70}$)(R$_{71}$)(R$_{72}$), wherein R$_{70}$ is a lone pair of electrons, sulfur or oxygen, and R$_{71}$ and R$_{72}$ are each independently a covalent bond, a hydrogen, a lower alkyl, an alkoxy, an alkylamino, a hydroxy or an aryl, as defined herein.

"Silyl" refers to —Si(R$_{73}$)(R$_{74}$)(R$_{75}$), wherein R$_{73}$, R$_{74}$ and R$_{75}$ are each independently a covalent bond, a lower alkyl, an alkoxy, an aryl or an arylalkoxy, as defined herein.

The present invention is directed to the treatment and/or prevention of cardiovascular diseases and disorders in patients by administering one or more taxanes that are linked (directly or indirectly) to one or more nitric oxide adducts. Preferably, the taxanes that are linked to one or more nitric oxide adducts are administered in the form of a pharmaceutical composition that further comprises a pharmaceutically acceptable carrier or diluent. The novel compounds and novel compositions of the present invention are described in more detail herein.

Taxanes that may be used in the present invention include, for example, paclitaxel and docetaxel. Paclitaxel is a naturally occurring taxane diterpenoid which is found in the bark of several species of the yew tree such as *Taxus brefifolia*, genus Taxus, family Taxaceae. Paclitaxel is known in the literature as taxol and a pharmaceutical composition of which is known as TAXOL®, a registered trademark of the Bristol-Myers Squibb Company, Princeton, N.J. Docetaxel is a semi-synthetic analog of paclitaxel and is sold under the trademark TAXOTERE® by Rhone-Poulene Rorer, Vitry-sur-Seine, France. The structures of TAXOL® and TAXOTERE® are shown below:

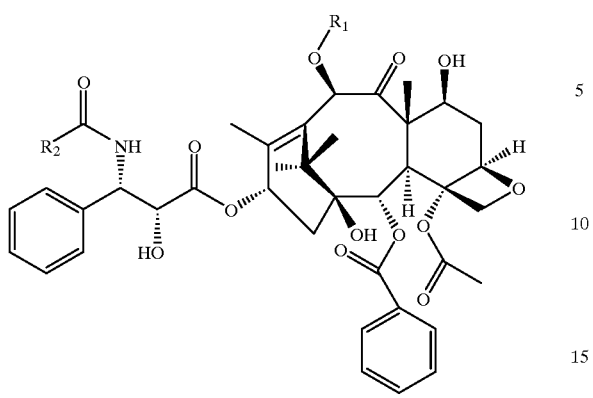

TAXOL®: R₁=acetyl, R₂=C₆H₅
TAXOTERE®: R₁=hydrogen, R₂=t-butoxy

Other contemplated taxanes for use in the present invention include all those known in the art and include those described herein, such as, for example, water soluble compositions of paclitaxel and docetaxel, pro-drugs of paclitaxel and docetaxel, as well as functional analogs, equivalents or derivatives of taxanes. For example, derivatives and analogs of taxanes include, but are not limited to, baccatin III, 10-deacetyltaxol, 7-xylosyl-10-deacetyltaxol, cephalomannine, 10-deacetyl-7-epitaxol, 7-epitaxol, 10-deacetylbaccatin III, 10-deacetyl cephaolmannine and analogs or derivatives, and the like. Taxanes are disclosed in, for example, U.S. Pat. Nos. 4,960,790, 5,157,049, 5,284,864, 5,399,726, 5,550,261, 5,616,608, 5,629,433, 5,646,176, 5,688,977, 5,703,117, 5,760,072, 5,808,113, 5,912,263, 5,919,815, 5,965,739, 5,977,163, 5,981,564, 5,998,656, 6,017,935, 6,017,948, 6,028,205 and in WO 93/17121, WO 94/15599, WO 95/20582, WO 96/00724, WO 96/40091, WO 97/10234, WO 97/19938, WO 97/32578, WO 97/33552, WO 98/00419, WO 98/28288, WO 98/37765, WO 98/38862, WO 99/14209, WO 99/49901, WO 99/57105, WO 00/10988 and in EP 0 558 959 B1, EP 0 624 377 A2, EP 0 639 577 A1, the disclosures of each of which are incorporated by reference herein in their entirety.

In one embodiment, the present invention describes nitrosated and/or nitrosylated taxanes and pharmaceutically acceptable salts thereof of Formula (I);

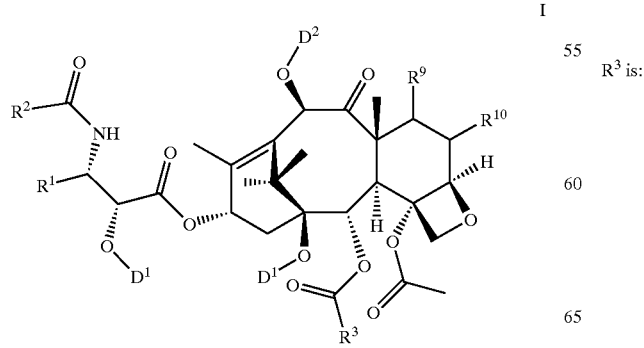

I wherein:
$R^1$ is:

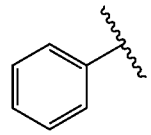  (a)

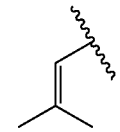  (b)

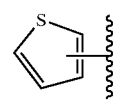  (c)

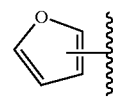  (d)

or

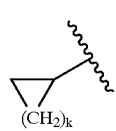  (e)

$R^2$ is:

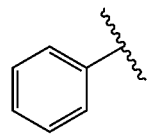  (a)

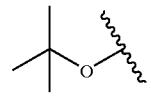  (b)

or

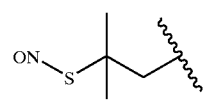  (c)

$R^3$ is:

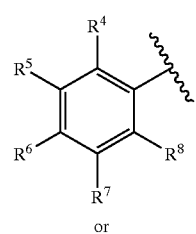  (a)

or (b)

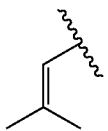

$R^4$, $R^5$, $R^6$, $R^7$ and $R^8$ are each independently a hydrogen, a lower alkyl group, an alkenyl, an alkynyl, an alkoxy, a halo, a haloalkyl, a nitro or an amino;

$R^9$ and $R^{10}$ are each independently a hydrogen, —$OD^1$, —$SD^1$ or a halo;

$D^1$ is a hydrogen or D;

$D^2$ is a hydrogen, —C(O)CH$_3$ or D;

D is Q or K;

Q is —NO or —NO$_2$;

K is —$W_a$—$E_b$—$(C(R_e)(R_f))_p$—$E_c$—$(C(R_e)(R_f))_x$—$W_d$—$(C(R_e)(R_f))_y$—$W_i$—$E_j$—$W_g$—$(C(R_e)(R_f))_z$—T—Q;

a, b, c, d, g, i and j are each independently an integer from 0 to 3;

p, x, y and z are each independently an integer from 0 to 10;

W at each occurrence is independently —C(O), —C(S), —T, —$(C(R_e)(R_f))_h$, an alkyl group, an aryl group, a heterocyclic ring, an arylheterocyclic ring, or —$(CH_2CH_2O)_q$;

E at each occurrence is independently —T—, an alkyl group, an aryl group, —$(C(R_e)(R_f))_h$, a heterocyclic ring, an arylheterocyclic ring, or —$(CH_2CH_2O)_q$;

h is an integer form 1 to 10;

q is an integer from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a urea, a phosphoryl, a nitro, $W_h$, —T—Q , or —$(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group;

k is an integer from 1 to 3;

T at each occurrence is independently a covalent bond, a carbonyl, an oxygen, —S(O)$_o$ or —N($R_e$)$R_i$;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T—Q)($R_e$)($R_f$), or —(N$_2$O$_2$—)$^-$•M$^+$, wherein M$^+$ is an organic or inorganic cation;

with the proviso that the compounds of Formula (I) must contain at least one nitrite, nitrate, thionitrite or thionitrate group.

In cases where $R_e$ and $R_f$ are a heterocyclic ring or taken together $R_e$ and $R_f$ are a heterocyclic ring, then $R_i$ can be a substituent on any disubstituted nitrogen contained within the radical where $R_i$ is as defined herein.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E—E) and $(C(R_e)(R_f))_2$ denotes —C($R_e$)($R_f$)—C($R_e$)($R_f$)—, where $R_e$ and $R_f$ at each occurrence are each independently selected from those moieties defined herein.

In a preferred embodiment the compounds of Formula (I) do not include the compounds in which:

—$OD^1$ and —$OD^2$ are each independently —O—NO$_2$;

$R^9$ is —O—NO$_2$ or the $D^1$ group at $R^9$ contains a nitroaryl group or a nitroxyloside group;

$R^{10}$ is —O—NO$_2$

These compounds contain a nitroaryl group or a nitroxyloside group or are compounds in which the nitro group is directly attached to the taxane structure as disclosed in WO 96/40091, WO 96/00724 and WO 98/38862 and in *Tetrahedron Letters*, 39:4611–4614 (1998).

Compounds of the present invention which have one or more asymmetric carbon atoms can exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

The parent taxane compound can be synthesized by one skilled in the art following the methods described herein, and by the methods described in, for example, U.S. Pat. Nos. 4,960,790, 5,157,049, 5,284,864, 5,399,726, 5,550,261, 5,616,608, 5,629,433, 5,646,176, 5,688,977, 5,703,117, 5,760,072, 5,808,113, 5,912,263, 5,919,815, 5,965,739, 5,977,163, 5,981,564, 5,998,656, 6,017,935, 6,017,948, 6,028,205, 6,147,234, 6,177,456 and in WO 94/15599, WO 95/20582, WO 96/00724, WO 96/40091, WO 97/10234, WO 97/19938, WO 97/32578, WO 97/33552, WO 98/00419, WO 98/28288, WO 98/37765, WO 98/38862, WO 99/02648, WO 99/14209, WO 99/31079, WO 99/49901, WO 99/57105, WO 00/10988, WO 00/35896 and in EP 0 558 959 B1, EP 0 624 377 A2, EP 0 639 577 A1 the disclosure of each of these patents and applications is incorporated by reference herein in its entirety.

The compounds of formula (I) can be synthesized following the methods described herein. The reactions are performed in solvents appropriate to the reagents, and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is known in the art for protecting thiol and alcohol groups against undesirable reactions during a synthetic procedure and many such protecting groups are known, e.g., T. H. Greene and P. G. M. Wuts, *Protective Groups in Organic Synthesis,* John Wiley & Sons, New York (1999), which is incorporated herein in its entirety.

Some of the compounds of the invention are synthesized as shown in Schemes 1 through 9 presented below, in which D, $D^1$, $D^2$, E, K, Q, T, W, $R^1$, $R^2$, $R^3$, $R^4$, $R^5$, $R^6$, $R^7$, $R^8$, $R^9$, $R^{10}$, $R_e$, $R_f$, $R_a$, $R_i$, a, b, c, d, g, h, i, j, k, o, p, q, x, y and z are as defined herein or as depicted in the reaction schemes for structure I; $P^1$ is an oxygen protecting group, $P^2$ is a sulfur protecting group; and $A_1$, $A_2$ and $A_3$ are each independently chosen as a lower alkyl group or a phenyl group. Nitroso compounds of formula (I) wherein $R^1$, $R^2$, $R^3$, $A_1$, $A_2$ and $A_3$ are as defined herein, $D^1$ is a hydrogen or a nitroso group, $D^2$ is an acetate, $R^{10}$ is a hydrogen and a nitrite is representative of the $R^9$ group as defined herein, may be prepared as shown in Scheme 1. The 2'-hydroxy group of formula 1 is converted to the trialkylsilyloxy group of formula 2 by reaction with silyl chloride and an amine in an inert solvent. Preferred methods for the preparation of silyloxy groups are reacting the alcohol with triethylsilyl-chloride in the presence of pyridine in an anhydrous inert solvent, such as dichloromethane, at 0° C., or reacting tert-butyldimethylsilylchloride in the presence of imidazole in an anhydrous inert solvent, such as DMF, at 60° C. The compound of the formula 2 is then converted to the compound of the formula 3 by reaction with a suitable nitrosylating agent, such as thionyl chloride nitrite, thionyl dinitrite, or nitrosium tetrafluoroborate, in a suitable anhydrous solvent, such as methylene chloride, THF, DMF or acetonitrile, with or without an amine base, such as pyridine or triethylamine. Deprotection of the 2'-hydroxyl moiety (fluoride ion or aqueous acid are the preferred methods for removing silyl ether protecting groups) produces the compounds of the formula IA.

Scheme 1

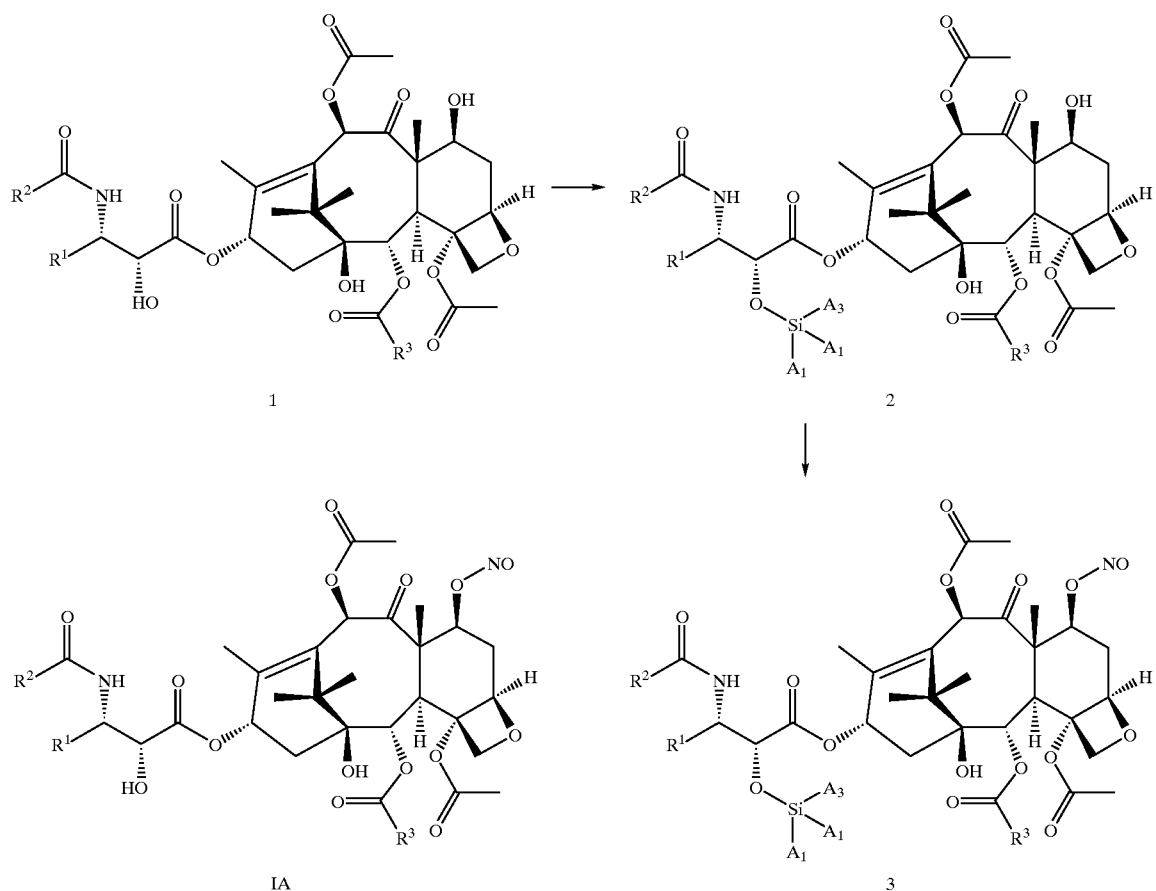

Nitroso compounds of formula (I) wherein $R^1$, $R^2$, and $R^3$ are as defined herein, $D^1$ is a hydrogen or a nitroso group, $D^2$ is an acetate, $R^{10}$ is a hydrogen and a nitrite is representative of the $R^9$ group as defined herein, may be prepared as outlined in Scheme 2. The compound of the formula 1 is converted to the compound of the formula IB by reaction with a suitable nitrosylating agent, such as thionyl chloride nitrite, thionyl dinitrite, or nitrosium tetrafluoroborate, in a suitable anhydrous solvent, such as methylene chloride, THF, DMF or acetonitrile, with or without an amine base, such as pyridine or triethylamine.

Scheme 2

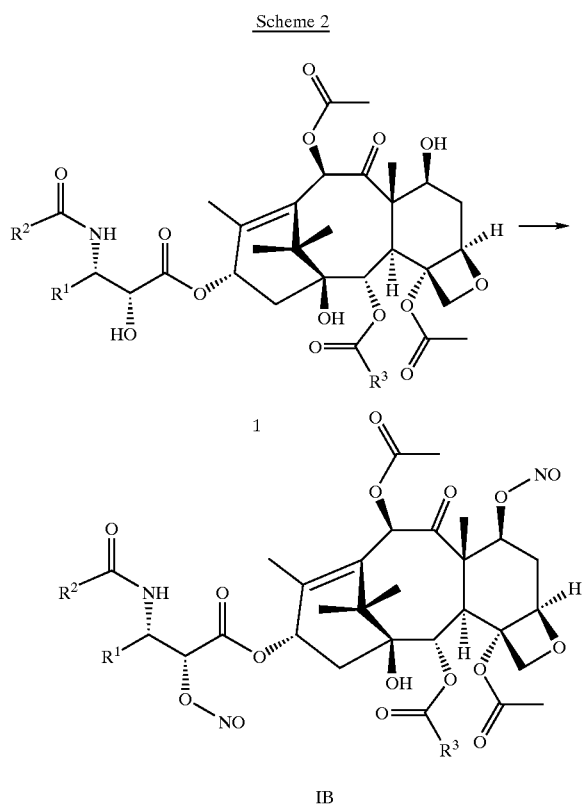

Nitroso compounds of formula (I) wherein $R^1, R^2, R^3, A_1, A_2$ and $A_3$ are as defined herein, $D^1$ is a hydrogen or a nitroso group, $D^2$ is an acetate, $R^{10}$ is a hydrogen and a nitrosothiol is representative of the $R^9$ group as defined herein, may be prepared as outlined in Scheme 3. The compound of the formula 2 is converted to the compound of the formula 4 by reacting the 7-hydroxyl group with trifluoromethansulfonyl chloride in the presence of 4-dimethylaminopyridine (DMAP) in an inert solvent, such as dichloromethane, at 0° C. to room temperature. The compound of the formula 4 is converted to the thiol of the formula 5 by displacing the triflate group with potassium thioacetate in anhydrous ethanol and then removing the acetate group by treating the intermediate with a saturated anhydrous ethanolic solution of ammonia. The compound of the formula 5 is then converted to the compound of the formula IC by first reaction with a suitable nitrosylating agent, such as thionyl chloride nitrite, thionyl dinitrite, or nitrosium tetrafluoroborate, in a suitable anhydrous solvent, such as methylene chloride, THF, DMF or acetonitrile, with or without an amine base, such as pyridine or triethylamine, followed by deprotection of the 2'-hydroxyl moiety (fluoride ion or aqueous acid are the preferred methods for removing silyl ether protecting groups) to produce the compound of the formula IC.

Scheme 3

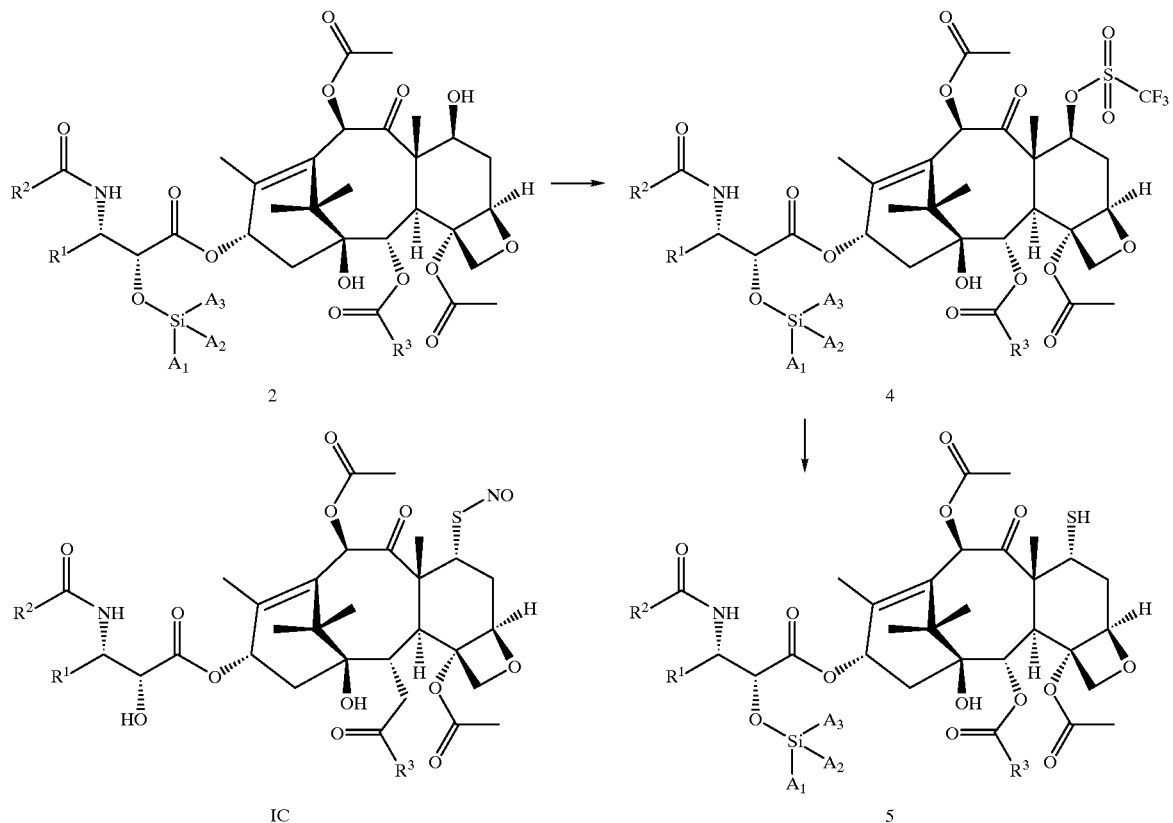

Nitroso compounds of formula (I) wherein $R^1$, $R^2$, $R^3$, $R_e$, $R_f$, a, b, c, d, g, i, j, p, v, x, z, $A_1$, $A_2$ and $A_3$ are as defined herein, $D^1$ is a hydrogen, $D^2$ is an acetate, $R^{10}$ is a hydrogen and a nitrite containing ester is representative of the $R^9$ group as defined herein, may be prepared as outlined in Scheme 4. The 7-hydroxyl group of the compound of formula 2 is converted to the ester of formula 6, wherein R is —$W_{a-1}$—$E_b$—$(C(R_e)(R_f))_p$—$E_c$—$(C(R_e)(R_f))_x$—$W_d$—$(C(R_e)(R_f))_y$—$W_i$—$E_j$—$W_g$—$(C(R_e)(R_f))_z$, by reaction with an appropriate protected alcohol containing active acylating agent, wherein $P^1$ is as defined herein. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF.

(DCC) or 1-ethyl-3 (3-dimethylaminopropyl) carbodiimide hydrochloride (EDAC .HCl) with a catalyst, such as DMAP or 1-hydroxybenzotriazole (HOBt). Preferred protecting groups for the alcohol moiety are as a benzyl ether or a benzyl carbonate. Deprotection of the hydroxyl moiety (hydrogenolysis using a palladium catalyst or electrolytic reduction are the preferred methods for removing benzyl ether and benzyl carbonate protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile with or without an amine base such as pyridine or triethylamine, affords the compound of the formula 7. Deprotection of the 2'-hydroxyl moiety (fluoride ion or aqueous acid are the preferred methods for removing silyl ether protecting groups) produces the compound of the formula ID.

Scheme 4

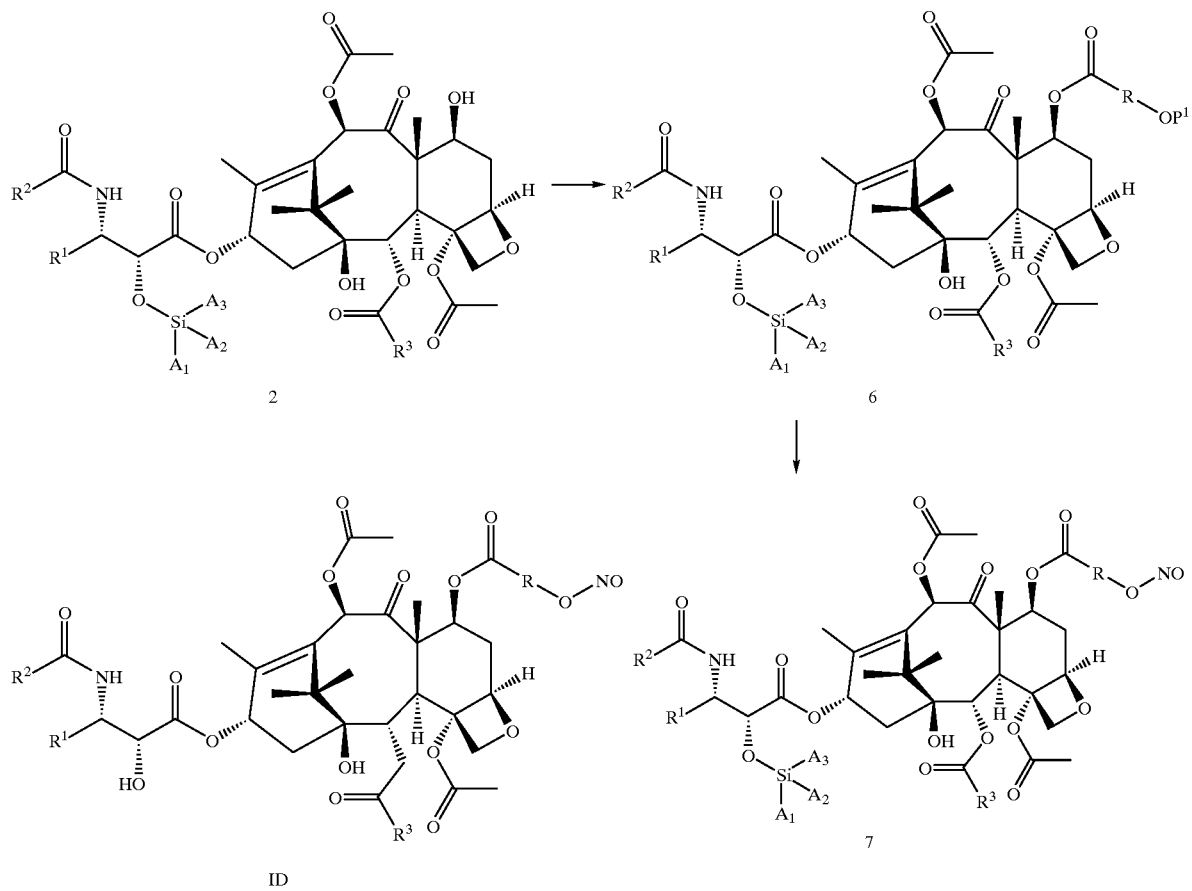

ID

The mixed anhydride is then reacted with the 7-hydroxyl, preferably in the presence of a condensation catalyst, such as DMAP. Alternatively, the acid may first be converted to the acid chloride by treatment with oxalyl chloride in the presence of a catalytic amount of DMF. The acid chloride is then reacted with the 7-hydroxyl, preferably in the presence of a condensation catalyst, such as DMAP, and a tertiary amine base, such as triethylamine, to produce the ester. Alternatively, the protected alcohol containing acid and 7-hydroxyl may be coupled to produce the ester by treatment with a dehydration agent, such as dicyclohexylcarbodiimide Nitroso compounds of formula (I) wherein R, $R^1$, $R^2$, $R^3$, $R_e$, $R_f$, a, b, c, d, g, i, j, p, v, x, z, K, $A_1$, $A_2$ and $A_3$ are as defined herein, $D^1$ is a hydrogen or a K group, $D^2$ is an acetate, $R^{10}$ is a hydrogen and a nitrite containing ester is representative of the $R^9$ group as defined herein, may be prepared as outlined in Scheme 5. The compound of formula 1 is converted to the diester of formula 8, wherein R is as defined herein, by reaction with an appropriate protected alcohol containing active acylating agent, wherein $P^1$ is as defined herein. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the 2'- and 7-hydroxyls, preferably in the presence of a condensation catalyst, such as DMAP. Alternatively, the acid may first be converted to the acid chloride by treatment with oxalyl chloride in the presence of a catalytic amount of DMF. The acid chloride is then reacted with the 2'- and 7-hydroxyls, preferably in the presence of a condensation catalyst, such as DMAP, and a tertiary amine base, such as triethylamine, to produce the diester. Alternatively, the protected alcohol containing acid and the 2'-and 7-hydroxyls may be coupled to produce the diester by treatment with a dehydration agent, such as DCC or EDAC .HCl with a catalyst such as DMAP or HOBt. Preferred protecting groups for the alcohol moieties are as benzyl ethers or benzyl carbonates. Deprotection of the hydroxyl moieties (hydrogenolysis using a palladium catalyst or electrolytic reduction are the preferred methods for removing benzyl ether and benzyl carbonate protecting groups) followed by reaction a suitable nitrosylating agent, such as thionyl chloride nitrite, thionyl dinitrite, or nitrosonium tetrafluoroborate in a suitable anhydrous solvent, such as dichloromethane, THF, DMF, or acetonitrile, with or without an amine base, such as pyridine or triethylamine, affords the compound of the formula IE.

Scheme 5

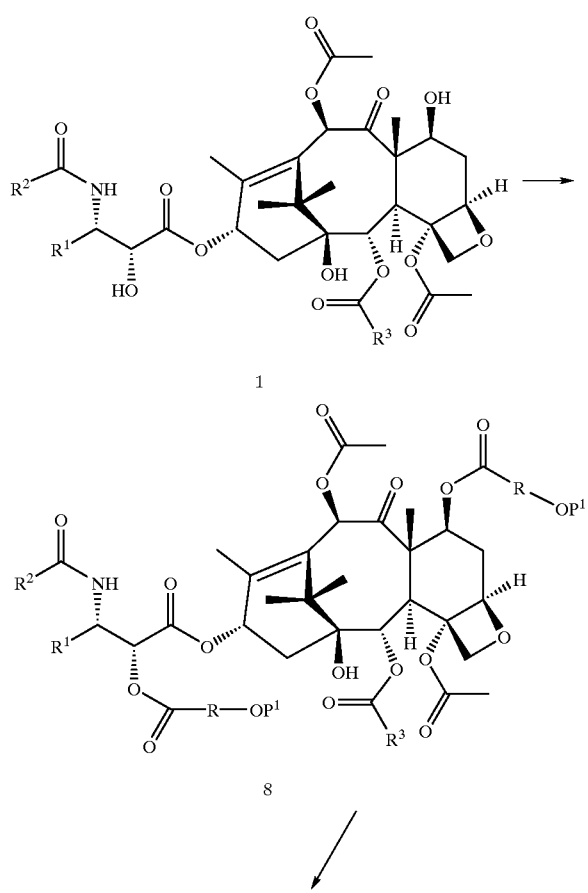

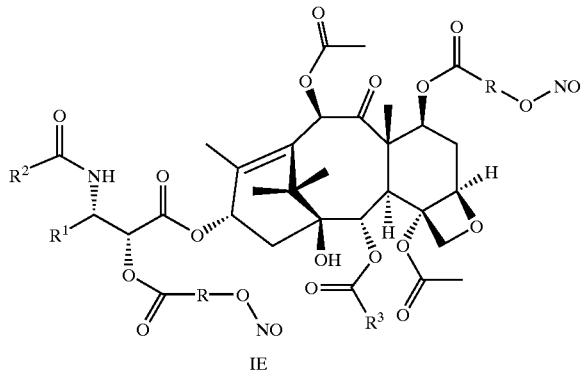

IE

Nitroso compounds of formula (I) wherein $R^1$, $R^2$, $R^3$, $R_e$, $R_f$, a, b, c, d, g, i, j, p, v, x, z, $A_1$, $A_2$ and $A_3$ are as defined herein, $D^1$ is a hydrogen, $D^2$ is an acetate, $R^{10}$ is a hydrogen and a nitrosothiol containing ester is representative of the $R^9$ group as defined herein, may be prepared as outlined in Scheme 6. The 7-hydroxyl group of the compound of formula 2 is converted to the ester of formula 9, wherein R is as defined herein, by reaction with an appropriate protected thiol containing active acylating agent, wherein $P^2$ is as defined herein. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the 7-hydroxyl, preferably in the presence of a condensation catalyst, such as DMAP. Alternatively, the acid may first be converted to the acid chloride by treatment with oxalyl chloride in the presence of a catalytic amount of DMF. The acid chloride is then reacted with the 7-hydroxyl, preferably in the presence of a condensation catalyst, such as DMAP, and a tertiary amine base, such as triethylamine, to produce the ester. Alternatively, the protected thiol containing acid and the 7-hydroxyl may be coupled to produce the ester by treatment with a dehydration agent, such as DCC or EDAC .HCl, with a catalyst, such as DMAP or HOBt. Preferred protecting groups for the thiol moiety are as a thioester, such as thioacetate or thiobenzoate, as a disulfide, as a thiocarbamate, such as N-methoxymethyl thiocarbamate, or as a thioether, such as paramethoxybenzyl thioether, a 2,4,6-trimethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters, and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as a lower alkyl nitrite, such as tert-butyl nitrite, in a suitable anhydrous solvent, such as methylene chloride, THF, DMF or acetonitrile, produces the compound of formula 10. Deprotection of the 2'-hydroxyl moiety (fluoride ion or aqueous acid are the preferred methods for removing silyl ether protecting groups) produces the compounds of the formula IF.

Scheme 6

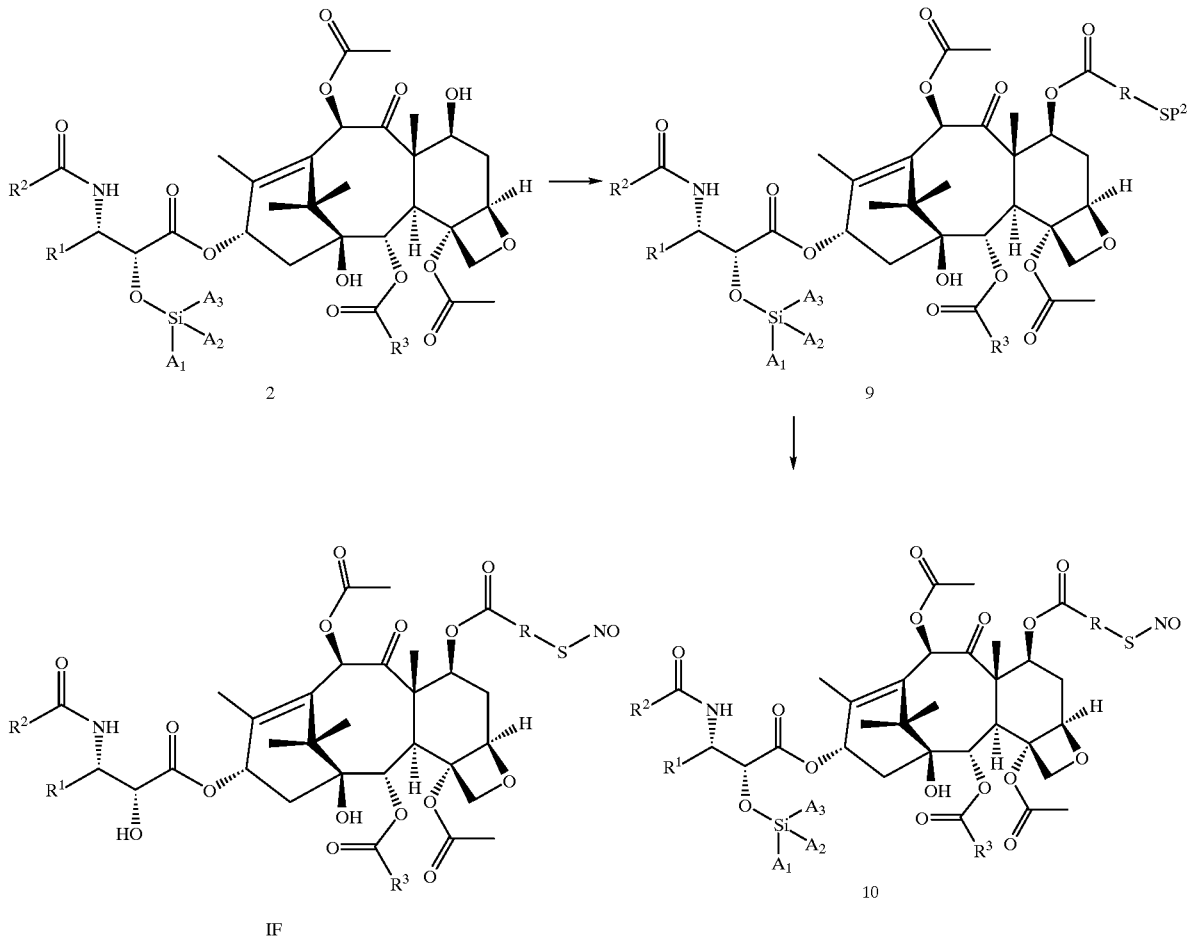

Nitroso compounds of formula (I) wherein R, $R^1$, $R^2$, $R^3$, $R_e$, $R_f$, a, b, c, d, g, i, j, p, v, x, z, K, $A_1$, $A_2$ and $A_3$ are as defined herein, $D^1$ is a hydrogen or a K group, $D^2$ is an acetate, $R^{10}$ is a hydrogen and a nitrosothiol containing ester is representative of the $R^9$ group as defined herein, may be prepared as outlined in Scheme 7. The compound of formula 1 is converted to the diester of formula 11, wherein R is as defined herein, by reaction with an appropriate protected thiol containing active acylating agent, wherein $P^2$ is as defined herein. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the 2'- and 7-hydroxyls, preferably in the presence of a condensation catalyst, such as DMAP. Alternatively, the acid may first be converted to the acid chloride by treatment with oxalyl chloride in the presence of a catalytic amount of DMF. The acid chloride is then reacted with the 2'- and 7-hydroxyls, preferably in the presence of a condensation catalyst, such as DMAP, and a tertiary amine base, such as triethylamine, to produce the diester. Alternatively, the protected thiol containing acid and the 2'- and 7-hydroxyls may be coupled to produce the diester by treatment with a dehydration agent, such as DCC or EDAC .HCl, with a catalyst, such as DMAP or HOBt. Preferred protecting groups for the thiol moieties are as a thioester, such as thioacetate or thiobenzoate, as disulfides, as thiocarbamates, such as N-methoxymethyl thiocarbamate, or as thioethers, such as paramethoxybenzyl thioether, a 2,4,6-trimethoxybenzyl thioether, a tetrahydropyranyl thioether, or a S-triphenylmethyl thioether. Deprotection of the thiol moieties (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a 2,4,6-trimethoxybenzyl thioether a tetrahydropyranyl thioether or a S-triphenylmethyl thioether group) followed by reaction with a suitable nitrosylating agent, such as a lower alkyl nitrite, such as tert-butyl nitrite, in a suitable anhydrous solvent, such as methylene chloride, THF, DMF or acetonitrile, produces the compound of formula IG.

Scheme 7

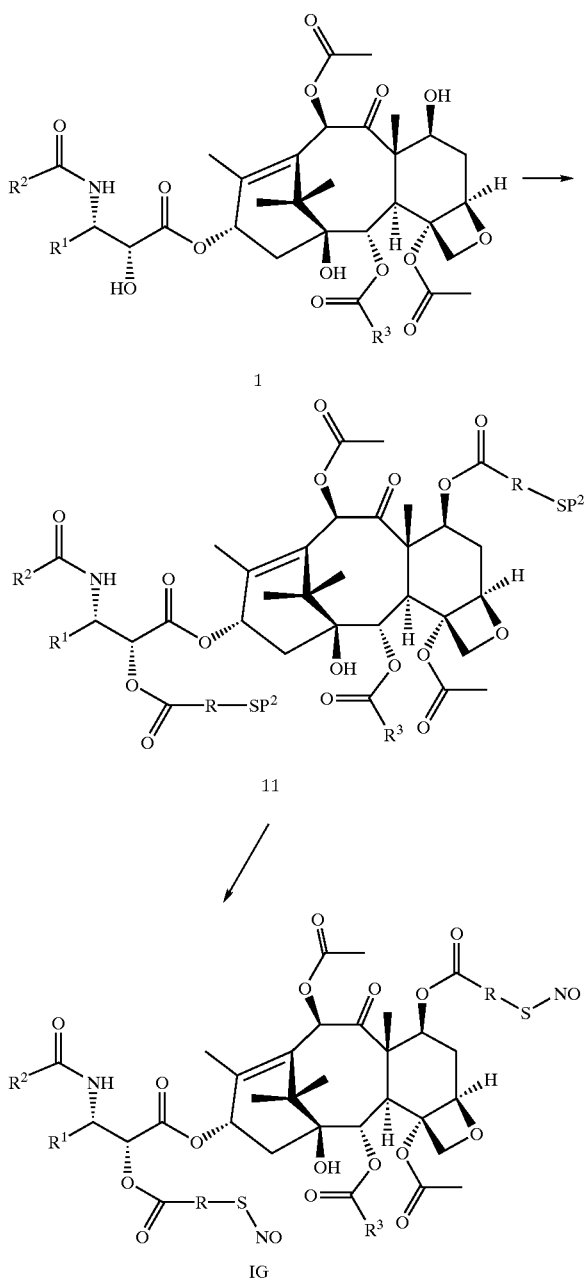

Scheme 8

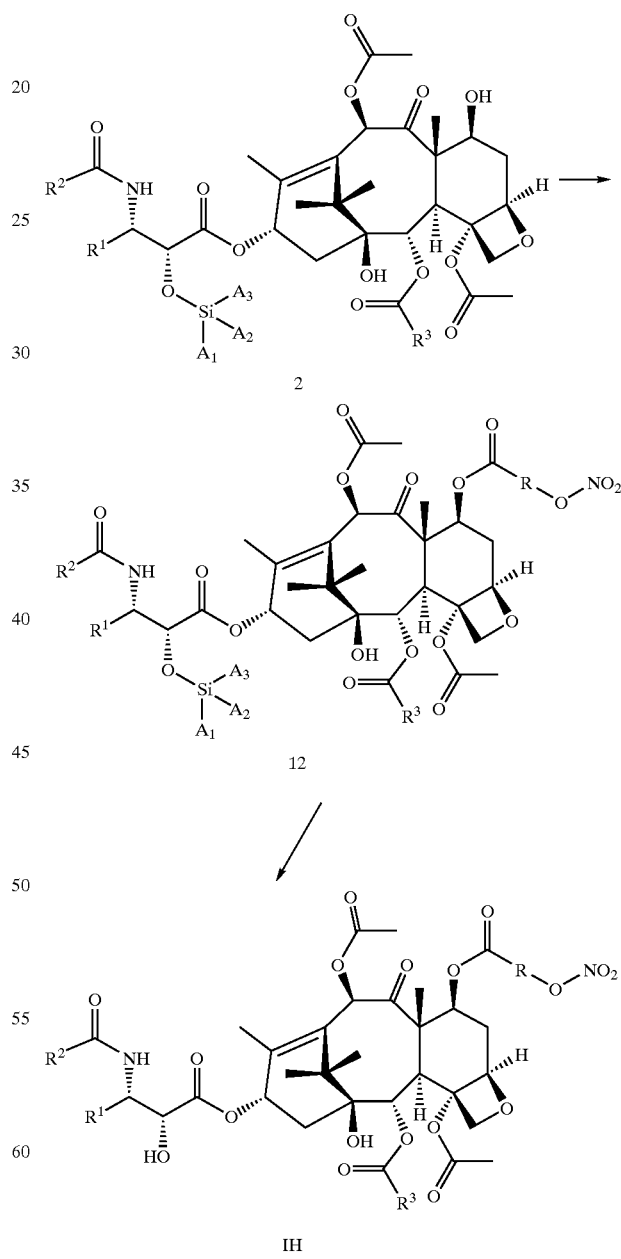

preferably in the presence of a condensation catalyst, such as DMAP. Alternatively, the acid may first be converted to the acid chloride by treatment with oxalyl chloride in the presence of a catalytic amount of DMF. The acid chloride is then reacted with the 7-hydroxyl, preferably in the presence of a condensation catalyst, such as DMAP, and a tertiary amine base, such as triethylamine, to produce the ester. Alternatively, the nitrate containing acid and 7-hydroxyl may be coupled to produce the ester by treatment with a dehydration agent, such as DCC or EDAC .HCl, with a catalyst such as DMAP or HOBt. Deprotection of the 2'-hydroxyl moiety (fluoride ion or aqueous acid are the preferred methods for removing silyl ether protecting groups) produces the compounds of formula IH.

Nitro compounds of formula (I) wherein $R^1$, $R^2$, $R^3$, $R_e$, $R_f$, a, b, c, d, g, i, j, p, v, x, z, $A_1$, $A_2$ and $A_3$ are as defined herein, $D^1$ is a hydrogen, $D^2$ is an acetate, $R^{10}$ is a hydrogen and a nitrate containing ester is representative of the $R^9$ group as defined herein, may be prepared as outlined in Scheme 8. The 7-hydroxyl group of the compound of formula 2 is converted to the ester of formula 12, wherein R is as defined herein by reaction with an appropriate protected nitrate containing active acylating agent. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the 7-hydroxyl, Nitro compounds of formula (I) wherein $R^1$, $R^2$, $R^3$, $R_e$, $R_f$, a, b, c, d, g, i, j, p, v, x, z, K, $A_1$, $A_2$ and $A_3$ are as defined herein, $D^1$ is a hydrogen or a K group, $D^2$ is an acetate, $R^{10}$ is a hydrogen and a nitrate containing ester is representative of the $R^9$ group as defined herein, may be prepared as outlined in Scheme 9. The compound of formula 1 is converted to the diester of formula IJ, wherein R is as defined herein, by reaction with an appropriate nitrate containing active acylating agent. Preferred methods for the preparation of esters are initially forming the mixed anhydride via reaction of the acid with a chloroformate, such as isobutylchloroformate, in the presence of a non-nucleophilic base, such as triethylamine, in an anhydrous inert solvent, such as dichloromethane, diethylether or THF. The mixed anhydride is then reacted with the 2'- and 7-hydroxyls, preferably in the presence of a condensation catalyst, such as DMAP. Alternatively, the acid may first be converted to the acid chloride by treatment with oxalyl chloride in the presence of a catalytic amount of DMF. The acid chloride is then reacted with the 2'- and 7-hydroxyls, preferably in the presence of a condensation catalyst, such as DMAP, and a tertiary amine base, such as triethylamine, to produce the diester. Alternatively, the nitrate containing acid and the 2' and 7-hydroxyls may be coupled to produce the diester by treatment with a dehydration agent, such as DCC or EDAC.HCl with a catalyst such as DMAP or HOBt.

Scheme 9

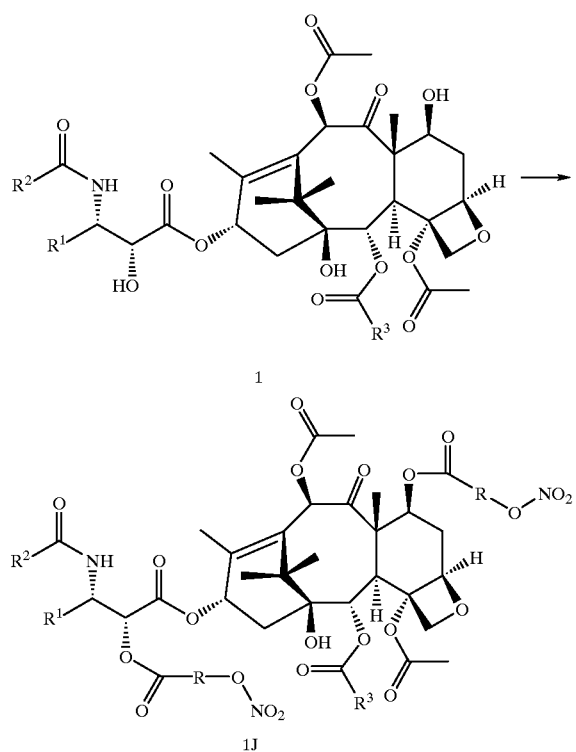

The compounds of the present invention include taxane compounds, including those described herein, which have been nitrosated and/or nitrosylated through one or more sites such as oxygen (hydroxyl condensation), sulfur (sulfhydryl condensation) and/or nitrogen. The nitrosated and/or nitrosylated taxanes of the present invention donate, transfer or release a biologically active form of nitrogen monoxide (nitric oxide).

Nitrogen monoxide can exist in three forms: NO– (nitroxyl), NO• (nitric oxide) and NO$^+$ (nitrosonium). NO• is a highly reactive short-lived species that is potentially toxic to cells. This is critical because the pharmacological efficacy of NO depends upon the form in which it is delivered. In contrast to the nitric oxide radical (NO•), nitrosonium (NO$^+$) does not react with $O_2$ or $O_2^-$—species, and functionalities capable of transferring and/or releasing NO$^+$ and NO— are also resistant to decomposition in the presence of many redox metals. Consequently, administration of charged NO equivalents (positive and/or negative) does not result in the generation of toxic by-products or the elimination of the active NO moiety.

Compounds contemplated for use in the present invention (e.g., taxanes and/or nitrosated and/or nitrosylated taxanes) are, optionally, used in combination with nitric oxide and compounds that release nitric oxide or otherwise directly or indirectly deliver or transfer nitric oxide to a site of its activity, such as on a cell membrane in vivo.

The term "nitric oxide" encompasses uncharged nitric oxide (NO•) and charged nitrogen monoxide species, preferably charged nitrogen monoxide species, such as nitrosonium ion (NO$^+$) and nitroxyl ion (NO–). The reactive form of nitric oxide can be provided by gaseous nitric oxide. The nitric oxide releasing, delivering or transferring compounds, have the structure F—NO, wherein F is a nitric oxide releasing, delivering or transferring moiety, include any and all such compounds which provide nitric oxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-((E)-hydroxyimino)-5-nitro-3-hexene amines or amides, nitrosoamines, furoxans as well as substrates for the endogenous enzymes which synthesize nitric oxide. NONOates include, but are not limited to, (Z)-1-{N-methyl-N-(6-(N-methyl-ammoniohexyl)amino)}diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-{N-(3-aminopropyl)-N-(4-(3-aminopropylammonio)butyl)-amino}diazen-1-ium-1,2-diolate (spermine NONOate or "SPER/NO") and sodium (Z)-1-(N,N-diethylamino)diazenium-1,2-diolate (diethylamine NONOate or "DEA/NO") and derivatives thereof. The "NO adducts" may be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an alkylaryl, a carboxamido, a alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, $W_h$, , or $-(C(R_e)(R_f))_k-T-Q$, or $R_e$ and $R_f$ taken together with the carbons to which they are attached form a carbonyl, a methanthial, a heterocyclic ring, a cycloalkyl group or a bridged cycloalkyl group; Q is $-NO$ or $-NO_2$; and T is independently a covalent bond, a carbonyl, an oxygen, $-S(O)$, or $-N(R_a)R_i$, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, $-CH_2-C(T-Q)(R_e)(R_f)$, or $-(N_2O_2-)^-\cdot M^+$, wherein $M^+$ is an organic or inorganic cation; with the proviso that when $R_i$ is $-CH_2-C(T-Q)(R_e)(R_f)$ or $-(N_2O_2-)\cdot M^+$; then "$-T-Q$" can be a hydrogen, an alkyl group, an alkoxyalkyl group, an aminoalkyl group, a hydroxy group or an aryl group.

In cases where $R_e$ and $R_f$ are a heterocyclic ring or $R_e$ and $R_f$ when taken together with the carbon atoms to which they are attached are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the present invention, where the NO adduct is a compound that donates, transfers or releases nitric oxide, include compounds comprising at least one $ON-O-$, $ON-N-$ or $ON-C$-group. The compounds that include at least one $ON-O-$, $ON-N-$ or $ON-C$-group are preferably $ON-O-$, $ON-N-$ or $ON-C$-polypeptides (the term "polypeptide" includes proteins and polyamino acids that do not possess an ascertained biological function, and derivatives thereof); $ON-O$, $ON-N-$ or $ON-C$-amino acids (including natural and synthetic amino acids and their stereoisomers and racemic mixtures); $ON-O-$, $ON-N-$ or $ON-C$-sugars; $ON-O-$, $ON-N-$ or $ON-C$-modified or unmodified oligonucleotides (comprising at least 5 nucleotides, preferably 5–200 nucleotides); $ON-O-$, $ON-N-$ or $ON-C$-straight or branched, saturated or unsaturated, aliphatic or aromatic, substituted or unsubstituted hydrocarbons; and $ON-O-$, $ON-N-$ or $ON-C$-heterocyclic compounds.

Another group of NO adducts for use in the present invention include nitrates that donate, transfer or release nitric oxide, such as compounds comprising at least one $O_2N-O-$, $O_2N-N-$, $O_2N-S-$ or $O_2N-C$-group. Preferred among these compounds are $O_2N-O-$, $O_2N-N-$, $O_2N-S-$ or $O_2N-C$-polypeptides (the term "polypeptide" includes proteins and also polyamino acids that do not possess an ascertained biological function, and derivatives thereof); $O_2N-O-$, $O_2N-N-$, $O_2N-S-$ or $O_2N-C$-amino acids (including natural and synthetic amino acids and their stereoisomers and racemic mixtures); $O_2N-O-$, $O_2N-N-$, $O_2N-S-$ or $O_2N-C$-sugars; $O_2N-O-$, $O_2N-N-$, $O_2N-S-$ or $O_2N-C$-modified and unmodified oligonucleotides (comprising at least 5 nucleotides, preferably 5–200 nucleotides); $O_2N-O-$, $O_2N-N-$, $O_2N-S-$ or $O_2N-C$-straight or branched, saturated or unsaturated, aliphatic or aromatic, substituted or unsubstituted hydrocarbons; and $O_2N-O-$, $O_2N-N-$, $O_2N-S-$ or $O_2N-C$-heterocyclic compounds. Preferred examples of compounds comprising at least one $O_2N-O-$, $O_2N-N-$, $O_2N-S-$ or $O_2N-C$-group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in WO 97/46521 and WO 00/54756, the disclosures of each of which are incorporated by reference herein in their entirety.

Another group of NO adducts are N-oxo-N-nitrosoamines that donate, transfer or release nitric oxide and are represented by the formula: $R^1R^2N-N(O-M^+)-NO$, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and $M^+$ is as defined herein.

Another group of NO adducts are thionitrates that donate, transfer or release nitric oxide and are represented by the formula: $R^1-(S)-NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO−) and uncharged nitric oxide (NO•).

The present invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

The present invention is also based on the discovery that the administration of a therapeutically effective amount of the compounds and compositions described herein is effective for treating or preventing cardiovascular diseases and disorders. For example, the patient can be administered a therapeutically effective amount of at least one nitrosated and/or nitrosylated taxane of the present invention. In another embodiment, the patient can be administered a therapeutically effective amount of at least one taxane, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase. In yet another embodiment, the patient can be administered a therapeutically effective amount of at least one taxane, optionally substituted with at least one NO and/or $NO_2$ group, and at least one therapeutic agent, and, optionally, at least one compound that donates, transfers or releases nitric oxide as a charged species, or elevates levels of endogenous EDRF or nitric oxide, or is a substrate for nitric oxide synthase. The compounds can be administered separately or in the form of a composition.

A "therapeutic agent" useful in the present invention includes, but is not limited to, agents which biologically stent a vessel and/or reduce or inhibit vascular remodeling and/or inhibit or reduce vascular smooth muscle proliferation following a procedural vascular trauma. The "therapeutic agents" of the invention include agents that inhibit the cellular activity of a vascular smooth muscle cell, for example, proliferation, migration, increase in cell volume, increase in extracellular matrix synthesis (e.g., collagens, proteoglycans, and the like), or secretion of extracellular matrix materials by the cell. Suitable "therapeutic agents" useful in the present invention, include, but are not limited to, antithrombogenic agents (such as, for example, heparin, covalent heparin, hirudin, hirulog, coumadin, protamine, argatroban, D-phenylalanyl-L-poly-L-arginyl chloromethyl ketone, and the like); thrombolytic agents (such as, for example, urokinase, streptokinase, tissueplasminogen activators, and the like); fibrinolytic agents; vasospasm inhibitors; potassium channel activators (such as, for example, nicorandil, pinacidil, cromakalim, minoxidil, aprilkalim, loprazolam and the like); calcium channel blockers (such as, for example, nifedipine, veraparmil, diltiazem, gallopamil, niludipine, nimodipins, nicardipine, and the like); antihypertensive agents (such as, for example, HYTRIN®, and the like); antimicrobial agents or antibiotics (such as, for example, adriamycin, and the like); antiplatelet agents (such as, for example, aspirin, ticlopidine, a glycoprotein IIb/IIIa inhibitor, surface glycoprotein receptors and the like); antimitotic, antiproliferative agents or microtubule inhibitors (such as, for example, colchicine, methotrexate, azathioprine, vincristine, vinblastine, cytochalasin, fluorouracil, adriamycin, mutamycin, tubercidin, epothilone A or B, discodermolide, and the like); antisecretory agents (such as, for example, retinoid, and the like); remodelling inhibitors; antisense nucleotides (such as, for example, deoxyribonucleic acid, and the like); anti-cancer agents (such as, for example, tamoxifen citrate, acivicin, bizelesin, daunorubicin, epirubicin, mitoxantrone, and the like); steroids (such as, for example, dexamethasone, dexamethasone sodium phosphate, dexamethasone acetate, and the like); non-steroidal antiinflammatory agents (NSAID); COX-2 inhibitors; immunosuppressive agents (such as, for example cyclosporin, and the like); growth factor antagonists or antibodies (such as, for example, trapidal (a PDGF antagonist), angiopeptin (a growth hormone antagonist), angiogenin, and the like); dopamine agonists (such as, for example, apomorphine, bromocriptine, testosterone, cocaine, strychnine, and the like); radiotherapeutic agents (such as, for example, $^{60}Co$ (5.3 year half life), $^{192}Ir$ (73.8 days), $^{32}P$ (14.3 days), $^{111}In$ (68 hours), $^{90}Y$ (64 hours), $^{99m}Tc$ (6 hours), and the like); heavy metals functioning as radioplaque agents (such as, for example, iodine-containing compounds, barium-containing compounds, gold, tantalum, platinum, tungsten, and the like); biologic agents (such as, for example, peptides, proteins, enzymes, extracellular matrix components, cellular components, and the like); angiotensin converting enzyme (ACE) inhibitors; angiotensin II receptor antagonists; renin inhibitors; free radical scavengers, iron chelators or antioxidants (such as, for example, ascorbic acid, alpha tocopherol, superoxide dismutase, deferoxamine, 21-aminosteroid, and the like); sex hormone (such as, for example, estrogen, and the like); antipolymerases (such as, for example, AZT, and the like); antiviral agents (such a, for example, acyclovir, famciclovir, rimantadine hydrochloride, ganciclovir sodium, Norvir, Crixivan, and the like); photodynamic therapy agents (such as, for example, 5-aminolevulinic acid, meta-tetrahydroxyphenylchlorin, hexadecafluoro zinc phthalocyanine, tetramethyl hematoporphyrin, rhodamine 123, and the like); antibody targeted therapy agents (such as, for example, IgG2 Kappa antibodies against Pseudomonas aeruginosa exotoxin A and reactive with A431 epidermoid carcinoma cells, monoclonal antibody against the noradrenergic enzyme dopamine beta-hydroxylase conjugated to saporin, and the like); gene therapy agents; and mixtures thereof. The taxane, nitric oxide donors and/or therapeutic agents can be administered separately or in the form of a composition. The compounds and compositions of the present invention can also be administered in combination with other medications used for the treatment of these diseases or disorders.

Suitable NSAIDs include, but are not limited to, acetaminophen, aspirin, diclofenac, ibuprofen, ketoprofen, naproxen and the like. Suitable NSAIDs are described more fully in the literature, such as in Goodman and Gilman, The Pharmacological Basis of Therapeutics (9th Edition), McGraw-Hill, 1995, Pgs. 617–657; the Merck Index on CD-ROM, Twelfth Edition, Version 12:1, 1996; STN express file reg and file phar. Suitable NSAIDs are also described and claimed in U.S. Pat. No. 6,057,347 assigned to NitroMed, Inc., the disclosure of which is incorporated by reference herein in its entirety.

Suitable COX-2 inhibitors include, but are not limited to, those disclosed in, for example, U.S. Pat. Nos. 5,134,142, .5,344,991, 5,380,738, 5,393,790, 5,409,944, 5,434,178, 5,436,265, 5,466,823, 5,474,995, 5,475,021, 5,486,534, 5,504,215, 5,508,426, 5,510,368, 5,510,496, 5,516,907, 5,521,207, 5,521,213, 5,536,752, 5,550,142, 5,552,422, 5,563,165, 5,580,985, 5,585,504, 5,596,008, 5,604,253, 5,604,260, 5,616,601, 5,620,999, 5,633,272, 5,639,780, 5,643,933, 5,677,318, 5,681,842, 5,686,460, 5,686,470, 5,691,374, 5,696,143, 5,698,584, 5,700,816, 5,710,140, 5,719,163, 5,733,909, 5,750,558, 5,753,688, 5,756,530, 5,756,531, 5,760,068, 5,776,967, 5,776,984, 5,783,597, 5,789,413, 5,807,873, 5,817,700, 5,824,699, 5,830,911, 5,840,746, 5,840,924, 5,849,943, 5,859,257, 5,861,419, 5,883,267, 5,905,089, 5,908,852, 5,908,858, 5,935,990, 5,945,539, 5,972,986, 5,980,905, 5,981,576, 5,985,902, 5,925,631, 5,990,148, 5,994,379, 5,994,381, 6,001,843, 6,002,014, 6,020,343, 6,025,353, 6,046,191, 6,071,936, 6,071,954, 6,077,869, 6,080,876, 6,083,969 and in WO 94/20480, WO 94/13635, WO 94/15932, WO 94/26731, WO 94/27980, WO 95/00501, WO 95/11883, WO 95/15315, WO 95/15316, WO 95/15318, WO 95/17317, WO 95/18799, WO 95/21817, WO 95/30652, WO 95/30656, WO 96/03392, WO 96/03385, WO 96/03387, WO 96/03388, WO 96/06840, WO 96/10021, WO 96/13483, WO 96/16934, WO 96/19469, WO 96/21667, WO 96/23786, WO 96/24584, WO 96/25405, WO 96/31509, WO 96/36623, WO 96/36617, WO 96/38418, WO 96/38442, WO 96/37467, WO 96/37468, WO 96/37469, WO 96/41626, WO 96/41645, WO 97/03953, WO 97/13767, WO 97/14691, WO 97/16435, WO 97/25045, WO 97/27181, WO 97/28120, WO 97/28121, WO 97/29776, WO 97/34882, WO 97/36863, WO 97/37984, WO 97/38986, WO 97/44027, WO 97/44028, WO 97/45420, WO 98/00416, WO 98/03484, WO 98/04527, WO 98/06708, WO 98/07714, WO 98/11080, WO 98/21195, WO 98/22442, WO 98/39330, WO 98/41511, WO 98/41516, WO 98/43649, WO 98/43966, WO 98/46594, WO 98/47509, WO 98/47871, WO 98/47890, WO 98/50033, WO 98/50075, WO 99/05104, WO 99/10331, WO 99/10332, WO 99/12930, WO 99/13799, WO 99/14194, WO 99/14195, WO 99/15205, WO 99/15503, WO 99/15505, WO 99/15513, WO 99/18960, WO 99/20110, WO 99/21585, WO 99/22720, WO 99/23087, WO 99/25695, WO 99/33796, WO 99/35130, WO 99/45913, WO 99/55830, WO 99/59634, WO 99/59635, WO 99/61016, WO 99/61436, WO 99/62884, WO 00/00200, WO 00/08024, WO 00/01380, WO 00/13685, WO 00/24719, WO 00/23433, WO 00/26216 and in EP 0 745 596 A1, EP 0 788 476 B1, EP 0 863 134 A1, EP 0 937 722 A1 and in U.S. application Ser. No. 09/741,816 filed Dec. 23, 2000, which is assigned to NitroMed, Inc.,the disclosures of each of which are incorporated by reference herein in their entirety.

Suitable anticoagulants include, but are not limited to, heparin, coumarin, aspirin, protamine, warfarin, dicumarol, phenprocoumon, indan-1,3-dione, acenocoumarol, ansindione, and the like. Suitable anticoagulants are described more fully in the literature, such as in Goodman and Gilman, The Pharmacological Basis of Therapeutics (9th Edition), McGraw-Hill, 1995, Pgs. 1341–1359; the Merck Index on CD-ROM, Twelfth Edition, Version 12:1, 1996; STN express file reg and file phar.

Suitable angiotensin-converting enzyme inhibitors, include, but are not limited to, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, trandolapril, and the like. Suitable angiotensin-converting enzyme inhibitors are described more fully in the literature, such as in Goodman and Gilman, The Pharmacological Basis of Therapeutics (9th Edition), McGraw-Hill, 1995, Pgs. 733–838; and the Merck Index on CD-ROM, Twelfth Edition, Version 12:1, 1996; and on STN Express, file phar.

Suitable angiotensin II receptor antagonists, include, but are not limited to, ciclosidomine, eprosartan, furosemide, irbesartan, losartan, saralasin, valsartan, and the like. Suitable angiotensin II receptor antagonists are described more fully in the literature, such as in Goodman and Gilman, The Pharmacological Basis of Therapeutics (9th Edition), McGraw-Hill, 1995, Pgs. 733–838; and the Merck Index on CD-ROM, Twelfth Edition, Version 12:1, 1996; and on STN Express, file phar.

Suitable renin inhibitors, include, but are not limited to, enalkrein, RO 42-5892, A 65317, CP 80794, ES 1005, ES 8891, SQ 34017, and the like. Suitable renin inhibitors are described more fully in the literature, such as in Goodman and Gilman, The Pharmacological Basis of Therapeutics (9th Edition), McGraw-Hill, 1995, Pgs. 733–838; and the Merck Index on CD-ROM, Twelfth Edition, Version 12:1, 1996; and on STN Express, file phar and file reg.

Another embodiment of the invention provides compositions comprising at least one taxane that is optionally nitrosated and/or nitrosylated, and, optionally, at least one compound that donates, transfers or releases nitric oxide and/or stimulates the endogenous production of NO or EDRF in vivo and/or is a substrate for nitric oxide synthase and/or at least one therapeutic agent, bound to a matrix. Preferably, the nitrosated and/or nitrosylated taxane is of formula (I). Preferably, the compounds that donates, transfers or releases nitric oxide and/or stimulates the endogenous production of NO or EDRF in vivo and/or is a substrate for nitric oxide synthase (i.e., NO donors) and the therapeutic agents are those described herein.

The nitrosated and/or nitrosylated taxanes, and, optionally, NO donors and/or therapeutic agents, can be incorporated into a natural or synthetic matrix which can then be applied with specificity to a biological site of interest. Accordingly the optionally substituted taxane and, optionally, NO donor and/or therapeutic agent is "bound to the matrix" which means that the nitrosated or nitrosylated taxanes, and, optionally, NO donors and/or therapeutic agent, are physically and/or chemically associated with part of, incorporated with, attached to, or contained within the natural or synthetic matrix. In one embodiment, physical association or bonding can be achieved, for example, by coprecipitation of the nitrosated and/or nitrosylated taxane, and, optionally, NO donor and/or therapeutic agent, with the matrix. In another embodiment, chemical association or bonding can be achieved by, for example, covalent bonding of a nucleophilic moiety of the nitrosated and/or nitrosylated taxane, and, optionally, NO donor, and/or therapeutic agent, to the matrix, such that the taxane is part of the matrix itself.

In yet another embodiment, the nitrosated and/or nitrosylated taxane, and, optionally, NO donor, and/or therapeutic agent can be incorporated into a porous layer of the matrix or into pores included in the natural or synthetic matrix. The manner in which the nitrosated and/or nitrosylated taxane, and, optionally, NO donor and/or therapeutic agent, is associated, part of, attached to, incorporated with or contained within (i.e. "bound to") the matrix is inconsequential to the present invention and all means of association, incorporation, attachment, and bonding are contemplated herein. Incorporation of the nitrosated and/or nitrosylated taxanes, and, optionally, NO donors, and/or therapeutic agents, into the matrix results in site-specific application, thereby enhancing selectivity of action for the released nitric oxide and parent taxane. Additionally, incorporation of the nitrosated and/or nitrosylated taxanes into the matrix reduces the rate of release of the nitric oxide and the parent taxane. This prolongs the release of the nitric oxide and the parent taxane thereby allowing for efficient dosing to achieve a desired biological effect so that the frequency of dosing can be reduced.

Any of a wide variety of natural or synthetic polymers can be used as the matrix in the context of the present invention. It is only necessary for the matrix to be biologically acceptable. Exemplary matrixes suitable for use in the present invention are polymers including, for example, polyolefins (such as polystyrene, polypropylene, polyethylene, high density polyethylene, polytetrafluorethylene, polyvinylidene diflouride and polyvinylchloride), polyethylenimine or derivatives thereof, polyethers (such as polyethylene glycol), polyesters (such as poly-L-lactic acid, poly-D, L-lactic, poly-D-lactic, polyglycolic, polybutyric acid, polycaprolactone, polyethylene vinyl actetate, polyisopropyl myristate, poly-(lactide/glycolide)), polyanhydrides, polyhydroxybutyrates, polyamides (such as nylon), polyurethanes, polyurethane copolymers (such as pellethane polymers), polyacrylates (such as polymethacrylate, poly (2-(methacryloyloxyethyl)-2'-(trimethylammonium)ethyl phosphate inner salt-co-n-dodecyl methacrylate), mixtures of polymers (such as polylactic acid/polylysine copolymers, polylactic acid/polyglycolic acid, polylactic acid/polycaprolactone, polyurethane/polyester copolymers, polyurethane/polyether copolymers, nylon/polyether copolymers, such as vestamid), blocked polymers, blocked copolymers, biopolymers (such as peptides, proteins, oligonucleotides, antibodies, peptide hormones, glycoproteins, glycogen and nucleic acids), starburst dendrimers, natural fibrous matrix (such as filter paper), synthetic fibrous matrix materials (such as three-dimensional lattice of synthetic polymers and copolymers) and the like. The matrix could also be a blend of polymeric coatings or a hybrid coating such that a controlled release of the active agent is obtained. Exemplary polymers are described in U.S. Pat. Nos. 5,705,583, 5,770,645, 5,994,444, 6,087,479 and 6,231,600 and in WO 99/21908 and WO 01/01890, the disclosures of each of which are incorporated by reference herein in their entirety.

The physical and structural characteristics of the matrixes suitable for use in the present invention are not critical, but depend on the application. It will be appreciated by one skilled in the art that where the matrix-taxane composition of the present invention is intended for local, relatively short term administration or similar administration they need not be biodegradable. For some uses, such as postangioplasty, coronary bypass surgery or intimal hyperplasia associated with vascular graft implants or the like, it may be desirable for the matrix to slowly dissolve in a physiological environment or to be biodegradable.

The nitrosated and/or nitrosylated taxane or parent taxane and, optionally, the compound that donates, transfers or releases nitric oxide and/or stimulates the endogenous production of NO or EDRF in vivo and/or is a substrate for nitric oxide synthase and/or therapeutic agent bound to the matrix may be administered in a wide variety of forms or delivery means. Any delivery means should adequately protect the integrity of the nitric oxide prior to its release and should control the release of the nitric oxide at such a rate, in such an amount, and in such a location as to serve as an effective means for prevention and/or treatment of cardiovascular diseases and disorders, including restenosis. Delivery means for local administration include, for example, sutures, vascular implants, stents, heart valves, drug pumps, drug delivery catheters and the like. Delivery means for systemic administration include, for example, solutions, suspensions, emulsions, capsules, powders, sachets, tablets, effervescent tablets, topical patches, lozenges, aerosols, liposomes, microparticles, microspheres, beads and the like. The matrix itself may be structurally sufficient to serve as a delivery means.

The nitrosated and/or nitrosylated taxane or parent taxane and, optionally, the compound that donates, transfers or releases nitric oxide and/or stimulates the endogenous production of NO or EDRF in vivo and/or is a substrate for nitric oxide synthase and/or therapeutic agent, bound to the matrix can also be used to coat the surface of a medical device or instrument that comes into contact with blood (including blood components and blood products) or vascular tissue thereby rendering the surface passive. Alternatively the nitrosated and/or nitrosylated taxane or the parent taxane and the compound that donates, transfers or releases nitric oxide and/or stimulates the endogenous production of NO or EDRF in vivo and/or is a substrate for nitric oxide synthase and, optionally, the therapeutic agent, bound to the matrix can also be used to coat the surface of a medical device or instrument that comes into contact with blood (including blood components and blood products) or vascular tissue thereby rendering the surface passive. U.S. Pat. Nos. 5,837,008, 5,665,077, 5,797,887 and 5,824,049, the disclosures of each of which are incorporated by reference herein in their entirety, describe methods for coating a surface of a medical device or instrument. Thus, for example, (i) all or a portion of the medical device may be coated with the nitrosated and/or nitrosylated taxanes, and, optionally, NO donors and/or therapeutic agents, either as the coating per se or bound to a matrix, as described herein; or (ii) all or a portion of the medical device may be produced from a material which includes the nitrosated and/or nitrosylated taxane, and, optionally, NO donor and/or therapeutic agent, per se or bound to a matrix, as described herein.

It is also contemplated that artificial surfaces will vary depending on the nature of the surface, and such characteristics including contour, crystallinity, hydrophobicity, hydrophilicity, capacity for hydrogen bonding, and flexibility of the molecular backbone and polymers. Therefore, using routine methods, one of ordinary skill will be able to customize the coating technique by adjusting such parameters as the amount of adduct, length of treatment, temperature, diluents, and storage conditions, in order to provide optimal coating of each particular type of surface.

After the device or artificial material has been coated with the nitrosated and/or nitrosylated taxane and, optionally, NO donor and/or therapeutic agent, or with the taxane and NO donor, and, optionally, the therapeutic agent, it will be suitable for its intended use, including, for example, implantation as a heart valve, insertion as a catheter, insertion as a stent, or for cardiopulmonary oxygenation or hemodialysis.

The present invention also describes methods for the administration of a therapeutically effective amount of the compounds and compositions described herein for treating or preventing cardiovascular diseases and disorders including, for example, restenosis and atherosclerosis. For example, the patient can be administered a therapeutically effective amount of at least one nitrosated and/or nitrosylated taxane of the present invention. In another embodiment, the patient can be administered a therapeutically effective amount of at least one taxane, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase. In yet another embodiment, the patient can be administered a therapeutically effective amount of at least one taxane, optionally substituted with at least one NO and/or $NO_2$ group, and at least one therapeutic agent, and, optionally, at least one compound that donates, transfers or releases nitric oxide as a charged species, or elevates levels of endogenous EDRF or nitric oxide, or is a substrate for nitric oxide synthase. The compounds can be administered separately or in the form of a composition.

Another embodiment of the present invention provides methods for the prevention of platelet aggregation and platelet adhesion caused by the exposure of blood (including blood components or blood products) to a medical device or instrument by incorporating at least one nitrosated and/or nitrosylated taxane or parent taxane, and, optionally, at least one compound that donates, transfers or releases nitric oxide and/or stimulates the endogenous production of NO or EDRF in vivo and/or is a substrate for nitric oxide synthase, and/or therapeutic agent, capable of releasing a therapeutically effective amount of nitric oxide, into and/or on the portion(s) of the medical device that come into contact with blood (including blood components or blood products) or vascular tissue. The nitrosated and/or nitrosylated taxane or parent taxane, and, optionally, NO donors, may be directly or indirectly linked to the natural or synthetic polymeric material from which all or a portion of the device is made, as disclosed in U.S. Pat. No. 6,087,479, assigned to NitroMed, the disclosure of which is incorporated by reference herein in its entirety. Alternatively, the nitrosated and/or nitrosylated taxane, or parent taxane, and, optionally, NO donors, may be incorporated into the body of the device which is formed of a biodegradable or bioresorbable material, including the matrix described herein. Thus the nitric oxide is released over a sustained period of the resorption or degradation of the body of the device.

Another embodiment of the present invention provides methods to prevent or treat autoimmune diseases, pathological conditions resulting from abnormal cell proliferation, polycystic kidney disease (PKD), inflammatory diseases, to preserve organs and/or tissues, (such as, for example, for organ transplants, and the like) and to inhibit wound contraction by administering to a patient in need thereof a therapeutically effective amount of the compounds and/or compositions described herein. For example, the patient can be administered a therapeutically effective amount of at least one nitrosated and/or nitrosylated taxane of the present invention. In another embodiment, the patient can be administered a therapeutically effective amount of at least one taxane, optionally substituted with at least one NO and/or $NO_2$ group, and at least one compound that donates, transfers or releases nitric oxide as a charged species, or elevates levels of endogenous EDRF or nitric oxide or is a substrate for nitric oxide synthase. In yet another embodiment, the patient can be administered a therapeutically effective amount of at least one taxane, optionally substituted with at least one NO and/or $NO_2$ group, and at least one therapeutic agent, and, optionally, at least one compound that donates, transfers or releases nitric oxide as a charged species, or elevates levels of endogenous EDRF or nitric oxide or is a substrate for nitric oxide synthase. The taxanes optionally substituted with at least one NO and/or $NO_2$ group, nitric oxide donors and/or therapeutic agents can be administered separately or in the form of a composition. The compounds and compositions of the present invention can also be administered in combination with other medications used for the treatment of these disorders.

Another embodiment of the present invention relates to local administration of the nitrosated and/or nitrosylated taxanes and/or parent taxanes, and, optionally, at least one compound that donates, transfers or releases nitric oxide and/or stimulates the endogenous production of NO or EDRF in vivo and/or is a substrate for nitric oxide synthase, to the site of injured or damaged tissue (e.g., damaged blood vessels) for the treatment of the injured or damaged tissue. Such damage may result from the use of a medical device in an invasive procedure. Thus, for example, in treating blocked vasculature by, for example, angioplasty, damage can result to the blood vessel. Such damage may be treated by use of the compounds and compositions described herein. In addition to repair of the damaged tissue, such treatment can also be used to prevent and/or alleviate and/or delay re-occlusions, for example, restenosis. The compounds and compositions can be locally delivered using any of the methods known to one skilled in the art, including but not limited to, a drug delivery catheter, an infusion catheter, a drug delivery guidewire, an implantable medical device, and the like. In one embodiment, all or most of the damaged area is coated with the nitrosated and/or nitrosylated taxanes described herein per se or in a pharmaceutically acceptable carrier or excipient which serves as a coating matrix, including the matrix described herein. This coating matrix can be of a liquid, gel or semisolid consistency. The nitrosated and/or nitrosylated taxanes can be applied in combination with one or more therapeutic agents, such as those listed above. The carrier or matrix can be made of or include agents which provide for metered or sustained release of the therapeutic agents.

In preventing and/or treating cardiovascular diseases and disorders, the nitrosated and/or nitrosylated taxanes and, optionally, at least one compound that donates, transfers or releases nitric oxide and/or stimulates the endogenous production of NO or EDRF in vivo and/or is a substrate for nitric oxide synthase can be administered directly to the damaged vascular surface intravenously by using an intraarterial or intravenous catheter, suitable for delivery of the compounds to the desired location. The location of damaged arterial surfaces is determined by conventional diagnostic methods, such as X-ray angiography, performed using routine and well-known methods available to one skilled in the art. In addition, administration of the nitrosated and/or nitrosylated taxanes, and, optionally, NO donors, using an intraarterial or intravenous catheter is performed using routine methods well known to one skilled in the art. Typically, the compound or composition is delivered to the site of angioplasty through the same catheter used for the primary procedure, usually introduced to the carotid or coronary artery at the time of angioplasty balloon inflation. The nitrosated and/or nitrosylated taxanes, and, optionally, NO donors, slowly decompose at body temperature over a prolonged period of time releasing nitric oxide at a rate effective to prevent and/or treat cardiovascular diseases and disorders including, for example, restenosis.

When administered in vivo, the compounds and compositions of the present invention can be administered in combination with pharmaceutically acceptable carriers and in dosages described herein. When the compounds and compositions of the present invention are administered as a mixture of at least one nitrosated and/or nitrosylated taxane or at least one parent taxane and at least one nitric oxide donor, they can also be used in combination with one or more additional compounds which are known to be effective against the specific disease state targeted for treatment (e.g., therapeutic agents). The nitric oxide donors and/or therapeutic agents can be administered simultaneously with, subsequently to, or prior to administration of the taxane, including those that are substituted with one or more NO and/or $NO_2$ groups, and/or other additional compounds.

The compounds and compositions of the present invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, pastes, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances that increase the viscosity of the suspension and include, for example, sodium carboxymethyl cellulose, sorbitol and/or dextran. Optionally, the suspension may also contain stabilizers.

Solvents useful in the practice of this invention include pharmaceutically acceptable, water-miscible, non-aqueous solvents. In the context of this invention, these solvents should be taken to include solvents that are generally acceptable for pharmaceutical use, substantially water-miscible, and substantially non-aqueous. Preferably, these solvents are also non-phthalate plasticizer leaching solvents, so that, when used in medical equipment, they substantially do not leach phthalate plasticizers that may be present in the medical equipment. More preferably, the pharmaceutically-acceptable, water-miscible, non-aqueous solvents usable in the practice of this invention include, but are not limited to, N-methyl pyrrolidone (NMP); propylene glycol; ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (S)-(-)-ethyl lactate; acetone; glycerol; alkyl ketones such as methylethyl ketone or dimethyl sulfone; tetrahydrofuran; cyclic alkyl amides such as caprolactam; decyhnethylsulfoxide; oleic acid; aromatic amines such as N,N-diethyl-m-toluamide; or 1-dodecylazacycloheptan-2-one.

The most preferred pharmaceutically-acceptable, water-miscible, non-aqueous solvents are N-methyl pyrrolidone (NMP), propylene glycol, ethyl acetate, dimethyl sulfoxide, dimethyl acetamide, benzyl alcohol, 2-pyrrolidone, or benzyl benzoate. Ethanol may also be used as a pharmaceutically-acceptable, water-miscible, non-aqueous solvent according to the invention, despite its negative impact on stability. Additionally, triacetin may also be used as a pharmaceutically-acceptable, water-miscible, non-aqueous solvent, as well as functioning as a solubilizer in certain circumstances. NMP may be available as PHARMASOLVE® from International Specialty Products (Wayne, N.J.). Benzyl alcohol may be available from J. T. Baker, Inc. Ethanol may be available from Spectrum, Inc. Triacetin may be available from Mallinkrodt, Inc.

The compositions of this invention can further include solubilizers. Solubilization is a phenomenon that enables the formation of a solution. It is related to the presence of amphiphiles, that is, those molecules that have the dual properties of being both polar and non-polar in the solution that have the ability to increase the solubility of materials that are normally insoluble or only slightly soluble, in the dispersion medium. Solubilizers often have surfactant properties. Their function may be to enhance the solubility of a solute in a solution, rather than acting as a solvent, although in exceptional circumstances, a single compound may have both solubilizing and solvent characteristics. Solubilizers useful in the practice of this invention include, but are not limited to, triacetin, polyethylene glycols (such as, for example, PEG 300, PEG 400, or their blend with 3350, and the like), polysorbates (such as, for example, Polysorbate 20, Polysorbate 40, Polysorbate 60, Polysorbate 65, Polysorbate 80, and the like), poloxamers (such as, for example, Poloxamer 124, Poloxamer 188, Poloxamer 237, Poloxamer 338, Poloxamer 407, and the like), polyoxyethylene ethers (such as, for example, Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether, and the like), polyoxylstearates (such as, for example, Polyoxyl 30 stearate, Polyoxyl 40 stearate, is Polyoxyl 50 stearate, Polyoxyl 100 stearate, and the like), polyethoxylated stearates (such as, for example, polyethoxylated 12-hydroxy stearate, and the like), and Tributyrin.

Other materials that may be added to the compositions of the present invention include cyclodextrins, and cyclodextrin analogs and derivatives, and other soluble excipients that could enhance the stability of the inventive composition, maintain the product in solution, or prevent side effects associated with the administration of the inventive composition. Cyclodextrins may be available as ENCAPSIN® from Janssen Pharmaceuticals.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules, nanoparticles, and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are preferred. The therapeutic dosage forms of this aspect of the present invention may be of any configuration suitable for sustained release. Preferred sustained release therapeutic dosage forms exhibit one or more of the following characteristics: microparticles (e.g., from about 0.5 micrometers to about 100 micrometers in diameter, preferably about 0.5 to about 2 micrometers; or from about 0.01 micrometers to about 200 micrometers in diameter, preferably from about 0.5 to about 50 micrometers, and more preferably from about 2 to about 15 micrometers) or nanoparticles (e.g., from about 1.0 nanometer to about 1000 nanometers in diameter, preferably about 50 to about 250 nanometers; or from about 0.01 nanometer to about 1000 nanometers in diameter, preferably from about 50 to about 200 nanometers), free flowing powder structure; biodegradable structure designed to biodegrade over a period of time between from about 0.5 to about 180 days, preferably from about 1 to 3 to about 150 days, more preferably from about 3 to about 180 days, and most preferably from about 10 to about 21 days; or non-biodegradable structure to allow the therapeutic agent diffusion to occur over a time period of between from about 0.5 to about 180 days, more preferably from about 30 to about 120 days; or from about 3 to about 180 days, more preferably from about 10 to about 21 days; biocompatible with target tissue and the local physiological environment into which the dosage form to be administered, including yielding biocompatible biodegradation products; facilitate a stable and reproducible dispersion of therapeutic agent therein, preferably to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades; and/or for targeted dosage forms, capability to have, preferably, from about 1 to about 10,000 binding protein/ peptide to dosage form bonds and more preferably, a maximum of about 1 binding peptide to dosage form bond per 150 square angstroms of particle surface area. The total number of binding protein/peptide to dosage form bonds depends upon the particle size used. The binding proteins or peptides are capable of coupling to the particles of the therapeutic dosage form through covalent ligand sandwich or non-covalent modalities as set forth herein.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomal vesicles and lysosomes. Preferred larger microparticle therapeutic dosage forms of the present invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the present invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Preferred sustained release dosage forms of the present invention comprise biodegradable microparticles or nanoparticles. More preferably, biodegradable microparticles or nanoparticles are formed of a polymer containing matrix that biodegrades by random, nonenzymatic, hydrolytic scissioning to release therapeutic agent, thereby forming pores within the particulate structure.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitrous (nitrite salt), nitric (nitrate salt), carbonic, sulfuric, phosphoric acid, and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesuifonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The usual doses of taxanes (including nitrosated and/or nitrosylated taxanes) for the treatment or prevention of restenosis and/or atherosclerosis maybe, but are not limited to, 24 hour continuous intraveneous pretreatment up to about 0.5 to about 2 mg/kg (about 20 to about 80 mg/m$^2$) prior to the vascular procedure, about 0.25 to about 0.2 mg/kg (about 10 to about 80 mg/m$^2$) continuous intraveneous infusion over about 245 hours post-procedure, then about 0.25 to about 2 mg/kg (about 10 to about 80 mg/m$^2$) continuous intraveneous infusion over 24 hours every 21 days for 1 to 6 cycles. Such a dosage is significantly lower that that used to treat human cancers, which is approximately about 0.1 mg/kg to about 1000 mg/kg.

The doses of nitric oxide donors in the pharmaceutical composition will be dependent on the specific nitric oxide donor compound and the mode of administration. For example, when L-arginine is the orally administered nitric oxide donor, it can be administered in an amount of about 3 grams to about 15 grams to provide a plasma level in the range of about 0.2 mM to about 30 mM. When L-arginine is delivered directly at the site of injury by local administration, the L-arginine is delivered in an amount of at least about 50 mg to about 500 mg, preferably about 100 mg to about 2 g. The time of the treatment will usually be at least about 2 minutes to about 30 minutes, more preferably about 5 minutes to about 15 minutes.

The nitrosated and/or nitrosylated taxanes of the invention are used at dose ranges and over a course of dose regimen and are administered in the same or substantially equivalent vehicles/carrier by the same or substantially equivalent as their non-nitrosated/nitrosylated counterparts. The nitrosated and/or nitrosylated compounds of the invention can also be used in lower doses and in less extensive regimens of treatment. The amount of active ingredient that can be combined with the carrier materials to produce a single dosage form will vary depending upon the host treated and the particular mode of administration, and is within the skill in the art.

The present invention also provides pharmaceutical kits comprising one or more containers filled with one or more of the ingredients of the pharmaceutical compounds and/or compositions of the present invention, including, one or more taxanes, optionally substituted with one or more NO and/or NO$_2$ groups, and one or more of the NO donors, and one or more therapeutic agents described herein. Such kits can also include, for example, other compounds and/or compositions (e.g., therapeutic agents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

EXAMPLES

The following non-limiting examples further describe and enable one of ordinary skill in the art to make and use the present invention.

Example 1

15-((3S,2R)-2-hydroxy-3-phenyl-3-(phenylcarbonylamino)propanoyloxy) (2S,4S,9S,10S,15S,7R,12R)-4,12-diacetyloxy-1-hydroxy-10,14,17,17-tetramethyl-6-oxa-11-oxo-2-phenylcarbonyloxytetracyclo(11.3.1.0<3,10>0.0<4,7>)heptadec-13-en-9-yl 3-methyl-3-(nitrosothio) butanoate 1a. (2S,4S,9S,10S,15S,7R,12R)-4,12-diacetyloxy-1,9-dihydroxy-10,14,17,17-tetramethyl-6-oxa-11-oxo2-phenylcarbonyloxytetracyclo(11.3.1.0<3,10>0.0<4,7>) heptadec-13-en-15-yl (3S,2R)-3-phenyl-3-(phenylcarbonylamino)-2-(2,2,2trichloroethoxy carbonyloxy)propanoate To Paclitaxel (1.73 g, 2.02 mmol) under argon was added methylene chloride (36 mL). The solution was cooled to −23±3° C. (internal temperature) and pyridine (3.5 mL) was added. 2,2,2-Trichloroethyl chloroformate (290 μL, 446 mg, 2.11 mmol) was slowly added. Stirring was maintained at −23±3° C. for 45 min. TLC showed incomplete reaction so more 2,2,2-trichloroethyl chloroformate (150 μL, 231 mg, 1.09 mmol) was added. Stirring was maintained at −23±3° C. for an additional 45 min. The reaction solution was diluted with methylene chloride, washed with water and brine, dried (sodium sulfate), concentrated, and purified by chromatography (ethyl acetate:hexane 1:3, then ethyl acetate:hexane 2:3) to give the title compound (1.82 g, 87%). $^1$H NMR (300 MHz, CDCl$_3$) δ8.15 (m, 2H), 7.76 (m, 2H), 7.62 (m, 1H), 7.52 (m, 3H), 7.40 (m, 7H), 6.93 (d, J=9.3 Hz, 1H), 6.29 (s, 1H), 6.29 (t,J=9.1 Hz, 1H), 6.05 (dd, J=2.6 and 9.3 Hz, 1H), 5.69 (d, J=7.0 Hz, 1H), 5.44 (d, J=2.8 Hz, 1 1H), 4.97 (d, J=8.2 Hz, 1H), 4.78 (AB q, J=11.9 Hz, Δv$_{AB}$=17.8 Hz, 2H), 4.43 (d, J=6.6 and 10.8 Hz, 1H), 4.31 (d, J=8.4 Hz, 1H), 4.20 (d, J=8.4 Hz, 1H), 3.82 (d, J=7.0 Hz, 1H), 2.55 (m, 1H), 2.47 (m, 1H), 2.22 (s, 3H), 2.22 (m, 1H), 1.91 (s, 3H), 1.91 (m, 1H), 1.68 (s, 3H), 1.14 (s, 3H). $^{13}$C NMR (75 MHz, CDCl$_3$) δ203.7, 171.2, 169.9, 167.3, 167.2, 167.0, 153.3, 142.3, 136.4, 133.6, 133.4, 133.0, 132.1, 130.2, 129.2, 128.7, 127.2, 126.6, 93.9, 84.4, 81.1, 79.1, 77.6, 77.2, 76.4, 75.5, 75.1, 72.4, 72.1, 58.5, 52.7, 45.6, 43.2, 35.5, 29.7, 26.8, 22.7, 22.1, 20.1, 14.7, 9.6. LRMS (APIMS) m/z 1028 (MH$^+$), 1046 (M+NH$_4^+$).

1b. 15-((3 S,2R)-3-phenyl-3-(phenylcarbonylamino)-2-(2,2,2-trichloroethoxy carbonyloxy) propanoyloxy)(2S,4S,9S,10S,15S,7R, 12R)-4,12-diacetyloxy-1-hydroxy-10,14,17,17-tetramethyl-6-oxa-11-oxo-2-phenylcarbonyloxytetracyclo(11.3.1.0<3,10>0.0<4,7>)heptadec -13-en-9-yl 3-methyl-3-((2,4,6-trimethoxyphenyl) methylthio)butanoate To the product of Example 1a (2.38 g, 2.31 mmol) in methylene chloride (50 mL) was added 3-methyl-3-(2,4,6-trimethoxyphenylmethyl thio)butyric acid (2.41 g, 7.67 mmol), 4-dimethylaminopyridine (509 mg, 4.17 mmol), and then 1-(3-(dimethylamino)propyl)-3-ethylcarbodiimide hydrochloride (1.46 g, 7.61 mmol). The reaction mixture was stirred overnight at room temperature, washed with water, saturated sodium bicarbonate, 0.2 M citric acid, saturated sodium bicarbonate, and brine. The organic phase was dried (sodium sulfate), concentrated, and purified by chromatography twice (ethyl acetate:hexane 1:3) and (methanol:methylene chloride 1:99) to give the title compound (2.08 g, 67%). $^1$H NMR (300 MHz, CDCl$_3$) δ8.14 (m, 2H), 7.75 (m, 2H), 7.61 (m, 1H), 7.52 (m, 3H), 7.40 (m, 7 H), 6.94 (d, J=9.3 Hz, 1H), 6.28 (s, 1H), 6.26 (t, J=9.3 Hz, 1 H), 6.10 (s, 2H), 6.05 (dd, J=2.6 and 9.3 Hz, 1H), 5.68 (m, 2H), 5.56 (d, J=2.8 Hz, 1H), 4.97 (d, J=8.2 Hz, 1H), 4.78 (AB q, J=11.0 Hz, Δv$_{AB}$=17.8 Hz, 2H), 4.34 (d, J=8.4 Hz, 1H), 4.29 (d, J=8.4 Hz, 1H), 3.98 (d, J=6.8 Hz, 1H), 3.82 (s, 6H), 3.79 (s, 2H) 3.78 (s, 3H), 2.71 (s, 2H), 2.67 (m, 1H), 2.47 (s, 3H), 2.42 (m, 1H), 2.22 (m, 1H), 2.14 (s, 3H), 2.00 (s, 3H), 1.92 (m, 1H), 1.83 (s, 3H), 1.47 (s, 3H), 1.41 (s, 3H), 1.21 (s, 3H), 1.17 (s, 3H). $^{13}$C NMR (75 MHz, CDCl$_3$) δ201.9, 170.0, 169.6, 168.6, 167.4, 167.0, 166.9, 160.2, 158.6, 153.2, 140.9, 136.4, 133.7, 133.5, 132.7, 132.0, 130.2, 129.2, 129.1, 128.7, 127.1, 126.6, 107.7, 93.9, 90.7, 84.1, 81.0, 78.6, 77.5, 77.2, 76.3, 75.2, 74.6, 72.3, 71.4, 56.0, 55.7, 55.3, 52.8, 47.0, 46.6, 43.8, 43.3, 35.3, 33.2, 28.7, 28.0, 26.5, 22.7, 21.2, 20.8, 20.6, 14.5, 10.9. LRMS (APIMS) m/z 1341 (M+NH$_4^+$).

1c. 5-((3S,2R)-3-phenyl-3-(phenylcarbonylamino)-2-(2,2,2-trichloroethoxycarbonyloxy)propanoyloxy)(2S,4S,9S,10S,15S,7R,12R)-4,12-diacetyloxy-1-hydroxy-10,14,17,17-tetramethyl-6-oxa 11-oxo-2-phenylcarbonyloxytetracyclo (11.3.1.0<3,10>0.0<4,7>)heptadec-13-en-9-yl 3-methyl-3-sulfanylbutanoate L-Cysteine (7.21 g, 59.5 mmol) was dissolved in formic acid (100 mL). The product from Example 1b (1.64 g, 1.23 mmol) in methylene chloride (100 mL) was slowly added at room temperature to give a colorless solution. The reaction mixture was stirred at room temperature for 40 min, concentrated to dryness, treated with ethyl acetate, and washed with saturated sodium bicarbonate (×3) and brine (×2). The organic phase was dried (sodium sulfate), concentrated, and purified by chromatography (ethyl acetate:hexane 1:4, then ethyl acetate:hexane 1:3) to give the title compound (1.31 g, 73%). $^1$H NMR (300 MHz, CDCl$_3$) δ8.13 (m, 2H), 7.75 (m, 2H), 7.62 (m, 1H), 7.50 (m, 3H), 7.39 (m, 7H), 6.94 (d, J=9.3 Hz, 1H), 6.26 (s, 1H), 6.26 (t, J=9.3 Hz, 1H), 6.05 (dd, J=2.7 and 9.3 Hz, 1H), 5.69 (d, J=6.9 Hz, 1H), 5.63 (dd, J=7.0 and 11.3 Hz, 1H), 5.55 (d, J=2.8 Hz, 1H), 4.96 (d, J=8.3 Hz, 1H), 4.78 (AB q, J=11.9 Hz, Δv$_{AB}$=17.8 Hz, 2h), 4.33 (d, J=8.4 Hz, 1H), 4.19 (d, J=8.4 Hz, 1H), 3.97 (d, J=6.8 Hz, 1H), 2.64 (m, 3H), 2.48 (s, 3H), 2.42 (m, 1H), 2.24 (m, 1H), 2.15 (s, 3H), 1.99 (s, 3H), 1.89 (m, 1H), 1.82 (s, 3H), 1.49 (s, 3H), 1.45 (s, 3H), 1.21 (s, 3H), 1.17 (s, 3H). $^{13}$C NMR (75 MHz, CDCl$_3$) δ201.9, 169.7, 169.6, 168.7, 167.4, 167.2, 166.9, 153.2, 140.9, 136.4, 133.7, 133.5, 132.7, 132.0, 130.2 129.2, 129.1, 128.7, 128.6, 127.1, 126.6, 93.8, 83.9, 80.9, 78.6, 77.5, 77.2, 76.3, 75.2, 74.5, 72.3, 71.6, 56.0, 52.7, 50.2, 46.9, 43.3, 41.7, 35.3, 33.4, 32.9, 32.3, 26.4, 22.6, 21.2, 20.7, 14.4, 10.9. LRMS (APIMS) m/z 1161 (M+NH$_4^+$).

1d. 15-((3 S,2R)-2-hydroxy-3-phenyl-3-(phenylcarbonylamino)propanoyloxy)(2S,4S,9S,10S,15S,7R,12R)-4,12-diacetyloxy-1-hydroxy-10,14,17,17-tetramethyl-6-oxa-11-oxo-2-phenylcarbonyloxytetracyclo (11.3.1.0<3,10>0.0<4,7>)heptadec-13-en-9-yl 3-methyl-3-sulfanylbutanoate To the product of Example 1c (1.24 g, 1.08 mmol) in methanol-acetic acid (9:1, 80 mL) was added zinc dust (4.53 g, 69.35 mmol). The reaction suspension was stirred at room temperature for 20 min. The zinc was removed by filtration. The filtrate was concentrated to dryness, treated with methylene chloride, and washed with water and brine. The organic phase was dried (sodium sulfate), concentrated, and purified by chromatography (ethyl acetate:hexane 1:3, then ethyl acetate:hexane 8:17) to give the title compound (1.04 g, 99%). $^1$H NMR (300 MHz, CDCl$_3$) δ8.11 (m, 2H), 7.76 (m, 2H), 7.62 (m, 1H), 7.50 (m, 3H), 7.39 (m, 7H), 7.07 (d, J=8.9 Hz, 1H), 6.21 (s, 1H), 6.18 (t, J=9.3 Hz, 1H), 5.81 (dd, J=2.1 and 9.0 Hz, 1H), 5.67 (d, J=6.8 Hz, 1H), 5.59 (dd, J=7.2 and 10.0 Hz, 1H), 4.95 (d, J=8.7 Hz, 1H), 4.79 (d, J=2.5 Hz, 1H), 4.32 (d, J=8.4 Hz, 1H), 4.19 (d, J=8.4 Hz, 1H), 3.93 (d, J=6.8 Hz, 1H), 3.62 (broad s, 1H) 2.64 (m, 3H), 2.38 (s, 3H), 2.34 (m, 2H), 2.16 (s, 3H), 1.89 (m, 1H), 1.85 (s, 3H), 1.83 (s, 3H), 1.49 (s, 3H), 1.45 (s, 3H), 1.20 (s, 3H), 1.17 (s, 3H). $^{13}$C NMR (300 MHz, CDCl$_3$) δ201.8, 172.4, 170.4, 169.9, 168.8, 166.9, 140.4, 138.0, 133.8, 133.7, 133.0, 131.9, 130.2, 129.1, 129.0, 128.7, 128.3, 127.1, 127.0, 83.9, 81.1, 78.5, 77.2, 75.3, 74.3, 73.3, 72.2, 71.7, 56.1, 54.9, 50.3, 47.1, 43.2, 41.8, 35.6, 33.5, 33.0, 32.4, 26.6, 22.5, 20.8, 14.7, 10.9. LRMS (APIMS) m/z 970 (MH$^+$), 987 (M+NH$_4^+$), 992 (M+Na$^+$).

1e. 15-((3 S,2R)-2-hydroxy-3-phenyl-3-(phenylcarbonylamino)propanoyloxy)(2S,4S,9S,10S,15S,7R,12R)-4,12-diacetyloxy-1-hydroxy-10,14,17,17-tetramethyl-6-oxa-11-oxo-2-phenylcarbonyloxytetracyclo(11.3.1.0<3,10>0.0<4,7>)heptadec-13-en-9-yl 3-methyl-3-(nitrosothio)butanoate To the product from Example 1d (659 mg, 0.68 mmol) in methylene chloride (8.5 mL) was added tert-butyl nitrite (120 μL of a 90% solution, 104 mg, 1.01 mmol) at room temperature. The reaction mixture was stirred at room temperature for 15 min, concentrated to dryness, and dissolved in methylene chloride. The methylene chloride solution was washed with water, and brine. The organic phase was dried (sodium sulfate), concentrated, and dried in vacuum to give the title compound (602 mg, 89%). $^1$H NMR (300 MHz, CDCl$_3$) δ8.09 (m, 2H), 7.75 (m, 2H), 7.61 (m, 1H), 7.49 (m, 3H), 7.37 (m, 7H), 7.12 (d, J=8.9 Hz, 1H), 6.19 (s, 1H), 6.16 (t, J=8.8 Hz, 1H), 5.79 (dd, J=2.0 and 8.7 Hz, 1H), 5.65 (d, J=6.8 Hz, 1H), 5.57 (dd, J=7.2 and 10.3 Hz, 1H), 4.91 (d, J=8.7 Hz, 1H), 4.78 (d, J=2.3 Hz, 1H), 4.30 (d, J=8.4 Hz, 1H), 4.17 (d, J=8.4 Hz, 1H), 3.90 (d, J=6.7 Hz, 1H), 3.25 (s, 2H) 2.52 (m, 1H), 2.36 (s, 3H), 2.31 (m, 2H), 2.16 (sm 3H), 1.99 (s, 3H), 1.95 (s, 3H), 1.88 (m, 1H), 1.82 (s, 3H), 1.77 (s, 3H), 1.19 (s, 3H), 1.15 (s, 3H), $^{13}$C NMR (75 MHz, CDCl$_3$) δ201.7, 172.3, 170.4, 169.2, 168.9, 167.0, 166.8, 140.4, 138.0, 133.7, 133.6, 132.9, 131.9, 130.1, 129.0, 128.9, 128.7, 128.3, 127.04, 127.02, 83.8, 81.0, 78.5, 76.4, 75.2, 74.2, 73.2, 72.1, 71.9, 56.0, 54.9, 53.6, 47.1, 47.0, 43.2, 35.5, 33.3, 29.5, 28.6, 26.5, 22.5, 20.7, 14.6, 10.8. LRMS (APIMS) m/z 999 (MH$^+$), 1016 (M+NH$_4^+$), 1021 (M+Na$^+$).

Example 2

(1S, 2S, 4S, 9S, 10S, 15S, 7R, 12R)-4,12-diacetyloxy-1,9-dihydroxy-10,14,17,17-tetramethyl-6-oxa-11-oxo-2-phenylcarbonyloxytetracyclo (11.3.1.0<3,10>0.0<4,7>)heptadec-13-en-15-yl(3S,2R)-2-(2-({N-(2-methyl-2-(nitrosothio)propyl)carbamoyl}methoxy)acetyloxy)-3-phenyl-3-(phenylcarbonylamino)propanoate 2a. 2-{(N-(2-methyl-2-sulfanylpropyl)carbamoyl) methoxy}acetic acid To an ice-cooled suspension of 1-amino-2-methyl-2-propanethiol hydrochloride (4.21 g, 29.72 mmol) in methylene chloride (50 mL) was added triethylamine (4.56 mL, 32.72 mmol) followed by diglycolic anhydride (3.43 g, 29.55 mmol). The solution was stirred at room temperature for 30 min and the reaction concentrated under vacuum. Cold 2N HCl (50 mL) was added to the residue and the mixture was extracted with ethyl acetate. The combined extracts were washed with brine and dried (sodium sulfate). Evaporation and trituration with ether/hexane gave the title compound as a white solid (5.50 g, 84%). mp. 81–82° C. $^1$H NMR (300 MHz, CDCl$_3$) δ8.80 (br s, 1H), 7.48 (br s, 1H), 4.24 (s, 2H), 4.20 (s, 2H), 3.41 (d, J=6.4 Hz, 2H), 1.59 (s, 1H), 1.38 (s, 6H). $^{13}$C NMR (75 MHz, CDCl$_3$) δ172.8, 170.4, 70.7, 68.3, 5.19, 44.9, 29.8. LRMS (APIMS) m/z 222 (MH$^+$), 239 (M+NH$_4^+$).

2b. 2-({N-(2-methyl-2-(nitrosothio)propyl)carbamoyl}methoxy)acetic acid

To a solution of the product from Example 2a (5.76 g, 26.03 mmol) in methylene chloride (100 mL) at room temperature was added tert-butyl nitrite (3.2 mL, 27.37 mmol). The reaction was stirred for 30 min, concentrated and a solid precipitated upon cooling. This was collected and washed with ether/hexane to give the title compound as a green solid (6.41 g, 98%). mp. 81–b 83° C. $^1$H NMR (300 MHz, CDCl$_3$) δ8.49 (br s, 1H), 7.28 (br s, 1H), 4.19 (s, 2H) 4.17 (s, 2H), 4.12 (d, J=6.5 Hz, 2H), 1.90 (s, 6H). $^{13}$C NMR (75 MHz, CDCl$_3$) δ173.0, 170.7, 70.9, 68.4, 56.7, 49.1, 26.7. LRMS (APIMS) m/z 251 (MH$^+$), 268 (M+NH$_4^+$). Anal. Calcd for C$_8$H$_{14}$N$_2$O$_5$S: C, 38.39; H, 5.64; N, 11.19; S,12.81, Found: C, 38.56; H,5.76; N, 10.88;S, 12.96. 239 (M+NH$_4^+$).

2c. (1S, 2S, 4S, 9S, 10S, 15S, 7R, 12R)-4,12-diacetyloxy-1,9-dihydroxy-10,14,17,17-tetramethyl-6-oxa-11-oxo-2-phenylcarbonyloxytetracyclo(11.3.1.0<3,10>0.0<4,7>) heptadec-13-en-15-yl(3S,2R)-2-(2-({N-(2-methyl-2-(nitrosothio)propyl)carbamoyl}methoxy)acetyloxy)-3-phenyl-3-(phenylcarbonylamino)propanoate To an ice-cooled solution of Paclitaxel (104 mg, 0.12 mmol), the product from Example 2b (36 mg, 0.15 mmol) and DMAP (1 mg) in methylene chloride (3 mL) was added dicyclohexylcarbodiimide (145 mg, 0.7 mmol). The ice bath was removed and the resulting solution was stirred at room temperature for 3 hr. The reaction was washed with 2N hydrochloric acid and dried (sodium sulfate). The solvent was removed under vacuum and the residue purified by chromatography (ethyl acetate:hexane 2:1) to give the title compound as a pale green powder (56 mg, 42%). $^1$H NMR (300 MHz, CDCl$_3$) δ8.14 (d, J=8.5 Hz, 2H), 7.72 (d, J=8.4 Hz, 2H), 7.60 (br t, J=7.3 Hz, 1H), 7.44 (m, 10H), 7.01 (br t, J=6.2 Hz, 1H), 6.91 (d, J=9.3 Hz, 1H), 6.30 (s, 1H), 6.25 (t, J=8.2 Hz, 1H), 6.03 (dd, J=9.2 and 3.2 Hz, 1H), 5.65 (d, J=7.0 Hz, 1H), 5.60 (d, J=3.4 Hz, 1H), 4.97 (br d, J=9.4 Hz, 1H), 4.29 (m, 10H), 3.82 (d, J=6.9 Hz, 1H), 2.57 (m, 1H), 2.54 (d, J=4.3 Hz, 1H), 2.46 (s, 3H), 2.37 (m, 1H), 1.92 (m, 1H), 1.92 (s, 3H), 1.91 (s, 1H), 1.86 (s, 6H), 1.68 (s, 3H), 1.23 (s, 3H), 1.14 (s, 3H). $^{13}$C NMR (75 MHz, CDCl$_3$) δ203.7, 171.2, 169.8, 169.0, 168.9, 167.5, 167.1, 167.0, 142.3, 136.4, 133.6, 133.4, 133.0, 132.1, 130.2, 129.2, 128.7, 128.7, 127.1, 126.4, 84.4, 81.1, 79.1, 76.4, 75.5, 75.1, 74.6, 72.1, 72.1, 71.5, 71.0, 68.0, 58.5, 56.9, 55.6, 52.6, 50.0, 48.9, 45.6, 43.2, 35.5, 32.6, 30.8, 26.8, 26.1, 25.3, 25.2, 24.6, 22.7, 22.1, 20.8, 14.7, 9.6. LRMS (APIMS) m/z 1104 (M+NH$_4^+$).

Example 3

9-(2-({((2R)-2,3-bis(nitrooxy)propyl) oxycarbonyl}methoxy)acetyloxy)(1S,2S,4S,9S,10S, 15S,7R,12R)-4,12-diacetyloxy-1-hydroxy-10,14,17, 17-tetramethyl-6-oxa-11-oxo-2-phenylcarbonyloxytetracyclo(11.3.1.0<3,10>0.0<4, 7>)heptadec-13-en-15-yl 2-(2-({((2R)-2,3-bis (nitrooxy)propyl)oxyccarbonyl}methoxy)acetyloxy) (3S,2R)-3-phenyl-3-(phenylcarbonylamino) propanoate 3a. 2-(({15-((3S,2R)-2-{((oxycarbonyl) methoxy)acetic acid}-3-phenyl-3-(phenylcarbonylamino)propanoyloxy)

(1S,2S,4S,9S,10S,15S,7R,12R)-4,12-diacetyloxy-1-hydroxy-10,14,17,17-tetramethyl-6-oxa-11-oxo-2-phenylcarbonyloxytetracyclo(11.3.1.0<3,10>0.0<4,7>)heptadec-13-en-9-yl}oxycarbonyl)methoxy)acetic acid To (1S,2S,4S,9S,10S,15S,7R,12R)-4,12-diacetyloxy-1,9-dihydroxy-10,14,17,17-tetramethyl-6-oxa-11-oxo-2-phenylcarbonyloxytetracyclo(11.3.1.0<3,10>0.0<4,7<)heptadec-13-en-15-yl(3S,2R)-2-hydroxy-3-phenyl-3-(phenylcarbonylamino)propanoate (233.3 mg, 0.2732 mmol) and diglycolic anhydride (243.4 mg, 2.097 mmol) was added pyridine (1.5 mL) and 4-dimethylaminopyridine (5 mg, 0.04 mmol) at room temperature. The reaction mixture was stirred for 40 hours at room temperature, concentrated to dryness, diluted with methylene chloride, and washed with 0.2M citric acid twice and brine once. The organic phase was dried over sodium sulfate. During drying the solution become cloudy. The suspension was decanted. The sodium sulfate was washed with methylene chloride three times. The combined suspension was filtered to give the title compound (98.8 mg, 0.0910 mmol, 33%). The filtrate was concentrated to give more crude title compound (165.2 mg, 0.1521 mmol, 56%). $^1$HNMR (CDCl$_3$) δ8.14–8.12 (m, 2H), 7.82–7.80 (m, 2H), 7.67–7.64 (m, 1H), 7.61–7.56 (m, 3H), 7.53–7.43 (m, 7H), 7.31 (m, 1H), 6.26 (s, 1H), 6.13 (t, J=8.8 Hz, 1H), 5.92 (d, J=5.2 Hz, 1H), 5.69 (dd, J=6.9 & 10.2 Hz, 1H), 5.65 (d, J=6.9 Hz, 1H), 5.59 (d, J=5.3 Hz, 1H), 5.02 (d, J=8.5 Hz, 1H), 4.35 (s, 2H), 4.25–4.20 (m, 2H), 4.18–4.14 (m, 4H), 4.03 (s, 2H), 3.93 (d, J=7.1 Hz, 1H), 2.65–2.55 (m, 1H), 2.45 (s, 3H), 2.32–2.24 (m, 1H), 2.15 (s, 3H), 2.02–1.97 (m, 1H), 1.94 (s, 3H), 1.87–1.83 (m, 1H), 1.78 (s, 3H), 1.15 (s, 3H), 1.11 (s, 3H). LRMS (APIMS) m/z 1086 (MH$^+$), 1103 (M+NH$_4^+$), 1108 (M+Na$^+$).

3b. 9-(2-({((2R)-2,3-bis(nitrooxy)propyl)oxycarbonyl}methoxy)acetyloxy)(1S,2S,4S,9S,10S,15S, 7R, 12R)-4,12-diacetyloxy-1-hydroxy-10,14,17,17-tetramethyl-6-oxa-11-oxo-2-phenylcarbonyloxytetracyclo(11.31.0<3,10>0.0<4,7>)heptadec-13-en-15-yl 2-(2-({((2R)-2,3-bis(nitrooxy)propyl)oxycarbonyl}methoxy)acetyloxy)(3S,2R)-3-phenyl-3-(phenylcarbonylamino)propanoate To Example 3a (53.3 mg, 0.0491 mmol) and 4-dimethylaminopyridine (13.9 mg, 0.114 mmol) in methylene chloride (1 mL) was added (2R)-2,3-bis(nitrooxy)propan-1-ol (58 μL, 88.7 mg, 0.487 mmol) and then 1-(3-(dimethylamino)propyl)-3-ethylcarbodiimide hydrochloride (96.1 mg, 0.501 mmol). The reaction mixture was stirred at room temperature overnight, diluted with methylene chloride, washed with water, 0.2 M citric acid and brine. The organic phase was dried over sodium sulfate, filtered, concentrated, and purified by chromatography (ethyl acetate:hexane 35:65, then ethyl acetate:hexane 40:60, then ethyl acetate:hexane 45:55, then ethyl acetate:hexane 50:50) to give the title compound (52.6 mg, 0.0372 mmol, 76%). $^1$H NMR (CDCl$_3$) δ8.14–8.11 (m, 2H), 7.77–7.75 (m, 2H), 7.64–7.59 (m, 1H), 7.53–7.48 (m, 3 H), 7.46–7.35 (m, 7H), 7.11 (d, J=9.2 Hz, 1H), 6.23–6.17 (m, 2H), 6.03 (dd, J=2.9 & 9.3 Hz, 1H), 5.70–5.65 (m, 2H), 5.63 (d, J=3.1 Hz, 1H), 5.54–5.47 (m, 1H), 5.47–5.41 (m, 1H), 4.96 (d, J=8.7 Hz, 1H), 4.86–4.75 (m, 2H), 4.75–4.62 (m, 2H), 4.62–4.38 (m, 4H), 4.38–4.26 (m, 6H), 4.26–4.14 (m, 4H), 3.94 (d, J=6.8 Hz, 1H), 2.65–2.55 (m, 1H), 2.46 (s, 3H), 2.40–2.35 (m, 1H), 2.28–2.20 (m, 1H), 2.15 (s, 3H), 1.97 (s, 3H), 1.91–1.80 (m, 1H), 1.80 (s, 3H), 1.21 (s, 3H), 1.14 (s, 3H). $^{13}$C NMR (CDCl$_3$) δ201.9, 169.8, 169.6, 169.37, 169.34, 169.0, 168.9, 167.8, 167.2, 166.9, 141.2, 136.6, 133.8, 133.6, 132.5, 132.1, 130.2, 129.2, 129.1, 128.75, 128.71, 128.63, 127.2, 126.6, 83.8, 80.8, 78.7, 77.2, 76.3, 76.1, 75.9, 75.3, 74.4, 74.3, 72.2, 72.1, 68.6, 68.4, 67.9, 67.7, 67.6, 61.0, 60.7, 55.9, 52.7, 46.9, 43.2, 35.4, 33.3, 26.4, 22.6, 21.2, 20.7, 14.5, 10.8. LRMS (APIMS) m/z 1414 (MH$^+$), 1431 (M+NH$_4^+$), 1436 (M+Na$^+$).

Example 4

(1S,2S,4S, 9S,10S,15S,7R,12R)-4,12-diacetyloxy-9-{2-(({2,2-bis((nitrooxy)methyl)-3-(nitrooxy)propyl}oxycarbonyl)methoxy)acetyloxy}-1-hydroxy-10,14,17,17-tetramethyl-6-oxa-11-oxo-10, 14,17,17-tetramethyl-6-oxa-11-oxo-2-phenylcarbonyloxytetracyclo(11.3.1.0<3,10>0.0<4, 7>)heptadec-13-en-15-yl(3S,2R)-2-{2-(({2,2-bis ((nitrooxy)methyl)-3-(nitrooxy)propyl}oxycarbonyl) methoxy)acetyloxy}-3-phenyl-3-(phenylcarbonylamino)propanoate To Example 3a (53.7 mg, 0.0494 mmol) and 4-(dimethylamino)pyridine (66.9 mg, 0.247 mmol) in methylene chloride (1 mL) was added 2,2-bis((nitrooxy)methyl)-3-(nitrooxy)propan-1-ol (NMI 609, 66.9 mg, 0.247 mmol) and then 1-(3-(dimethylamino)propyl)-3-ethylcarbodiimide hydrochloride (65.7 mg, 0.538 mmol). The reaction mixture was stirred at room temperature overnight, diluted with methylene chloride, washed with water, 0.2 M citric acid and brine. The organic phase was dried over sodium sulfate, filtered, concentrated, and purified by chromatography (ethyl acetate:hexane 35:65, then ethyl acetate:hexane 40:60) to give the title compound (51.0 mg, 0.0320 mmol, 65%). $^1$H NMR (CDCl$_3$) δ8.13–8.11 (m, 2H), 7.77–7.75 (m, 2H), 7.64–7.59 (m, 1H), 7.54–7.46 (m, 3H), 7.46–7.35 (m, 7H), 7.02 (d, J=9.3 Hz, 1H), 6.23–6.17 (m, 2H), 6.02 (dd, J=2.4 & 9.4 Hz, 1H), 5.69–5.64 (m, 2H), 5.63 (d, J=3.2 Hz, 1H), 4.96 (d, J=8.7 Hz, 1H), 4.60 (s, 6H), 4.51 (s, 6H), 4.36–4.25 (m, 7H), 4.25–4.15 (m, 7H), 3.92 (d, J=6.7 Hz, 1H), 2.66–2.55 (m, 1H), 2.45 (s, 3H), 2.40–2.33 (m, 1H), 2.29–2.21 (m, 1H), 2.15 (s, 3H), 1.97 (s, 3H), 1.91–1.82 (m, 1H), 1.79 (s, 3H), 1.21 (s, 3H), 1.15 (s, 3H). $^{13}$C NMR (CDCl$_3$) δ201.9, 169.8, 169.6, 169.41, 169.37, 168.9, 168.8, 167.9, 167.2, 166.9, 141.1, 136.6, 133.8, 133.5, 132.5, 132.0, 130.2, 129.2, 129.0, 128.73, 128.68, 128.62, 127.2, 126.6, 83.7, 80.8, 78.6, 77.2, 76.3, 75.2, 74.3, 72.3, 72.1, 69.3, 69.2, 68.0, 67.84, 67.78, 62.0, 61.6, 55.9, 52.7, 47.0, 43.2, 42.2, 42.0, 35.3, 33.2, 26.3, 22.5, 21.1, 20.7, 14.5, 14.2, 10.8. LRMS (APIMS) m/z 1609 (M+NH$_4^+$), 1614 (M+Na$^+$).

Example 5

Vascular Smooth Muscle Cell (SMC) Antiproliferation Assay

The cells used in this assay were human coronary artery smooth muscle cells (CASMC) supplied by Clonetics Corp. (San Diego, Calif.). They were maintained in SmGM-2 growth medium (Clonetics Corp.), which consisted of modified MCDB 131 medium supplemented with 5% (v/v) fetal bovine serum (FBS), 0.5 ng/mL human recombinant epidermal growth factor (EGF), 2 ng/mL human recombinant fibroblast growth factor (FGF), 5 μg/mL bovine insulin, 50 μg/mL gentamicin sulfate, and 50 ng/mL amphotericin B under humidified 95% air-5% CO$_2$ at 37° C. Cells were used for experiments up to about 17 cumulative population doublings (i.e., passage 9); at this age they still stained positive for smooth muscle actin, a protein marker for smooth muscle cells.

For the SMC antiproliferation assay, the cells were seeded at 3×10$^4$ viable cells in 2 mL of SmGM-2 medium per well of a Corning 24 well plate (Corning, N.Y.). Stock solutions of the test compounds were prepared just prior to addition to the cells by dissolving in ethanol at a concentration of 40 mM. This stock solution was diluted, as required, with ethanol to lower concentrations. On the same day the cells were seeded, but after they had attached and spread out (about 3 hr), each test compound in varying concentrations (2 $\mu$L of the diluted stock solutions) was added to four replicate wells (n=4) for each concentration. Control cultures received 2 $\mu$L of ethanol per well (n=4). On the following morning, the cultures were examined microscopically and their condition recorded. On the third day after test compound addition (~68 hr), the cultures were examined microscopically again and the viable cells counted with an hemacytometer following trypsinization with 0.25% trypsin-1mM EDTA. Trypan Blue dye exclusion was used to discriminate between viable and dead cells. The results were usually presented as % of the control viable cell count (mean±SEM).

Example 6

Suppression of Proliferation of Human Coronary Artery Smooth Muscle Cells (CASMC) to Paclitaxel, Example 1 and Example 1d The SMC antiproliferation assay was performed as described in Example 5. The paclitaxel nitrosothiol compound (Example 1) was superior to its non-nitrosylated derivative (Example 1d) in inhibiting the proliferation of vascular smooth muscle cells. These results are shown in FIG. 1. In particular, FIG. 1 shows the dose response curve of Coronary Artery Smooth Muscle Cells of the compound from paclitaxel, Example 1 (nitrosylated paclitaxel derivative) and Example 1d (sulfhydryl paclitaxel derivative). Paclitaxel at a concentration of 0.01 $\mu$M ($10^{-8}$ and higher) totally suppressed cell proliferation of the seeded cells; both Example 1 and Example 1d also totally suppressed cell proliferation, but at the higher concentration of 0.1 $\mu$M ($10^{-7}$) (FIG. 1). At high concentrations up to 10 $\mu$M (the upper limit of solubility for these compounds), there was no increase in the level of cell proliferation suppression and no difference in suppression between the three compounds (data not shown).

Example 7

Effect of Paclitaxel, Example 1 and Example 1d on Aggregation of Rabbit Platelets Rabbit Platelet Aggregation Assay Blood was collected from New Zealand White rabbits into a sodium citrate solution. Platelet-rich plasma (PRP) and platelet-poor plasma (PPP) were obtained by centrifugation of the citrated blood. Aggregation of the platelets, which was induced by addition of adenosine diphosphate (ADP), was measured in a Chrono-Log Aggregometer (Havertown, Pa.). Stock solutions of the test compounds were prepared in ethanol at concentrations 1000-fold higher than the final concentrations. The test compounds at these different concentrations were pre-incubated with the PRP for 2 min with stirring prior to the addition of ADP. Inhibition of aggregation was quantified as follows:

% Inhibition=100% (1-(Max. Ampl. Agg. in Test Compound/Max. Ampl. Agg. Control))

"Max. Ampl. In Test Compound" was the measured maximum amplitude of the platelets in the PRP in the presence of and after pre-incubation with the test compound.

"Max. Ampl. Agg. Control" was the measured maximum amplitude of the platelets in the PRP without test compound addition.

Figure 2:
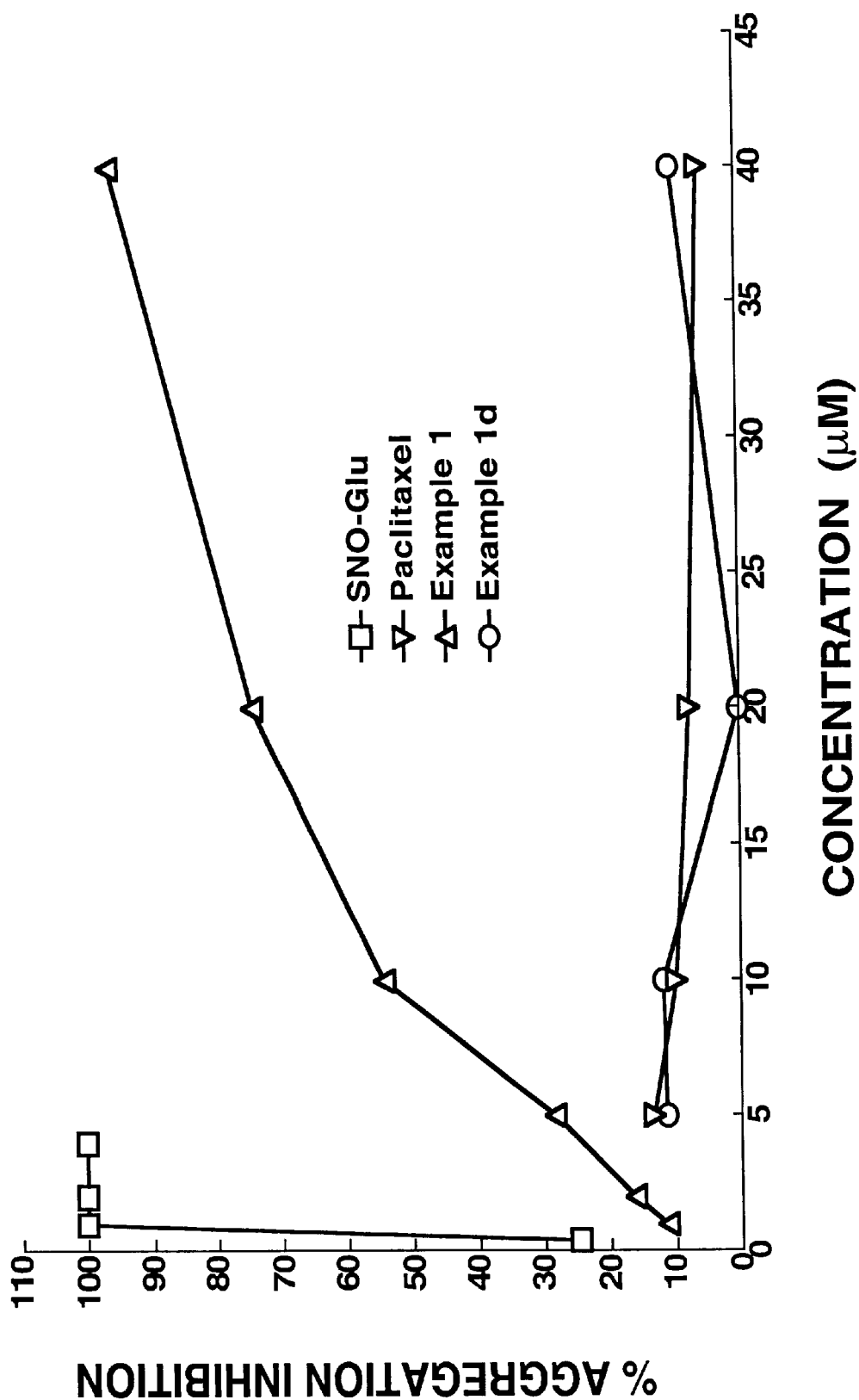
FIG. 2 is a dose response curve of the inhibition of platelet aggregation by paclitaxel (open inverted triangles), Example 1 (open triangles, nitrosylated paclitaxel derivative) and Example 1d (open circles, sulfhydryl paclitaxel derivative) and S-nitrosoglutathione (open squares).

Nitric oxide inhibits the aggregation of platelets whether added as the gas or in the form of a NO donor. As shown in FIG. 2, S-Nitrosoglutathione (SNO-Glu) totally inhibited platelet aggregation at a final concentration of 1 $\mu$M. Example 1 also inhibited platelet aggregation, but required higher concentrations than SNO-Glu. Paclitaxel and Example 1d did not prevent platelet aggregation even at these higher concentrations. These results indicate that the inhibition of platelet aggregation by Example 1 was attributable to the presence of the NO moiety.

Example 8

Suppression of Proliferation of Human Coronary Artery Smooth Muscle Cells (CASMC) to Paclitaxel, Example 3 and Example 4

The SMC antiproliferation assay was performed as described in Example 5. The paclitaxel nitrosated compound (Example 3 and Example 4) was superior to paclitaxel in inhibiting the proliferation of vascular smooth muscle cells. These results are shown in FIG. 3. In particular, FIG. 3 shows the dose response curve of Coronary Artery Smooth Muscle Cells of the compound from paclitaxel, Example 3 and Example 4 (nitrosated paclitaxel derivative). Paclitaxel at a concentration of 0.01 $\mu$M ($10^{-8}$ and higher) totally suppressed cell proliferation of the seeded cells; both Example 3 and Example 4 also totally suppressed cell proliferation, but at the higher concentration of 1 $\mu$M ($10^{-6}$) (FIG. 3).

The disclosure of each patent, patent application and publication cited or described in the specification is hereby incorporated by reference herein in its entirety.

Although the invention has been set forth in detail, one skilled in the art will appreciate that numerous changes and modifications may be made without departing from the spirit and scope of the present invention.

What is claimed is:

1. A taxane compound comprising at least one NO group, or at least one NO and $NO_2$ group, or a pharmaceutically acceptable salt thereof, wherein the at least one NO group or the at least one NO and $NO_2$ group is linked to the taxane compound through an oxygen atom, a nitrogen atom or a sulfur atom.

2. A compound of formula (I), or a pharmaceutically acceptable salt thereof, wherein the compound of formula (I) is:

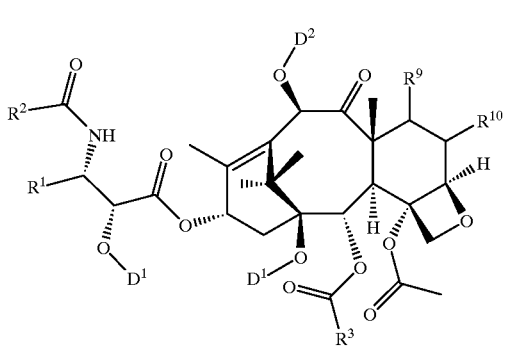

I wherein:

$R^1$ is:

(a) 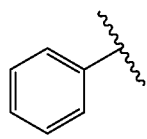

(b) 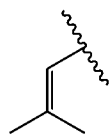

(c) 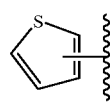

(d) 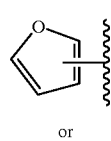

or (e) 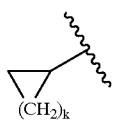

$R^2$ is:

(a) 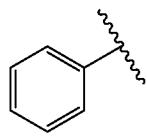

(b) 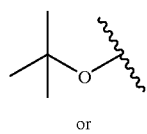

or (c) 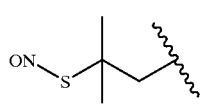

$R^3$ is:

(a) 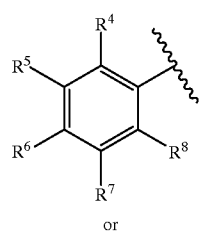

or (b) 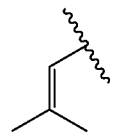

$R^4$, $R^5$, $R^6$, $R^7$ and $R^8$ are each independently a hydrogen, a lower alkyl group, an alkenyl, an alkynyl, an alkoxy, a halo, a haloalkyl, a nitro or an amino;

$R^9$ and $R^{10}$ are each independently a hydrogen, —$OD^1$, —$SD^1$ or a halo;

$D^1$ is a hydrogen or D;

$D^2$ is a hydrogen, —C(O)CH$_3$ or D;

D is Q or K;

Q is —NO or —NO$_2$;

K is —$W_a$—$E_b$—$(C(R_e)(R_f))_p$—$E_c$—$(C(R_e)(R_f))_x$—$W_d$—$(C(R_e)(R_f))_y$—$W_i$—$E_j$—$W_g$—$(C(R_e)(R_f))_z$—T—Q a, b, c, d, g, i and j are each independently an integer from 0 to 3;

p, x, y and z are each independently an integer from 0 to 10;

W at each occurrence is independently —C(O), —C(S), —T—, —$(C(R_e)(R_f))_h$, an alkyl group, an aryl group, a heterocyclic ring, an arylheterocyclic ring, or —$(CH_2CH_2O)_q$;

E at each occurrence is independently —T—, an alkyl group, an aryl group, —$(C(R_e)(R_f))_h$, a heterocyclic ring, an arylheterocyclic ring, or —$(CH_2CH_2O)_q$;

h is an integer form 1 to 10;

q is an integer from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a urea, a phosphoryl, a nitro, $W_h$, —T—Q , or —$(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group;

k is an integer from 1 to 3;

T at each occurrence is independently a covalent bond, a carbonyl, an oxygen, —S(O)$_o$— or —N($R_a$)$R_i$;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T$—$Q)(R_e)(R_f)$, or —$(N_2O_2$—$)^-·M^+$, wherein $M^+$ is an organic or inorganic cation; with the proviso that the compounds of Formula (I) must contain at least one NO group, or at least one $NO_2$ group wherein the at least one NO group or the at least one NO and $NO_2$ group is linked to the compound of Formula (I) through an oxygen atom, a nitrogen atom or a sulfur atom; and —$OD^1$ and —$OD^2$ are not —O—$NO_2$; $R^9$ is not —O—$NO_2$ or the $D^1$ group at $R^9$ does not contain a nitroaryl group or a nitroxyloside group; and $R^{10}$ is not —O—$NO_2$.

3. The compound of claim 2, wherein the compound of Formula (I) is a nitrosated paclitaxel, a nitrosylated paclitaxel, a nitrosated and nitrosylated paclitaxel, a nitrosated docetaxel, a nitrosylated docetaxel, a nitrosated and nitrosylated docetaxel, a nitrosated baccatin III, a nitrosylated III or a nitrosated and nitrosylated baccatin III.

4. A composition comprising the compound of claim 2 and a pharmaceutically acceptable carrier.

5. A method for treating or preventing a cardiovascular disease or disorder in a patient in need thereof comprising administering a therapeutically effective amount of the composition of claim 4.

6. The method of claim 5, wherein the cardiovascular disease or disorder is restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications associated with the use of medical devices, wounds associated with the use of medical devices, myocardial infarction, pulmonary thromboembolism, cerebral thromboembolism, thrombophiebitis, thrombocytopenia or bleeding disorders.

7. The method of claim 6, wherein the cardiovascular disease or disorder is restenosis or atherosclerosis.

8. A method for treating or preventing an autoimmune disease, a pathological condition resulting from abnormal cell proliferation, polycyctic kidney disease, an inflammatory disease, for preserving an organ and/or a tissue or for inhibiting wound contraction in a patient in need thereof comprising administering a therapeutically effective amount of the composition of claim 4.

9. The method of claim 8, wherein the pathological condition resulting from abnormal cell proliferation is a cancer, a Karposi's sarcoma, a cholangiocarcinoma, a choriocarcinoma, a neoblastoma, a Wilm's tumor, Hodgkin's disease, a melanoma, multiple myelomas, a chronic lymphocytic leukemia or an acute or chronic granulocytic lymphoma.

10. The method of claim 8, wherein the inflammatory disease is rheumatoid arthritis, an inflammatory skin disease, restenosis, multiple sclerosis, a surgical adhesion, tuberculosis, a graft rejection, an inflammatory lung disease, an inflammatory bowel disease, an inflammatory disease that affects or causes obstruction of a body passageway, an inflammation of the eye, an inflammation of the nose, an inflammation of the throat or a neovascular disease of the eye.

11. The method of claim 5 or 8, wherein the compound is administered intravenously, orally, bucally, parenterally, by an inhalation spray, by topical application or transdermally.

12. The method of claim 5 or 8, wherein the composition is administered via local administration.

13. The method of claim 12, wherein the local administration of the compound is via a suture, a vascular implant, a stent, a heart valve, a drug pump, a drug delivery catheter, an infusion catheter, a drug delivery guidewire or an implantable medical device.

14. A method for delivering nitric oxide to a targeted site in a patient in need thereof comprising administering the composition of claim 4 to the targeted site in the patient.

15. The method of claim 14, wherein the composition provides sustained delivery of nitric oxide to the targeted sited in the patient.

16. A composition comprising the compound of claim 2 and at least one therapeutic agent.

17. The composition of claim 16, wherein the therapeutic agent is a antithrombogenic agent, a thrombolytic agent, a fibrinolytic agent, a vasospasm inhibitor, a potassium channel activator, a calcium channel blocker, an antihypertensive agent, an antimicrobial agent, an antibiotic, an antiplatelet agent, an antimitotic agent, an antiproliferative agent, a microtubule inhibitor, an antisecretory agent, a remodelling inhibitor, an antisense nucleotide, an anti-cancer chemotherapeutic agent, a steroid, a non-steroidal antiinflammatory agent, a selective COX-2 inhibitor, an immunosuppressive agent, a growth factor antagonist or antibody, a dopamine agonist, a radiotherapeutic agent, a heavy metal functioning as a radioplaque agent, a biologic agent, an angiotensin converting enzyme inhibitor, an angiotensin II receptor antagonist, a renin inhibitor, a free radical scavenger, an iron chelator, an antioxidant, a sex hormone, an antipolymerase, an antiviral agent, a photodynamic therapy agent, an antibody targeted therapy agent, a gene therapy agent, or a mixture thereof.

18. A method for treating or preventing a cardiovascular disease or disorder in a patient in need thereof comprising administering a therapeutically effective amount of the composition of claim 16.

19. The method of claim 18, wherein the cardiovascular disease or disorder is restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications associated with the use of medical devices, wounds associated with the use of medical devices, myocardial infarction, pulmonary thromboembolism, cerebral thromboembolism, thrombophiebitis, thrombocytopenia or bleeding disorders.

20. The method of claim 18, wherein the cardiovascular disease or disorder is restenosis or atherosclerosis.

21. A method for treating or preventing an autoimmune disease, a pathological condition resulting from abnormal cell proliferation, polycyctic kidney disease, an inflammatory disease, for preserving an organ and/or a tissue or for inhibiting wound contraction in a patient in need thereof comprising administering a therapeutically effective amount of the composition of claim 16.

22. The method of claim 21, wherein the pathological condition resulting from abnormal cell proliferation is a cancer, a Karposi's sarcoma, a cholangiocarcinoma, a choriocarcinoma, a neoblastoma, a Wilm's tumor, Hodgkin's disease, a melanoma, multiple myelomas, a chronic lymphocytic leukemia or an acute or chronic granulocytic lymphoma.

23. The method of claim 21, wherein the inflammatory disease is rheumatoid arthritis, an inflammatory skin disease, restenosis, multiple sclerosis, a surgical adhesion, tuberculosis, a graft rejection, an inflammatory lung disease, an inflammatory bowel disease, an inflammatory disease that affects or causes obstruction of a body passageway, an inflammation of the eye, an inflammation of the nose, an inflammation of the throat or a neovascular disease of the eye.

24. The method of claim 18 or 21, wherein the compound is administered intravenously, orally, bucally, parenterally, by an inhalation spray, by topical application or transdermally.

25. The method of claim 18 or 21, wherein the composition is administered via local administration.

26. The method of claim 25, wherein the local administration of the compound is via a suture, a vascular implant, a stent, a heart valve, a drug pump, a drug delivery catheter, an infusion catheter, a drug delivery guidewire or an implantable medical device.

27. A method delivering nitric oxide to a targeted site in a patient in need thereof comprising administering the composition of claim 16 to the targeted site in the patient.

28. The method of claim 27, wherein the composition provides sustained delivery of nitric oxide to the targeted sited in the patient.

29. A composition comprising at least one compound of claim 2 or a pharmaceutically acceptable salt thereof and at least one compound that donates, transfers, or releases nitric oxide, or induces the production of endogenous nitric oxide or endothelium-derived relaxing factor or is a substrate for nitric oxide synthase or a pharmaceutically acceptable salt thereof.

30. The composition of claim 29, wherein the at least one compound that donates, transfers, or releases nitric oxide, or induces the production of endogenous nitric oxide or endothelium-derived relaxing factor or is a substrate for nitric oxide synthase is an S-nitrosothiol.

31. The composition of claim 30, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

32. The composition of claim 30, wherein the S-nitrosothiol is:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, an alkoxy, a haloalkoxy, an amino, an alkylamino, a dialkylamino, an arylamino, a diarylamno, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an amninoaryl, an aryl, an alkylaryl, a carboxamido, a alkylcarboxamido, an arylcarboxamnido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, $W_h$, —T—Q , or —$(C(R_e)(R_f))_k$, or $R_e$ and $R_f$ taken together with the carbons to which they are attached form a carbonyl, a methanthial, a heterocyclic ring, a cycloalkyl group or a bridged cycloalkyl group; Q is —NO or —$NO_2$; and T is independently a covalent bond, a carbonyl, an oxygen, —$S(O)_o$— or —$N(R_a)R_i$, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T-Q)(R_e)(R_f)$, or —$(N_2O_2-)\cdot M^+$, wherein $M^+$ is an organic or inorganic cation; with the proviso that when $R_i$ is —$CH_2$—$C(T-Q)(R_e)(R_f)$ or —$(N_2O_2-)\cdot M^+$; then "—T—Q" can be a hydrogen, an alkyl group, an alkoxyalkyl group, an aminoalkyl group, a hydroxy group or an aryl group.

33. The composition of claim 29, wherein the at least one compound that donates, transfers, or releases nitric oxide, or induces the production of endogenous nitric oxide or endothelium-derived relaxing factor, or is a substrate for nitric oxide synthase is:

(i) a compound that comprises at least one ON—O—, ON—N—or ON—C—group;

(ii) a compound that comprises at least one $O_2N$—O—, $O_2N$—N—, $O_2N$—S—or —$O_2N$—C-group;

(iii) a N-oxo-N-nitrosoamine having the formula: $R^1R^2N-N(O-M^+)-NO$, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation.

34. The composition of claim 33, wherein the compound comprising at least one ON—O—, ON—N— or ON—C-group is an ON—O-polypeptide, an ON—N-polypepetide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

35. The composition of claim 33, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

36. The composition of claim 29, wherein the at least one compound that donates, transfers, or releases nitric oxide, or induces the production of endogenous nitric oxide or endothelium-derived relaxing factor, or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, polypeptides comprising at least one of these amino acids or inhibitors of the enzyme arginase.

37. The composition of claim 29, wherein the at least one compound that donates, transfers or releases nitric oxide, elevates endogenous levels of endothelium-derived relaxing factor, stimulates endogenous synthesis of nitric oxide or is a substrate for nitric oxide synthase is a NONOate.

38. The composition of claim 29, further comprising at least one therapeutic agent.

39. The composition of claim 38, wherein the therapeutic agent is a antithrombogenic agent, a thrombolytic agent, a fibrinolytic agent, a vasospasm inhibitor, a potassium channel activator, a calcium channel blocker, an antihypertensive agent, an antimicrobial agent, an antibiotic, an antiplatelet agent, an antimitotic agent, an antiproliferative agent, a microtubule inhibitor, an antisecretory agent, a remodelling inhibitor, an antisense nucleotide, an anti-cancer chemotherapeutic agent, a steroid, a non-steroidal antiinflammatory agent, a selective COX-2 inhibitor, an immunosuppressive agent, a growth factor antagonist or antibody, a dopamine agonist, a radiotherapeutic agent, a heavy metal functioning as a radioplaque agent, a biologic agent, an angiotensin converting enzyme inhibitor, an angiotensin II receptor antagonist, a renin inhibitor, a free radical scavenger, an iron chelator, an antioxidant, a sex hormone, an antipolymerase, an antiviral agent, a photodynamic therapy agent, an antibody targeted therapy agent, a gene therapy agent, or a mixture thereof.

40. A method for treating or preventing a cardiovascular disease or disorder in a patient in need thereof comprising administering a therapeutically effective amount of the composition of claim 29 or 38.

41. The method of claim 40, wherein the cardiovascular disease or disorder is restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications associated with the use of medical devices, wounds associated with the use of medical devices, myocardial infarction, pulmonary thromboembolism, cerebral thromboembolism, thrombophlebitis, thrombocytopenia or bleeding disorders.

42. The method of claim 41, wherein the cardiovascular disease or disorder is restenosis or atherosclerosis.

43. A method for treating or preventing an autoimmune disease, a pathological condition resulting from abnormal cell proliferation, polycyctic kidney disease, an inflammatory disease, for preserving an organ and/or a tissue or for inhibiting wound contraction in a patient in need thereof comprising administering a therapeutically effective amount of the composition of claim 29 or 38.

44. The method of claim 43, wherein the pathological condition resulting from abnormal cell proliferation is a cancer, a Karposi's sarcoma, a cholangiocarcinoma, a choriocarcinoma, a neoblastoma, a Wilm's tumor, Hodgkin's disease, a melanoma, multiple myelomas, a chronic lymphocytic leukemia or an acute or chronic granulocytic lymphoma.

45. The method of claim 44, wherein the inflammatory disease is rheumatoid arthritis, an inflammatory skin disease, restenosis, multiple sclerosis, a surgical adhesion, tuberculosis, a graft rejection, an inflammatory lung disease, an inflammatory bowel disease, an inflammatory disease that affects or causes obstruction of a body passageway, an inflammation of the eye, an inflammation of the nose, an inflammation of the throat or a neovascular diseases of the eye.

46. The method of claim 40, wherein the compound is administered intravenously, orally, bucally, parenterally, by an inhalation spray, by topical application or transdermally.

47. The method of claim 40, wherein the composition is administered via local administration.

48. The method of claim 47, wherein the local administration of the compound is via a suture, a vascular implant, a stent, a heart valve, a drug pump, a drug delivery catheter, an infusion catheter, a drug delivery guidewire or an implantable medical device.

49. A method for delivering nitric oxide to a targeted site in a patient in need thereof comprising administering the composition of claim 29 or 38 to the targeted site in the patient.

50. The method of claim 49, wherein the composition provides sustained delivery of nitric oxide to the targeted sited in the patient.

51. A composition comprising at least one compound of formula (I) or a pharmaceutically acceptable salt thereof, bound to a matrix;

wherein the matrix is a natural polymer, a synthetic polymer, a natural fiber, a synthetic fiber, or a mixture thereof; and wherein the compound of formula (I) is:

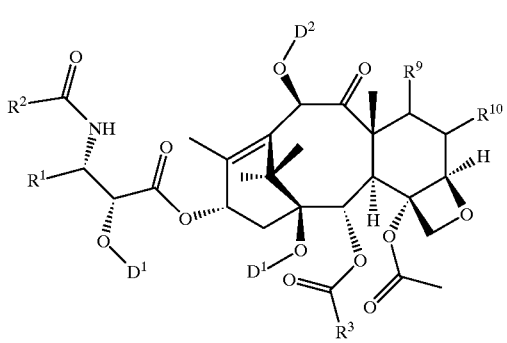

wherein:
R¹ is:

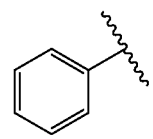

(a)

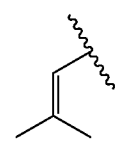

(b)

R² is:

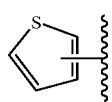
(c)

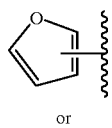
or
(d)

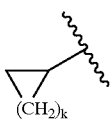
(e)

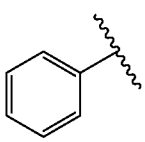
(a)

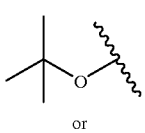
(b)

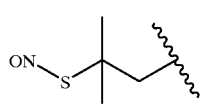
or
(c)

R³ is:

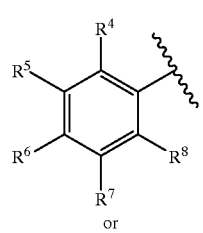
or
(a)

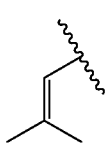
(b)

$R^4$, $R^5$, $R^6$, $R^7$ and $R^8$ are each independently a hydrogen, a lower alkyl group, an alkenyl, an alkynyl, an alkoxy, a halo, a haloalkyl, a nitro or an amino;

$R^9$ and $R^{10}$ are each independently a hydrogen, —OD¹, —SD¹ or a halo;

D¹ is a hydrogen or D;

D² is a hydrogen, —C(O)CH₃ or D;

D is Q or K;

Q is —NO or —NO₂;

K is —$W_a$—$E_b$—$(C(R_e)(R_f))_p$—$E_c$—$(C(R_e)(R_f))_x$—$W_d$—$(C(R_e)(R_f))_y$—$W_i$—$E_j$—$W_g$—$(C(R_e)(R_f))_z$—T—Q;

a, b, c, d, g, i and j are each independently an integer from 0 to 3;

p, x, y and z are each independently an integer from 0 to 10;

W at each occurrence is independently —C(O), —C(S), —T, —$(C(R_e)(R_f))_h$, an alkyl group, an aryl group, a heterocyclic ring, an arylheterocyclic ring, or —$(CH_2CH_2O)_q$;

E at each occurrence is independently —T—, an alkyl group, an aryl group, —$(C(R_e)(R_f))_h$, a heterocyclic ring, an arylheterocyclic ring, or —$(CH_2CH_2O)_q$;

h is an integer form 1 to 10;

q is an integer from 1 to 5;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a urea, a phosphoryl, a nitro, $W_h$, —T—Q, or —$(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group;

k is an integer from 1 to 3;

T at each occurrence is independently a covalent bond, a carbonyl, an oxygen, —S(O)ₒ or —N(Rₐ)Rᵢ;

o is an integer from 0 to 2;

$R_a$ is a lone pair of electrons, a hydrogen or an alkyl group;

$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH₂—C(T—Q)($R_e$)($R_f$), or —(N₂O₂—)⁻•M⁺, wherein M⁺ is an organic or inorganic cation; with the proviso that the compounds of Formula (I) must contain at least one NO group, or at least one NO₂ group; wherein the at least one NO group or the at least one NO and NO₂ group is linked to the compound of Formula (I) through an oxygen atom, a nitrogen atom or a sulfur atom, and —OD¹ and —OD² are not —O—NO₂; $R^9$ is not —O—NO₂ or the D¹ group at $R^9$ does not contain a nitroaryl group or a nitroxyloside group; and $R^{10}$ is not —O—NO₂.

52. The composition of claim 51, wherein the polymer is a polyolefin, a polyethylenimine, a polyethyleneimine derivative, a polyether, a polyanhydride, a polyhydroxybutyrate, a polyester, a polyamide, a polyurethane, a copolymer, a blocked polymer, a blocked coploymer, a biopolymer, a starburst dendrimer, or a mixture thereof.

53. The composition of claim 51, further comprising at least one compound that is a compound that donates, transfers or releases nitric oxide, or induces the production of endogenous nitric oxide or endothelium-derived relaxing factor, or is a substrate for nitric oxide synthase, at least one therapeutic agent or a mixture thereof.

54. A method for delivering nitric oxide to a targeted site in a patient in need thereof comprising administering the composition of claim 51 or 53 to the targeted site in the patient.

55. The method of claim 54, wherein the composition provides sustained delivery of nitric oxide to the targeted sited in the patient.

56. A medical device comprising the composition of claim 51 or 53.

57. The medical device of claim 56, wherein the composition coats all or a portion of the surface of the medical device.

58. The medical device of claim 56, wherein the composition forms all or part of the medical device.

59. The medical device of claim 56, wherein the medical device is a balloon, a catheter tip, a stent, a catheter, a prosthetic heart valve, a synthetic vessel graft, an arteriovenous shunt, a heart valve, a suture, a vascular implant, a drug pump, a drug delivery catheter, plastic tubing, a dialysis bag, a lead, a pacemaker, an implantable pulse generator, an implantable cardiac defibrillator, a cardioverter defibrillator, a defibrillator, a spinal stimulator, a brain stimulator, a sacral nerve stimulator, a chemical sensor or a membrane surface.

60. A method for preventing platelet aggregation and platelet adhesion caused by the exposure of blood to a medical device comprising incorporating at least one composition of claim 51 or 53 or a pharmaceutically acceptable salt thereof, into or on the medical device.

61. The method of claim 60, wherein the medical device is a balloon, a catheter tip, a stent, a catheter, a prosthetic heart valve, a synthetic vessel graft, an arteriovenous shunt, a heart valve, a suture, a vascular implant, a drug pump, a drug delivery catheter, plastic tubing, a dialysis bag, a lead, a pacemaker, an implantable pulse generator, an implantable cardiac defibrillator, a cardioverter defibrillator, a defibrillator, a spinal stimulator, a brain stimulator, a sacral nerve stimulator, a chemical sensor or a membrane surface.

62. The method of claim 60, wherein the blood is a blood product or a blood component.

63. A method for treating injured tissue in a patient in need thereof comprising administering at least one composition of claim 51 or 53 or a pharmaceutically acceptable salt thereof, to the site of the injured tissue in the patient.

64. The method of claim 63, wherein the injured tissue is a blood vessel.

65. The method of claim 63, wherein the compound is administered to the site of the injured tissue via at least one of a suture, a vascular implant, a stent, a heart valve, a drug pump or a drug delivery catheter.

66. A composition comprising at least one taxane or a pharmaceutically acceptable salt thereof and at least one compound that donates, transfers, or releases nitric oxide, or induces the production of endogenous nitric oxide or endothelium-derived relaxing factor or is a substrate for nitric oxide synthase or a pharmaceutically acceptable salt thereof.

67. The composition of claim 66, wherein the at least one taxane is paclitaxel, docetaxel or baccatin III.

68. The composition of claim 66, wherein the at least one compound that donates, transfers, or releases nitric oxide, or induces the production of endogenous nitric oxide or endothelium-derived relaxing factor or is a substrate for nitric oxide synthase is an S-nitrosothiol.

69. The composition of claim 68, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

70. The composition of claim 68, wherein the S-nitrosothiol is:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an alkylaryl, a carboxamido, an alkylcarboxamido, an arylcarboxamido, an amidyl, a carboxyl, a carbamoyl, a carbamate, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, $W_h$, —T—Q, or —$(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group; Q is —NO or —$NO_2$; and T is independently a covalent bond, a carbonyl, an oxygen, —$S(O)_o$ or —$N(R_a)R_i$, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T-Q)(R_e)(R_f)$, or —$(N_2O_2-)•M^+$, wherein $M^+$ is an organic or inorganic cation; with the proviso that when $R_i$ is —$CH_2$—$C(T-Q)(R_e)(R_f)$ or —$(N_2O_2-)•M^+$; then "—T—Q" can be a hydrogen, an alkyl group, an alkoxyalkyl group, an aminoalkyl group, a hydroxy group or an aryl group.

71. The composition of claim 66, wherein the at least one compound that donates, transfers, or releases nitric oxide, or induces the production of endogenous nitric oxide or endothelium-derived relaxing factor, or is a substrate for nitric oxide synthase is:

(i) a compound that comprises at least one ON—O—, ON—N— or ON—C— group;

(ii) a compound that comprises at least one $O_2N$—O—, $O_2N$—N—, $O_2N$—S— or —$O_2N$—C— group;

(iii) a N-oxo-N-nitrosoamine having the formula: $R^1R^2N$—$N(O-M^+)$—NO, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and M$^+$ is an organic or inorganic cation.

72. The composition of claim 71, wherein the compound comprising at least one ON—O—, ON—N— or ON—C— group is an ON—O-polypeptide, an ON—N-polypepetide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

73. The composition of claim 71, wherein compound comprising at least one $O_2N$—O—, $O_2N$—N—, $O_2N$—S— or $O_2N$—C-group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heterocyclic compound or an $O_2N$—C-heterocyclic compound.

74. The composition of claim 66, wherein the at least one compound that donates, transfers, or releases nitric oxide, or induces the production of endogenous nitric oxide or endothelium-derived relaxing factor, or is a substrate for nitric oxide synthase, is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, ornithine, glutamine, lysine, polypeptides comprising at least one of these amino acids or inhibitors of the enzyme arginase.

75. The composition of claim 66, wherein the at least one compound that donates, transfers or releases nitric oxide, elevates endogenous levels of endothelium-derived relaxing factor, stimulates endogenous synthesis of nitric oxide or is a substrate for nitric oxide synthase is a NONOate.

76. The composition of claim 66, further comprising at least one therapeutic agent.

77. The composition of claim 76, wherein the therapeutic agent is an antithrombogenic agent, a thrombolytic agent, a fibrinolytic agent, a vasospasm inhibitor, a potassium channel activator, a calcium channel blocker, an antihypertensive agent, an antimicrobial agent, an antibiotic, an antiplatelet agent, an antimitotic agent, an antiproliferative agent, a microtubule inhibitor, an antisecretory agent, a remodelling inhibitor, an antisense nucleotide, an anti-cancer chemotherapeutic agent, a steroid, a non-steroidal antiinflammatory agent, a selective COX-2 inhibitor, an immunosuppressive agent, a growth factor antagonist or antibody, a dopamine agonist, a radiotherapeutic agent, a heavy metal functioning as a radioplaque agent, a biologic agent, an angiotensin converting enzyme inhibitor, an angiotensin II receptor antagonist, a renin inhibitor, a free radical scavenger, an iron chelator, an antioxidant, a sex hormone, an antipolymerase, an antiviral agent, a photodynamic therapy agent, an antibody targeted therapy agent, a gene therapy agent, or a mixture thereof.

78. A method for treating or preventing a cardiovascular disease or disorder in a patient in need thereof comprising administering a therapeutically effective amount of the composition of claim 66 or 76.

79. The method of claim 78, wherein the cardiovascular disease or disorder is restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications associated with the use of medical devices, wounds associated with the use of medical devices, myocardial infarction, pulmonary thromboembolism, cerebral thromboembolism, thrombophlebitis, thrombocytopenia or bleeding disorders.

80. The method of claim 79, wherein the cardiovascular disease or disorder is restenosis or atherosclerosis.

81. A method for treating or preventing an autoimmune disease, a pathological condition resulting from abnormal cell proliferation, polycyctic kidney disease, an inflammatory disease, for preserving an organ and/or a tissue or for inhibiting wound contraction in a patient in need thereof comprising administering a therapeutically effective amount of the composition of claim 66 or 76.

82. The method of claim 81, wherein the pathological condition resulting from abnormal cell proliferation is a cancer, a Karposi's sarcoma, a cholangiocarcinoma, a choriocarcinoma, a neoblastoma, a Wilm's tumor, Hodgkin's disease, a melanoma, multiple myelomas, a chronic lymphocytic leukemia or an acute or chronic granulocytic lymphoma.

83. The method of claim 81, wherein the inflammatory disease is rheumatoid arthritis, an inflammatory skin disease, restenosis, multiple sclerosis, a surgical adhesion, tuberculosis, a graft rejection, an inflammatory lung disease, an inflammatory bowel disease, an inflammatory disease that affects or causes obstruction of a body passageway, an inflammation of the eye, an inflammation of the nose, an inflammation of the throat or a neovascular diseases of the eye.

84. The method of claim 78 or 81, wherein the compound is administered intravenously, orally, bucally, parenterally, by an inhalation spray, by topical application or transdermally.

85. The method of claim 78 or 81, wherein the composition is administered via local administration.

86. The method of claim 85, wherein the local administration of the compound is via a suture, a vascular implant, a stent, a heart valve, a drug pump, a drug delivery catheter, an infusion catheter, a drug delivery guidewire or an implantable medical device.

87. A method for delivering nitric oxide to a targeted site in a patient in need thereof comprising administering the composition of claim 66 or 76 to the targeted site in the patient.

88. The method of claim 87, wherein the composition provides sustained delivery of nitric oxide to the targeted sited in the patient.

89. A composition comprising at least one taxane or a pharmaceutically acceptable salt thereof and at least one compound that donates, transfers, or releases nitric oxide, or induces the production of endogenous nitric oxide or endothelium-derived relaxing factor or is a substrate for nitric oxide synthase or a pharmaceutically acceptable salt thereof bound to a matrix, wherein the matrix is at least one of a natural polymer, a synthetic polymer, a natural fiber, a synthetic fiber or a mixture thereof.

90. The composition of claim 89, wherein the polymer is a polyolefin, a polyethylenimine, a polyethyleneimine derivative, a polyether, a polyanhydride, a polyhydroxybutyrate, a polyester, a polyamide, a polyurethane, a copolymer, a blocked polymer, a blocked copolymer, a biopolymer, a starburst dendrimer, or a mixture thereof.

91. The composition of claim 89, further comprising at least one therapeutic agent.

92. A method for delivering nitric oxide to a targeted site in a patient in need thereof comprising administering the composition of claim 89 or 91 to the targeted site in the patient.

93. The method of claim 92, wherein the composition provides sustained delivery of nitric oxide to the targeted sited in the patient.

94. A medical device comprising the composition of claim 89 or 91.

95. The medical device of claim 94, wherein the composition coats all or a portion of the surface of the medical device.

96. The medical device of claim 94, wherein the composition forms all or part of the medical device.

97. The medical device of claim 94, wherein the medical device is a balloon, a catheter tip, a stent, a catheter, a prosthetic heart valve, a synthetic vessel graft, an arteriovenous shunt, a heart valve, a suture, a vascular implant, a drug pump, a drug delivery catheter, plastic tubing, a dialysis bag, a lead, a pacemaker, an implantable pulse generator, an implantable cardiac defibrillator, a cardioverter defibrillator, a defibrillator, a spinal stimulator, a brain stimulator, a sacral nerve stimulator, a chemical sensor or a membrane surface.

98. A method for preventing platelet aggregation and platelet adhesion caused by the exposure of blood to a medical device comprising incorporating at least one composition of claim 89 or 91 or a pharmaceutically acceptable salt thereof, into or on the medical device.

99. The method of claim 98, wherein the medical device is a balloon, a catheter tip, a stent, a catheter, a prosthetic heart valve, a synthetic vessel graft, an arteriovenous shunt, a heart valve, a suture, a vascular implant, a drug pump, a drug delivery catheter, plastic tubing, a dialysis bag, a lead, a pacemaker, an implantable pulse generator, an implantable cardiac defibrillator, a cardioverter defibrillator, a defibrillator, a spinal stimulator, a brain stimulator, a sacral nerve stimulator, a chemical sensor or a membrane surface.

100. The method of claim 98, wherein the blood is a blood product or a blood component.

101. A method for treating injured tissue in a patient in need thereof comprising administering at least one composition of claim 89 or 91 or a pharmaceutically acceptable salt thereof, to the site of the injured tissue in the patient.

102. The method of claim 101, wherein the injured tissue is a blood vessel.

103. The method of claim 101, wherein the composition is administered to the site of the injured tissue via at least one of a suture, a vascular implant, a stent, a heart valve, a drug pump or a drug delivery catheter.

104. A kit comprising at least one compound of claim 2 and at least one compound that donates, transfers, or releases nitric oxide, or induces the production of endogenous nitric oxide or endothelium-derived relaxing factor or is a substrate for nitric oxide synthase, or a pharmaceutically acceptable salt thereof.

105. The kit of claim 104, further comprising at least one therapeutic agent.

106. The kit of claim 104, wherein the compound of claim 2 and the compound that donates, transfers, or releases nitric oxide, or induces the production of endogenous nitric oxide or endothelium-derived relaxing factor, or is a substrate for nitric oxide synthase are separate components in the kit or in the form of a composition in the kit.

107. A kit comprising at least one taxane and at least one compound that donates, transfers, or releases nitric oxide, or induces the production of endogenous nitric oxide or endothelium-derived relaxing factor or is a substrate for nitric oxide synthase, or a pharmaceutically acceptable salt thereof.

108. The kit of claim 107, further comprising at least one therapeutic agent.

109. The kit of claim 107, wherein the taxane and the compound that donates, transfers, or releases nitric oxide, or induces the production of endogenous nitric oxide or endothelium-derived relaxing factor, or is a substrate for nitric oxide synthase are separate components in the kit or in the form of a composition in the kit.

110. The method of claim 43, wherein the compound is administered intravenously, orally, bucally, parenterally, by an inhalation spray, by topical application or transdermally.

111. The method of claim 43, wherein the composition is administered via local administration.

112. The method of claim 111, wherein the local administration of the compound is via a suture, a vascular implant, a stent, a heart valve, a drug pump, a drug delivery catheter, an infusion catheter, a drug delivery guidewire or an implantable medical device.

113. A compound selected from the group consisting of 15-((3S,2R)-2-hydroxy-3-phenyl-3-(phenylcarbonylamino)propanoyloxy)(2S,4S,9S,10S,15S,7R,12R)-4,12-diacetyloxy-1-hydroxy-10,14,17,17-tetramethyl-6-oxa-11-oxo-2-phenylcarbonyloxytetracyclo(11.3.1.0<3,10>0.0<4,7>)heptadec-13-en-9-yl 3-methyl-3-(nitrosothio)butanoate; (1S,2S,4S,9S,10S,15S,7R,12R)-4,12-diacetyloxy-1,9-dihydroxy-10,14,17,17-tetramethyl-6-oxa-11-oxo-2-phenylcarbonyloxytetracyclo(11.3.1.0<3,10>0.0<4,7>)heptadec-13-en-15-yl(3S,2R)-2-(2-({N-(2-methyl-2-(nitrosothio)propyl)carbamoyl}methoxy)acetyloxy)-3-phenyl-3-(phenylcarbonylamino)propanoate; 9-(2-({((2R)-2,3-bis(nitrooxy)propyl)oxycarbonyl}methoxy)acetyloxy) (1S,2S,4S,9S,10S,15S,7R,12R)-4,12-diacetyloxy-1-hydroxy-10,14,17,17-tetramethyl-6-oxa-11-oxo-2-phenylcarbonyloxytetracyclo(11.3.1.0<3,10>0.0<4,7>)heptadec-13-en-15-yl 2-(2({(((2R)-2,3-bis(nitrooxy)propyl)oxycarbonyl}methoxy)acetyloxy)(3S,2R)-3-phenyl-3-(phenylcarbonylamino)propanoate; (1S,2S,4S,9S,10S,15S,7R,12R)-4,12-diacetyloxy-9-{2-(({2,2-bis((nitrooxy)methyl)-3-(nitrooxy)propyl}oxycarbonyl)methoxy)acetyloxy}-1hydroxy -10,14,17,17-tetramethyl-6-oxa-11-oxo-2-phenylcarbonyloxytetracyclo(11.3.1.0<3,10>0.0<4,7>)heptadec-13-en-15-yl (3S ,2R)-2-{2-(({2,2-bis((nitrooxy)methyl)-2-(nitrooxy)propyl}oxycarbonyl)methoxy)acetyloxy}-3-phenyl-3-(phenylcarbonylamino)propanoate, or a pharmaceutically acceptable salt thereof.

* * * * *